US008389805B2

(12) United States Patent
Apuya et al.

(10) Patent No.: US 8,389,805 B2
(45) **Date of Patent: *Mar. 5, 2013**

(54) PROMOTER, PROMOTER CONTROL ELEMENTS, AND COMBINATIONS, AND USES THEREOF

(75) Inventors: Nestor Apuya, Culver City, CA (US); Shing Kwok, Woodland Hills, CA (US); Nickolai Alexandrov, Thousand Oaks, CA (US); Tatiana Tatarinova, Los Angeles, CA (US); Yiwen Fang, Los Angeles, CA (US); Roger Pennell, Malibu, CA (US); Yu-Ping Lu, Oak Park, CA (US); Leonard Medrano, Azusa, CA (US); Zhihong Cook, Woodland Hills, CA (US); Kenneth A. Feldmann, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 994 days.

This patent is subject to a terminal disclaimer.

(21) Appl. No.: 12/103,970

(22) Filed: Apr. 16, 2008

(65) Prior Publication Data

US 2009/0133163 A1 May 21, 2009

Related U.S. Application Data

(62) Division of application No. 11/233,726, filed on Sep. 23, 2005, now Pat. No. 7,378,571.

(60) Provisional application No. 60/637,174, filed on Dec. 16, 2004, provisional application No. 60/612,891, filed on Sep. 23, 2004, provisional application No. 60/613,134, filed on Sep. 23, 2004.

(51) Int. Cl.

| | |
|---|---|
| ***A01H 1/00*** | (2006.01) |
| ***C12N 15/63*** | (2006.01) |
| ***C12N 15/00*** | (2006.01) |
| ***C07H 21/04*** | (2006.01) |

(52) U.S. Cl. ..................... 800/287; 536/24.1; 435/320.1

(58) Field of Classification Search ........................ None
See application file for complete search history.

(56) References Cited

U.S. PATENT DOCUMENTS 7,378,571 B2 * 5/2008 Apuya et al. ................. 800/287

FOREIGN PATENT DOCUMENTS

| | | |
|---|---|---|
| EP | 1209228 | 5/2002 |
| WO | WO-0216655 | 2/2002 |

OTHER PUBLICATIONS

Kaneko et al. 1999, DNA Research 6:183-195.*

Li, L., et al. "An upstream repressor element that contributes to hepatocyte-specific expression of the rat serum amyloid A1 gene", Biochem Biophys Res Commun, (1999), vol. 264, pp. 395-403.

Thomas, b., et al., "Glucose mediates transcriptional repression of the human angiotensin type-1 receptor gene", Mol Bio Cell, (2004), vol. 15, pp. 4347-4355.

Structural Analaysis of *Araidopsis thaliana* chromosomes 5. IX. Sequence Features of the Regions of 1,011,550 bp Covered by Seventeen P1 and TAC Clones, *DNA Research* 6, 183-195, (1999).

T-DNA integration into the *Arabidopsis* genome on sequences of pre-insertion sites, *Scientific Report, EMBO Reports*, vol. 3, No. 12, pp. 1152-1157, 2002.

Database EMBL [Online] May 16, 1997, "F21F10-T7 IGF *Arabidopsis thaliana* genomic clone F21F10, genomic survey sequence," XP002365435, retrieved from EBI accession No. EM_PRO:AT1217916, Database accession No. AT1217916, abstract.

Database EMBL [Online] May 16, 2003, "A stress-responsive promoter," XP002365436, retrieved from EBI accession No. EM_PRO:BD181334, Database accession No. BDI181334, abstract.

* cited by examiner

*Primary Examiner* — Li Zheng

(74) *Attorney, Agent, or Firm* — Birch, Stewart, Kolasch & Birch, LLP

(57) ABSTRACT

The present invention is directed to promoter sequences and promoter control elements, polynucleotide constructs comprising the promoters and control elements, and methods of identifying the promoters, control elements, or fragments thereof. The invention further relates to the use of the present promoters or promoter control elements to modulate transcript levels.

14 Claims, 3 Drawing Sheets

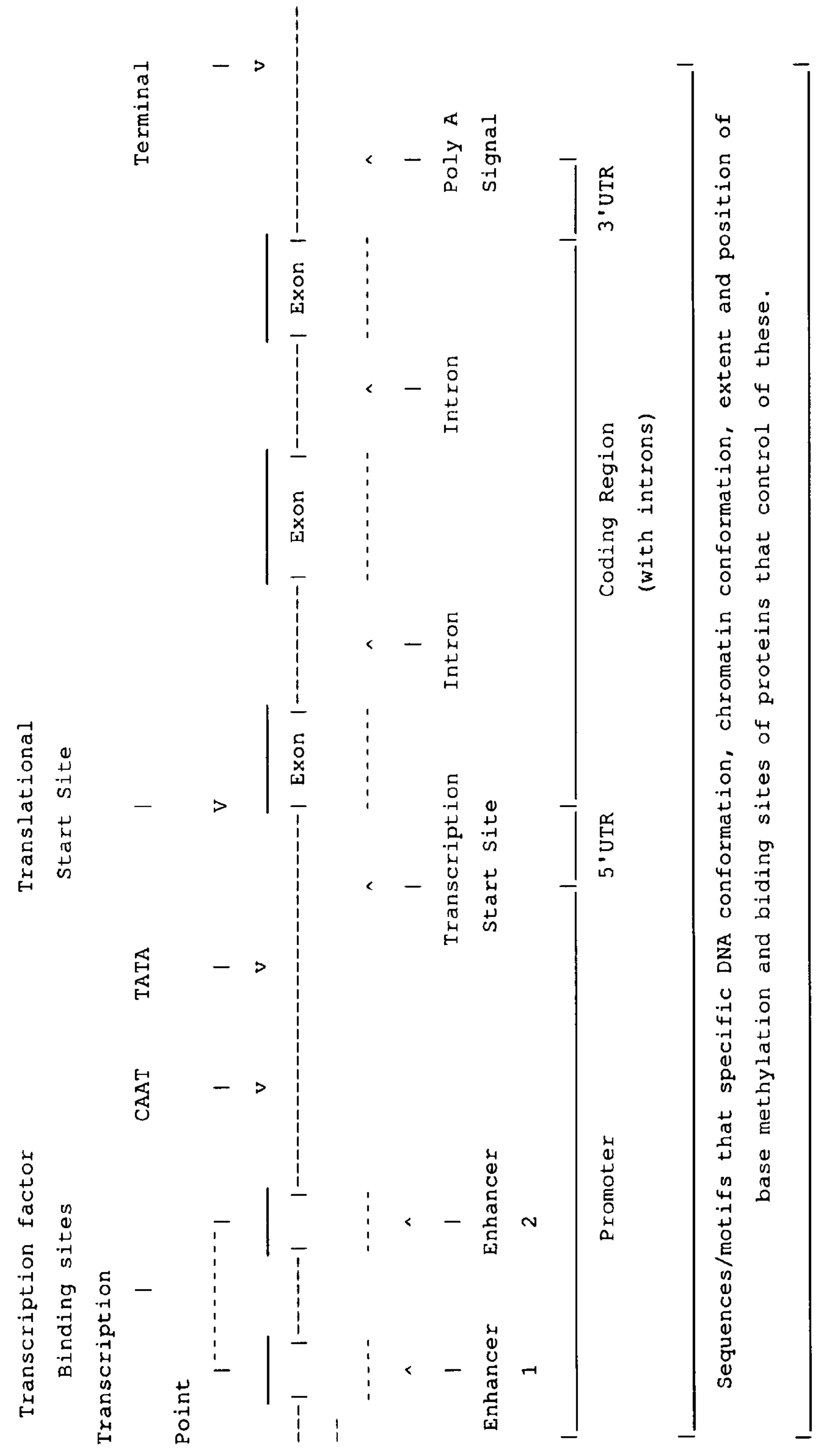
Figure 3
SCHEMATIC OF A GENE
Transcription factor
Binding sites
Transcription
Point
CAAT
TATA
Translational
Start Site
Terminal
Enhancer
1
Enhancer
2
Transcription
Start Site
Exon
Intron
Exon
Intron
Exon
Poly A
Signal
Promoter
5'UTR
Coding Region
(with introns)
3'UTR
Sequences/motifs that specific DNA conformation, chromatin conformation, extent and position of
base methylation and biding sites of proteins that control of these.
Gene

SEQUENCE LISTING

<160> NUMBER OF SEQ ID NOS: 46

<210> SEQ ID NO 1
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0390 as found in Promoter Report #132

<400> SEQUENCE: 1

```
tccttgcatt tattatagtg cctagatttt tttttttttt tttttgacat tcagtgccta     60
gaattttggt ttatgtagat agaaaagtga cactcgacgc aaattcgaaa gaatgccacc    120
gaaaaaaatg gaacgaatga tgtttcgcta tgttggatgc ttcagatccc atataacaac    180
actactctca aaattcataa actctcaaaa catattaatt tagtagcatc acgaaaatac    240
atgttgttct caaatcatta caataacttc tactcttatt agctgaaaag tataacctta    300
tgtttttgta aaaagattgc taaacgttat atttgtatat cttttcagtt tgttaatgtc    360
attagaacga agtgtaaaat cgcttcaaga tttgttattc taaatgtatt ttagaacaaa    420
tattctgaac attaaattat tttcaacaaa atttattttg aataacaaat aacttgtcat    480
ggtcgtaact cttttttttc attctctaga ttgaatcaaa aataattttg ttttgtagta    540
taaaacattt ttggtctttt attcaccgtt ttatagaaca ttaatatctc aagttctaat    600
atgaaaacaa aaataactga tccctcaaaa aaaaggaaga taaaggttga aagacatgtt    660
attctcttcc caaaacaacc taatccaata cctctaaaaa tttatctttc tcacaatgcc    720
ttcaaacaaa ttgtgttctt tctatagtta acttgactat attaaaatct ctaaagttaa    780
cttgacttct gaaacttgtg atctttctat agttaacttg actatattaa aatcttgagc    840
aattaaacca ttaaaaaaaa aaaaaacagg agaaaccttg accaatacaa caaatcctaa    900
aaatggccaa cgataagaat cacaacagaa atttaaagac tacatgtaac tatttatact    960
acagaaaaca ccaaatagaa tccaatcaaa aaaaaaaaaa                         1000
```

<210> SEQ ID NO 2
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0681 as found in Promoter Report #176

<400> SEQUENCE: 2

```
gacttttttt ttatggagaa caaattatcc agtagatgtt tttttttatt gctcagtaat     60
tgagaaatgg gcacgaggat gaagatattc cattgatgtg attccaatct taataacatt    120
gcaatttcgt agctatataa atcatttcat gtgtaatatt atccatcttg ttaaattttc    180
taatctctaa aatttcatac cgtttgtgtt taacatagtt tccgatccaa tccaatccag    240
caaagtgaaa taatttcgaa tgataaggct gttttgcaaa atgccaaata tggcggaaca    300
atttttattt aagaaacaag ataaggatta ttaatgatca gatatgcttg atgaagttgt    360
ggtccattct tacttctctt ctgcatattt atcacatcgg tttctcatta tctctatgca    420
ttcgggacta ctaatacaac aatagcacaa aaatacaacg tgacaacaaa aacaaccgag    480
```

```
tagaaaacta taaagacaac aacatttcaa attctctgtt gccactaata ctgaaaatcc    540

atttaaattt tctttttgtg ggttgaattt gcaccatata aaaatccaat aatacaaaag    600

aaagcaaata tacatgattg gatattcttc gattatgatg tcgaacaaca acaattatta    660

acatgtgtat agtttggcaa aaaatgaata tgaggtaaag agggctggac ccattggccc    720

tataagcatt aatgggcctg aaagcaacaa cagaaattgg aattaaataa cgttgggtat    780

ctgtctgtca catgcaacac agacaacttg agaatggatc aatcaacatt cacgtgccat    840

gatcctctct tcctcttatt ttgtctcctt ccaccaatcc catatctttc tctattatac    900

atctctaatt atctcacttt taacatatag tttttttata catctttaat gactatataa    960

accaaacact gatctttttc aggttgcgaa taaaccaaga                        1000


<210> SEQ ID NO 3
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0675 as found in
      Promoter Report #204

<400> SEQUENCE: 3

ttgtttaaca cctcaaacct gttaagacta atcacaatgt tcgaagataa tgccatttct     60

atatatattt agtatagcat cacacatgcg ttctgtgttg caaagtttac tctagagtta    120

tcactgagtc atgactcatg atgaccatta ttatagtatt agtactttta agttttaggt    180

cgagaatgtg aagctaatac atgcatgtaa tgatgtaaat atgcctacct taaaaaatat    240

cgaattattc agaaacaatg actcgatatc cgtaagaaac cgccagctcc tgctgaattg    300

catgaaccta tcttaatatt ctttcgccac gaactcttcc cttttgtctc cttcttataa    360

ctctacacat catcatttct tttccactaa ataacttaca atacgtatac ctttttcttt    420

tttgtcaatt taaatcaaca ctaagatata ctttaaatac gaatcattta aatgaatata    480

atgtactaat tgtttcagat tttatttcct gtttaaaaat atactcatga actaaaacta    540

attaataaaa tgtggataaa ttaaagcctt ttaacaaaaa aaaaatgtgg ataaattaat    600

atcaatatgt ttcctttttta ttttatttta tctatttcaa aaaaataagt tattcaatac    660

atatgttgat attttgacta tttttaatca taatttaaat caattgttgt gttcttaagc    720

aaaatatcta aaaacgaata taaccacgtc caccatagaa gcactgcaat tttagcattc    780

taaaacatcc ttgatatttt tttgtcaacg tcttattatc ttttatctca gaccatgtat    840

atggatgtat ccactaacgc atatatatag agacaattag gcatctatca ttttatccca    900

cacttatctc ttcctatctc tctctcattc aaacccaaat aggaaacaaa tacacaaaag    960

tataataaaa agtctttctc tcatctttcg ccacgtagac                        1000


<210> SEQ ID NO 4
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0676 as found in
      Promoter Report #205

<400> SEQUENCE: 4

aagatagtac agtttcagtg ttttgagaaa aaaagctgaa ctaaaactaa aatgtttaag     60
```

-continued

```
gacacaatat ttagtttcaa ttagataatt caacagtttg aacaattttt tttttttttt    120

tttgaagtca tttatttata caatgtttta aaacgcatta agcatttagg cagccgacaa    180

acgcctattg tctaactgta aataggcgct tccacttagg ttcatattgc atatttacta    240

tatgtgtata gtgacaaaaa ccaatatttc tcttattttg gatgaaggta tagtagttgt    300

taaatgttca atataattaa gcattaatga caaataaaat aaaattaatt tagttgataa    360

aaagataatc ttataaaaag atcgatgaat agatataatg gtttactgaa ttctatagct    420

cttaccttgc acgactatgt cccaaggaga ggaagtacct taactataat tctgaacata    480

attttgtcta tcttggtgag tattatatga cctaaaccct ttaataagaa aaagtataat    540

actggcgtaa cgtaataaat taacacaatc ataagttgtt gacaagcaaa aaaacataca    600

taatttgttt aatgagatat attagttata gttcttatgt caaagtacaa ttatgcctac    660

caaaattaat taatgatttc aacaggaagt ctgagatgat gggccgacgt gtagttacgt    720

ttcttgaatt gtgagagatg gtatttatta tactgaagaa aacattattt actaaataaa    780

ttttcatttc acatcttctg taatcaatgc gggtagatga agaagttgtt aatacgatgg    840

ccaaccatat ggatctcttt tttggcgttt ctatatatag taacctcgac tccaaaggca    900

ttacgtgact caataaaatc aagtcttttg tttcctttta tccaaaaaaa aaaaaaagtc    960

ttgtgtttct cttaggttgg ttgagaatca tttcatttca                         1000
```

<210> SEQ ID NO 5
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0698 as found in Promoter Report #234

<400> SEQUENCE: 5

```
gaagcataga ttcttggatg tattcatatt ccttgcttta agtccttccg tctcaatttt     60

aacaactatg gtcacatgtc catactgatc tcgtaccatg cacttgtctt cacatgcttc    120

ttcattttct atttttgggt attcgacaaa taaatcgtgc atggaaatga atgtggtatc    180

gtccaatgca gtttacgaga taatacatat atttttattt ttgttaaaaa gtaataataa    240

tacacaatta ataatatatt attaccaaaa attataaaca aatattaatt gcatgggatg    300

aatttctggt tgttgatttg ttggttcaga ctaggtttgt attcactaga gaacttcaaa    360

tatgctgaaa ttcgaccact caaaagcaag tgagactcta attgtcaagg gaaatagaag    420

acgctttaag atcggatcgt tgaggattag cttgcatgaa gtctgaagat atcttcaaga    480

agggactttg ggttgggtcc gccatggtag tgtttttgtg acttacaccg aaaatcttta    540

attatatgga ggaatagtaa atcttgctaa gtaatcccgt taacttatta attgaatata    600

tttttatgtt aataatattt gtcctaaacg aaaagtatat ctatttctct aatcatcaaa    660

taaaacaatg agtataagat acttacatat ttaatttgtt tttcttgatc ttaaattaga    720

attattaatt gattctttta gtttcaaata tcatgcaaat atagatggca aaagattcga    780

gcatataaat atggtacttc aaattgtgaa agtacgattt gattttctct tttctttgtt    840

gtacgtatga tattaaaagt agaggaatat gattcttgag tgtagaatct tgccttctac    900

catggttcaa gtgtaagcaa tataaaaaag ggagatgtgt gtttatttct tcccaacttt    960

gatactcaca agacatcttt ttaattcact cccttgcaaa                         1000
```

<210> SEQ ID NO 6
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0708 as found in Promoter Report #235

<400> SEQUENCE: 6
gtttccaaaa ctagtattct ttatttgctc tattcattat atttttatat ttgtaacgtc 60
ccgaccgtct ttattaggtt tcgacaatca cttctcggaa ggtcgtccat cctgaaatta 120
ctctatccta aacatgttta actataaaat tctctcgaaa cttttgtaac gtatataacc 180
acataaattc tcttaaactt atttgcatac accattatat ttctgaaatc gatatgttac 240
aatattattt aatatttaga ttacttttac tgaatcgaat taaatatcaa atcgaaacaa 300
atctaatcta ccaaaaataa ttttgttata aacatttctt gcctagttct acctcatata 360
cattttagtt aaagaaagaa atcacaacaa ttcccataat tcaataatta aatccacaaa 420
atcttggagt aagtaagaga aataaaaaga tagtatctta acataaacaa ttcaaagatg 480
ctctctcaca caattcacac acacttacaa aacaaaagac agaaacaatg ttttcattca 540
aatcaaaaga agttataaca ctagtacaaa aaaagctcaa attctaatag taactctttt 600
tatttcccaa ttacccaaag attctctctc acttcacaaa actagctttg agagtcgtgt 660
tccacaaaat ccattaaagc tgaaacggtt ttgctcacca ttcaaacaaa tacaaaattg 720
caaaacccca aattataaca aaataatata aaaattaaac cgctaaaaag agtgaaccaa 780
caaaaatcgc cgaatgtgtg tgtaatgaga aaaccgaccc atcatcccaa tcatctcttc 840
ccgtgtcact ctcttcctct cccacgtttc ttctctcttc cctttatggg ttttaacttc 900
tccttcttct tcttcttcaa tcttcagttt tcaaattcaa caacaattca cattttgatt 960
tcttcatcat ctctctctct ctcgcttctc tctcaaatcg 1000

<210> SEQ ID NO 7
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0710 as found in Promoter Report #236

<400> SEQUENCE: 7
tagtgcgcgt ggggagaggg aatggtgaaa ccttagtggt taagttatga ggaaaatgat 60
aaaaggataa aacaatcaaa tgcagcttga aacggccata acataaagta ccttatggtg 120
gtgcgaatat ttttgtgttt ctttcactct tttattgctg aaagctacga cacttgtctt 180
aatatattgt ttccgcaagt cacatgatct actttttatt taacgtctag aaacgccgag 240
atatatgatg attagtatat cacgtctatg caaattgtta gttcgtgttt ggccaaaaga 300
tatcgagaca tgtctgaaga accgagtctg gttttgagat atttcttcaa gcattactat 360
acaatagaaa aaggagacac gcgaatatga taatagcaaa aggcataaaa aggcgaaaat 420
taaagaaaaa cgtaaagtga tttggcctca atcaacggga acgtatctta attttagagg 480
ttcttctttt acttttgaga cgagagagtt tgcgtctttg cgagctgctt tggttgacta 540
aacattatca tattgaaaac caaaatacaa cggaggaata tttgtcacag tttcactttc 600
acattgtttc cttaacgttt aatcaacctt gttcaaaatt tctatagttg taatcatcat 660

```
tgtttacaaa attttcgttc aaagatgatt ttaaataaaa ttgtgaaaga aaaccttttc    720

tgaaataagg attggatgat agtgttaaaa gaaaaatatg aactgaggca aaaagaggag    780

tggtccccgg aagattgtga aatgtgtcat ctaaaccagc cagacgtagt cacgtgttct    840

ctctagcttt atgaacttcc ttagccagca ccatcattgt gattgtagta tatatgtaac    900

cctaccttca tctctcccat tttccattct ccatatagac tcctttacaa tatacaaaac    960

ctatccaaaa gcgaagaagc caagcaaaca tattataaaa                         1000


<210> SEQ ID NO 8
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0721 as found in
      Promoter Report #237

<400> SEQUENCE: 8

aaagaagaaa aagtgtacac atgtttttgt ccagccccat taccaatata ccgatctgga     60

tatcatctag ctcacatttc atgataaaag caaactcaga tggaatgtgt gtactgggct    120

ttattgggct aaacttgaac tgagcttttt atttttaaaa ataaataaaa gaaacaacaa    180

ggccgatgat tttttcttag gtctaaaaag tctaaagtaa acccatttgt attgttttgt    240

atataatatt atataattta caaaaatatt gaaacgagta gttctgatat tttgtttcta    300

tactttgaca tgttttcgtg cacaaagttc ctcagttttt tttcccaaac aacaaccatt    360

tcagaaaatc tttcttctta gaaattttat ttcccaattt gaatagaaat atagatggaa    420

tggaaggcaa cgacttgaaa taataaagat aaggttggac atctaaagcc cataaaacaa    480

agctaatcca tgtaccattg tcatccacaa agcgtctcca cctaaagccc attttggatc    540

caaaattaaa tttatttgta agaaacaata tttctatttt gtcattttac ttgctgatca    600

agagtcgaaa aagatgcacg aaaagaaaca tacacaagcg aacacaatat aactaacact    660

aataggtaat agtttctgac acgtgtaggc ataataattg gtggctacgt ccctgcggcg    720

gttgcagtaa cgataaacac tccaccacta agagcgtctc atcacacgcg ccaatttcac    780

tcttacgatg gagataatgg gcgagtggga tagtgtatca cgtgacattc gcagacacaa    840

ctcgcttcat aactgaaaaa attaataata aaaaatggat atgtttgtct ttctctaatg    900

tttcatgaac atctgtaacg tcaaacccac tttaaaagct ctgctttttg tgtttgtttt    960

tgcttactct caaagaaagt ggttcaatct ctcgatttcc                         1000


<210> SEQ ID NO 9
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter construct PT0740 as found in
      Promoter Report #238

<400> SEQUENCE: 9

tgtggccact aaagatttac ccttaaccgg gcccatataa gcccacgtca agtggcgctt     60

atacgctctc cgtaagagag ccaacatttg gtatgtaatg ttgcaaatta ttcttcaaga    120

caataaattc aaatataatt caatattgtc caaatatagt gatgtacttc agttgtgcac    180

atagaaactc cactaaacca acttttagat agatgcattc acaaattttc aacaatgtcg    240
```

```
cgaaagtcta atccatcacc agattctaac attttaatta ttatatttaa ctatacatac    300

tctaatcagc atgagtcaaa cgtgtacaat agcccaagca tataataaga ccaaagtcaa    360

actcaaataa atgtctccaa actcaaaact tgaaaaagac ctaattatta catggtagat    420

atgactttgt cgacaagtaa accaactaat cctcgaagct accttctctt cccagttatt    480

atgtgtgatc gatttataaa tctcttcttc taataacacc tatatttttc ttatgatgtg    540

aataaatata aaacttttaa ctttaaaaca tatttatccg aaatattgca cttagatttc    600

aaatagataa ataatagtac tatctaactg atattgaaaa gacctaacac ggaaaacagt    660

tttataaaaa atcccaaatg tgggtaatta tcttgatttc ttgggggaaa cagaaaatgg    720

attaagatta atcggagtcg tgtcaagcag ctcgttaata actgtagcaa gttgactgag    780

taagcatcaa cgtgtcatct ccgtaaagcc cattatttct agtctcgccg cgtcttctct    840

tccacgtagc acttcacttt ttctctcctt ttgtttcctt tggaacacaa acgtttctat    900

ttataggaat aattacgtcg tccgtatctg tgtcggaaca tagatccaaa ttaaaagcga    960

cttacttaat tacatatcgt tcgtgttttt ttcttcaaaa a                      1001
```

```
<210> SEQ ID NO 10
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0286 as found in
      Promoter Report #111

<400> SEQUENCE: 10

gaaaacaatc ataggttacg ctattatcat cgaaaggtat gtgatgcata ttcccattga     60

accagatttc catatatttt atttgtaaag tgataatgaa tcacaagatg attcaatatt    120

aaaaatgggt aactcacttt gacgtgtagt acgtggaaga atagttagct atcacgcata    180

tatatatcta tgattaagtg tgtatgacat aagaaactaa aatatttacc taaagtccag    240

ttactcatac tgattttatg catatatgta ttatttattt atttttaata aagaagcgat    300

tggtgttttc atagaaatca tgatagattg ataggtattt cagttccaca aatctagatc    360

tgtgtgctat acatgcatgt attaattttt tccccttaaa tcatttcagt tgataatatt    420

gctctttgtt ccaactttag aaaaggtatg aaccaacctg acgattaaca agtaaacatt    480

aattaatctt tatatatatg agataaaacc gaggatatat atgattgtgt tgctgtctat    540

tgatgatgtg tcgatattat gcttgttgta ccaatgctcg agccgagcgt gatcgatgcc    600

ttgacaaact atatatgttt cccgaattaa ttaagttttg tatcttaatt agaataacat    660

ttttatacaa tgtaatttct caagcagaca agatatgtat cctatattaa ttactatata    720

tgaattgccg ggcacctacc aggatgtttc aaatacgaga gcccattagt ttccacgtaa    780

atcacaatga cgcgacaaaa tctagaatcg tgtcaaaact ctatcaatac aataatatat    840

atttcaaggg caatttcgac ttctcctcaa ctcaatgatt caacgccatg aatctctata    900

taaaggctac aacaccacaa aggatcatca gtcatcacaa ccacattaac tcttcaccac    960

tatctctcaa tctctcgttt catttcttga cgcgtgaaaa                         1000
```

```
<210> SEQ ID NO 11
<211> LENGTH: 1000
<212> TYPE: DNA
<213> ORGANISM: Arabidopsis thaliana
<220> FEATURE:
```

<221> NAME/KEY: misc_feature
<222> LOCATION: (1)..(1000)
<223> OTHER INFORMATION: Ceres Promoter construct YP0289 as found in
Promoter Report #112

<400> SEQUENCE: 11

```
atggactttt cttctattat atggtcaaac aattactgct caatgtattt gcgtatagag     60
catgtccaat accatgcctc atgatgtgag attgcgaggc ggagtcagag aacgagttaa    120
agtgacgacg tttttttgt ttttttggg catagtgtaa agtgatatta aaatttcatg    180
gttggcaggt gactgaaaat aaaaatgtgt ataggatgtg tttatatgct agacggaaaa    240
atagttactc aactaataca gatctttata aagagtatat aagtctatgg ttaatcatga    300
atggcaatat ataagagtag atgagattta tgtttatatt gaaacaaggg aaagatatgt    360
gtaattgaaa caatggcaaa atatatagtc aaatcaaact ggtttctgat aatatatgtg    420
ttgaatcaat gtatatcttg gtattcaaaa ccaaaacaac tacaaccaat ttctttaaaa    480
aaccagttga tctaataact acattttaat actagtagct attagctgaa tttcataatc    540
aatttcttgc attaaaattt aaagtgggtt ttgcatttaa acttactcgg tttgtattaa    600
tagactttca aagattaaaa gaaaactact gcattcagag aataaagcta tcttactaaa    660
cactactttt aaagtttctt ttttcactta ttaatcttct tttacaaatg gatctgtctc    720
tctgcatggc aaaatatctt acactaattt tattttcttt gtttgataac aaatttatcg    780
gctaagcatc acttaaattt aatacacgtt atgaagactt aaaccacgtc acactataag    840
aaccttacag gctgtcaaac acccttccct acccactcac atctctccac gtggcaatct    900
ttgatattga caccttagcc actacagctg tcacactcct ctctcggttt caaaacaaca    960
tctctggtat aaatacctct gtatatcttt ataaacccca                         1000
```

<210> SEQ ID NO 12
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0356 as found in
Promoter Report #125

<400> SEQUENCE: 12

```
ttagttcatt gaaacgtcaa ctttttactt gcaaccactt tgtaggacca ttaactgcaa     60
aataagaatt ctctaagctt cacaaggggt tcgtttggtg ctataaaaac attgttttaa    120
gaactggttt actggttcta taaatctata aatccaaata tgaagtatgg caataataat    180
aacatgttag cacaaaaaat actcattaaa ttcctaccca aaaaaaatct ttatatgaaa    240
ctaaaactta tatacacaat aatagtgata caaagtaggt cttgatattc aactattcgg    300
gattttctgg tttcgagtaa ttcgtataaa aggtttaaga tctattatgt tcactgaaat    360
cttaactttg ttttgtttcc agttttaact agtagaaatt gaaagtttta aaaattgtta    420
cttacaataa aatttgaatc aatatcctta atcaaaggat cttaagacta gcacaattaa    480
aacatataac gtagaatatc tgaaataact cgaaaatatc tgaactaagt tagtagtttt    540
aaaatataat cccggtttgg accgggcagt atgtacttca atacttgtgg gttttgacga    600
ttttggatcg gattgggcgg gccagccaga ttgatctatt acaaatttca cctgtcaacg    660
ctaactccga acttaatcaa agattttgag ctaaggaaaa ctaatcagtg atcacccaaa    720
gaaaacattc gtgaataatt gtttgctttc catggcagca aacaaatag gacccaaata    780
```

ggaatgtcaa aaaaaagaaa gacacgaaac gaagtagtat aacgtaacac acaaaaataa 840
actagagata ttaaaaacac atgtccacac atggatacaa gagcatttaa ggagcagaag 900
gcacgtagtg gttagaaggt atgtgatata attaatcggc ccaaatagat tggtaagtag 960
tagccgtcta tatcatccat actcatcata acttcaacct 1000

<210> SEQ ID NO 13
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0374 as found in Promoter Report #126

<400> SEQUENCE: 13
aagacacccg taaatgttgt catgtagaag aaactagaaa cgttaaacgc atcaaatcaa 60
gaaattaaat tgaaggtaat ttttaacgcc gcctttcaaa tattcttcct aggagaggct 120
acaagacgcg tatttctttc gaattctcca aaccattacc attttgatat ataataccga 180
catgccgttg ataaagtttg tatgcaaatc gttcattggg tatgagcaaa tgccatccat 240
tggttcttgt aattaaatgg tccaaaaata gtttgttccc actactagtt actaatttgt 300
atcactctgc aaaataatca tgatataaac gtatgtgcta tttctaatta aaactcaaaa 360
gtaatcaatg tacaatgcag agatgaccat aaaagaacat taaaacacta cttccactaa 420
atctatgggg tgccttggca aggcaattga ataaggagaa tgcatcaaga tgatatagaa 480
aatgctattc agtttataac attaatgttt tggcggaaaa ttttctatat attagacctt 540
tctgtaaaaa aaaaaaaatg atgtagaaaa tgctattatg tttcaaaaat ttcgcactag 600
tataatacgg aacattgtag tttacactgc tcattaccat gaaaaccaag gcagtatata 660
ccaacattaa taaactaaat cgcgatttct agcacccccca ttaattaatt ttactattat 720
acattctctt tgcttctcga aataataaac ttctctatat cattctacat aataaataag 780
aaagaaatcg acaagatcta aatttagatc tattcagctt tttcgcctga gaagccaaaa 840
ttgtgaatag aagaaagcag tcgtcatctt cccacgtttg gacgaaataa aacataacaa 900
taataaaata ataaatcaaa tatataaatc cctaatttgt ctttattact ccacaatttt 960
ctatgtgtat atatataccc acctctctct tgtgtatttg 1000

<210> SEQ ID NO 14
<211> LENGTH: 919
<212> TYPE: DNA
<213> ORGANISM: Arabidopsis thaliana
<220> FEATURE:
<221> NAME/KEY: misc_feature
<222> LOCATION: (1)..(919)
<223> OTHER INFORMATION: Ceres Promoter construct YP0377 as found in Promoter Report #127

<400> SEQUENCE: 14
tataaaccat tcctataaca ccatatttaa acataacaat gaattgcttg gatttcaaat 60
tcaaatatgt caactttttt tttttgtaag attttttat ggaaaaaaaa attgattatt 120
cactaaaaag atgacaggtt acttataatt taatatatgt aaaccctaaa aagaagaaaa 180
tagtttctgt tttcacttta ggtcttatta tctaaacttc tttaagaaaa tcgcaataaa 240
ttggtttgag ttctaacttt aaacacatta atatttgtgt gctatttaaa aaataattta 300
caaaaaaaaa aacaaattga cagaaaatat caggttttgt aataagatat ttcctgataa 360

```
atatttaggg aatataacat atcaaaagat tcaaattctg aaaatcaaga atggtagaca    420

tgtgaaagtt gtcatcaata tggtccactt ttctttgctc tataacccaa aattgaccct    480

gacagtcaac ttgacacgcg gccaaacctt tttataatca tgctatttat ttccttcttc    540

taactgattt ttcattaaca tgataccaga aatgaattta gatggattaa ttcttttcca    600

tccacgacat ctggaaacac ttatctccta attaacctta cttttttttt agtttgtgtg    660

ctccttcata aaatctatat tgtttaaaac aaaggtcaat aaatataaat atggataagt    720

ataataaatc tttattggat atttcttttt ttaaaaaaga aataaatctt ttttggatat    780

tttcgtggca gcatcataat gagagactac gtcgaaactg ctggcaacca cttttgccgc    840

gtttaatttc tttctgaggc ttatataaat agatcaaagg ggaaagtgag atataataca    900

gacaaaacaa gagaaaaga                                                 919


<210> SEQ ID NO 15
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0380 as found in
      Promoter Report #128

<400> SEQUENCE: 15

acaagtacca ttcactcttt ttacttttca atgtatacaa tcatcatgtg ataaaaaaaa     60

aaatgtaacc aatcaacaca ctgagatacg gccaaaaaat ggtaatacat aaatgtttgt    120

aggttttgta atttaaatac tttagttaag ttatgatttt attatttttg cttatcactt    180

atacgaaatc atcaatctat tggtatctct taatcccgct ttttaatttc caccgcacac    240

gcaaatcagc aaatggttcc agccacgtgc atgtgaccac atattgtggt cacagtactc    300

gtcctttttt tttcttttgt aatcaataaa tttcaatcct aaaacttcac acattgagca    360

cgtcggcaac gttagctcct aaatcataac gagcaaaaaa gttcaaatta gggtatatga    420

tcaattgatc atcactacat gtctacataa ttaatatgta ttcaaccggt cggtttgttg    480

atactcatag ttaagtatat atgtgctaat tagaattagg atgaatcagt tcttgcaaac    540

aactacggtt tcatataata tgggagtgtt atgtacaaaa tgaaagagga tggatcattc    600

tgagatgtta tgggctccca gtcaatcatg ttttgctcgc atatgctatc ttttgagtct    660

cttcctaaac tcatagaata agcacgttgg ttttttccac cgtcctcctc gtgaacaaaa    720

gtacaattac attttagcaa attgaaaata accacgtgga tggaccatat tatatgtgat    780

catattgctt gtcgtcttcg ttttctttta aatgtttaca ccactacttc ctgacacgtg    840

tccctattca catcatcctt gttatatcgt tttacttata aaggatcacg aacaccaaaa    900

catcaatgtg tacgtctttt gcataagaag aaacagagag cattatcaat tattaacaat    960

tacacaagac agcgagattg taaaagagta agagagagag                         1000


<210> SEQ ID NO 16
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0381 as found in
      Promoter Report #129

<400> SEQUENCE: 16
```

```
cacggtcaaa gtattgctaa catggtcatt acattgaaaa agaaaattaa ttgtctttac     60

tcatgtttat tctatacaaa taaaaatatt aaccaaccat cgcactaaca aaatagaaat    120

cttattctaa tcacttaatt gttgacaatt aaatcattga aaaatacact taaatgtcaa    180

atattcgttt tgcatacttt tcaatttaaa tacatttaaa gttcgacaag ttgcgtttac    240

tatcatagaa aactaaatct cctaccaaag cgaaatgaaa ctactaaagc gacaggcagg    300

ttacataacc taacaaatct ccacgtgtca attaccaaga gaaaaaaaga gaagataagc    360

ggaacacgtg gtagcacaaa aaagataatg tgatttaaat taaaaaacaa aaacaaagac    420

acgtgacgac ctgacgctgc aacatcccac cttacaacgt aataaccact gaacataaga    480

cacgtgtacg atcttgtctt tgttttctcg atgaaaacca cgtgggtgct caaagtcctt    540

gggtcagagt cttccatgat tccacgtgtc gttaatgcac caaacaaggg tactttcggt    600

attttggctt ccgcaaatta gacaaaacag ctttttgttt gattgatttt tctcttctct    660

ttttccatct aaattctctt tggctcttta atttcttttt gagtgttcgt tcgagatttg    720

tcggagattt tttcggtaaa tgttgaaatt ttgtgggatt ttttttattt tctttattaa    780

actttttttt attgaattta taaaaaggga aggtcgtcat taatcgaaga aatggaatct    840

tccaaaattt gatattttgc tgttttcttg ggatttgaat tgctctttat catcaagaat    900

ctgttaaaat ttctaatcta aaatctaagt tgagaaaaag agagatctct aatttaaccg    960

gaattaatat tctccgaccg aagttattat gttgcaggct                         1000
```

```
<210> SEQ ID NO 17
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0382 as found in
      Promoter Report #130

<400> SEQUENCE: 17

gcaaacaata atttatcgta agagtttttt taaaattcgt tggaacttgg aagggatttt     60

aaatattatt ttgttttcct tcatttttat aggttaataa ttgtcaaaga tacaactcga    120

tggaccaaaa taaaataata aaattcgtcg aatttggtaa agcaaaacgg tcgaggatag    180

ctaatattta tgcgaaaccc gttgtcaaag cagatgttca gcgtcacgca catgccgcaa    240

aaagaatata catcaacctc ttttgaactt cacgccgttt tttaggccca caataatgct    300

acgtcgtctt ctgggttcac cctcgttttt tttttaaact tctaaccgat aaaataaatg    360

gtccactatt tcttttcttc tctgtgtatt gtcgtcagag atggtttaaa agttgaaccg    420

aactataacg attctcttaa aatctgaaaa ccaaactgac cgattttctt aactgaaaaa    480

aaaaaaaaaa aaaactgaat ttaggccaac ttgttgtaat atcacaaaga aaattctaca    540

atttaattca tttaaaaata aagaaaaatt taggtaacaa tttaactaag tggtctatct    600

aaatcttgca aattctttga ctttgaccaa acacaactta agttgacagc cgtctcctct    660

ctgttgtttc cgtgttatta ccgaaatatc agaggaaagt ccactaaacc ccaaatatta    720

aaaatagaaa cattactttc tttacaaaag gaatctaaat tgatcccttt cattcgtttc    780

actcgtttca tatagttgta tgtatatatg cgtatgcatc aaaaagtctc tttatatcct    840

cagagtcacc caatcttatc tctctctcct tcgtcctcaa gaaaagtaat tctctgtttg    900

tgtagttttc tttaccggtg aattttctct tcgttttgtg cttcaaacgt cacccaaatc    960

accaagatcg atcaaaatcg aaacttaacg tttcagaaga                         1000
```

<210> SEQ ID NO 18
<211> LENGTH: 1009
<212> TYPE: DNA
<213> ORGANISM: Arabidopsis thaliana
<220> FEATURE:
<221> NAME/KEY: misc_feature
<222> LOCATION: (1)..(1009)
<223> OTHER INFORMATION: Ceres Promoter construct YP0388 as found in Promoter Report #131
<220> FEATURE:
<221> NAME/KEY: misc_feature
<222> LOCATION: (1005)..(1005)
<223> OTHER INFORMATION: n is a, c, g, or t

<400> SEQUENCE: 18

```
agaagtattc acgcacctta tatttgtagt gacatattct acaattatca catttttctc     60

ttatgtttcg tagtcgcaga tggtcaattt tttctataat aatttgtcct tgaacacacc    120

aaactttaga aacgatgata tataccgtat tgtcacgctc acaatgaaac aaacgcgatg    180

aatcgtcatc accagctaaa agcctaaaac accatcttag ttttcactca gataaaaaga    240

ttatttgttt ccaacctttc tattgaattg attagcagtg atgacgtaat tagtgatagt    300

ttatagtaaa acaaatggaa gtggtaataa atttacacaa caaaatatgg taagaatcta    360

taaaataaga ggttaagaga tctcatgtta tattaaatga ttgaaagaaa aacaaactat    420

tggttgattt ccatatgtaa tagtaagttg tgatgaaagt gatgacgtaa ttagttgtat    480

ttatagtaaa acaaattaaa atggtaaggt aaatttccac aacaaaactt ggtaaaaatc    540

ttaaaaaaaa aaaaagaggt ttagagatcg catgcgtgtc atcaaaggtt ctttttcact    600

ttaggtctga gtagtgttag actttgattg gtgcacgtaa gtgtttcgta tcgcgattta    660

ggagaagtac gttttacacg tggacacaat caacggtcaa gatttcgtcg tccagataga    720

ggagcgatac gtcacgccat tcaacaatct cctcttcttc attccttcat tttgattttg    780

agttttgatc tgcccgttca aaagtctcgg tcatctgccc gtaaatataa agatgattat    840

atttatttat atcttctggt gaaagaagct aatataaagc ttccatggct aatcttgttt    900

aagcttctct tcttcttctc tctcctgtgt ctcgttcact agtttttttt cgggggagag    960

tgatggagtg tgtttgttga atagttttga cgatcaccat tgcanctgg               1009
```

<210> SEQ ID NO 19
<211> LENGTH: 1026
<212> TYPE: DNA
<213> ORGANISM: Arabidopsis thaliana
<220> FEATURE:
<221> NAME/KEY: misc_feature
<222> LOCATION: (1)..(1026)
<223> OTHER INFORMATION: Ceres Promoter construct YP0396 as found in Promoter Report #133
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (1022)..(1022)
<223> OTHER INFORMATION: n is a, c, g, or t

<400> SEQUENCE: 19

```
ccagtcgant tggcatagta aaagtgaatt taatcatact aagtaaaata agataaaaca     60

tgttatttga atttgaatat cgtgggatgc gtatttcggt atttgattaa aggtctggaa    120

accggagctc ctataacccg aataaaaatg cataacatgt tcttccccaa cgaggcgagc    180

gggtcagggc actagggtca ttgcaggcag ctcataaagt catgatcatc taggagatca    240
```

```
aattgtatgt cggccttctc aaaattacct ctaagaatct caaacccaat catagaacct    300

ctaaaaagac aaagtcgtcg ctttagaatg ggttcggttt ttggaaccat atttcacgtc    360

aatttaatgt ttagtataat ttctgaacaa cagaattttg gatttatttg cacgtataca    420

aatatctaat taataaggac gactcgtgac tatccttaca ttaagtttca ctgtcgaaat    480

aacatagtac aatacttgtc gttaatttcc acgtctcaag tctataccgt catttacgga    540

gaaagaacat ctctgttttt catccaaact actattctca ctttgtctat atatttaaaa    600

ttaagtaaaa aagactcaat agtccaataa aatgatgacc aaatgagaag atggttttgt    660

gccagatttt aggaaaagtg agtcaaggtt tcacatctca aatttgactg cataatcttc    720

gccattaaca acggcattat atatgtcaag ccaattttcc atgttgcgta cttttctatt    780

gaggtgaaaa tatgggtttg ttgattaatc aaagagtttg cctaactaat ataactacga    840

ctttttcagt gaccattcca tgtaaactct gcttagtgtt tcatttgtca acaatattgt    900

cgttactcat taaatcaagg aaaaatatac aattgtataa ttttcttata ttttaaaatt    960

aattttgatg tattacccct ttataaatag gctatcgcta caacaccaat aacccattgc   1020

anctgg                                                              1026
```

<210> SEQ ID NO 20
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0337 as found in Promoter Report #143

<400> SEQUENCE: 20

```
taattttttt atttttggaa ctaacactta ttagtttagg tttccatcac ctatttaatt     60

cgtaattctt atacatgcat ataatagaga tacatatata caaatttatg atcatttttg    120

cacaacatgt gatctcattc attagtatgc attatgcgaa aacctcgacg cgcaaaagac    180

acgtaatagc taataatgtt actcatttat aatgattgaa gcaagacgaa aacaacaaca    240

tatatatcaa attgtaaact agatatttct taaaagtgaa aaaaaacaaa gaaatataaa    300

ggacaatttt gagtcagtct cttaatatta aaacatatat acataaataa gcacaaacgt    360

ggttacctgt cttcatgcaa tgtggacttt agtttatcta atcaaaatca aaataaaagg    420

tgtaatagtt ctcgtcattt ttcaaatttt aaaaatcaga accaagtgat ttttgtttga    480

gtattgatcc attgtttaaa caatttaaca cagtatatac gtctcttgag atgttgacat    540

gatgataaaa tacgagatcg tctcttggtt ttcgaatttt gaactttaat agtttttttt    600

tttagggaaa ctttaatagt tgtttatcat aagattagtc acctaatggt tacgttgcag    660

taccgaacca attttttacc cttttttcta aatgtggtcg tggcataatt tccaaaagag    720

atccaaaacc cggtttgctc aactgataag ccggtcggtt ctggtttgaa aaacaagaaa    780

taatctgaaa gtgtgaaaca gcaacgtgtc tcggtgtttc atgagccacc tgccacctca    840

ttcacgtcgg tcattttgtc gtttcacggt tcacgctcta gacacgtgct ctgtccccac    900

catgactttc gctgccgact cgcttcgctt tgcaaactca aacatgtgtg tatatgtaag    960

tttcatccta ataagcatct cttaccacat taatttaaaa                         1000
```

<210> SEQ ID NO 21
<211> LENGTH: 1013
<212> TYPE: DNA

<213> ORGANISM: Arabidopsis thaliana
<220> FEATURE:
<221> NAME/KEY: misc_feature
<222> LOCATION: (1)..(1013)
<223> OTHER INFORMATION: Ceres Promoter construct YP0384 as found in Promoter Report #144
<220> FEATURE:
<221> NAME/KEY: misc_feature
<222> LOCATION: (1009)..(1009)
<223> OTHER INFORMATION: n is a, c, g, or t

<400> SEQUENCE: 21

```
tttaaaaaat tggataacaa caccgataaa aattcacatt tgcaaatttt attcagtcgg     60

aatatatatt tgaaacaagt tttgaaatcc attggacgat taaaattcat tgttgagagg    120

ataaatatgg atttgttcat ctgaaccatg tcgttgatta gtgattgact accatgaaaa    180

atatgttatg aaaagtataa caacttttga taaatcacat ttattaacaa taaatcaaga    240

caaaatatgt caacaataat agtagtagaa gatattaatt caaattcatc cgtaacaaca    300

aaaaatcata ccacaattaa gtgtacagaa aaaccttttg gatatattta ttgtcgcttt    360

tcaatgattt tcgtgaaaag gatatatttg tgtaaaataa gaaggatctt gacgggtgta    420

aaaacatgca caattcttaa tttagaccaa tcagaagaca acacgaacac ttctttatta    480

taagctatta aacaaaatct tgcctatttt gcttagaata atatgaagag tgactcatca    540

gggagtggaa aatatctcag gatttgcttt tagctctaac atgtcaaact atctagatgc    600

caacaacaca aagtgcaaat tcttttaata tgaaaacaac aataatattt ctaatagaaa    660

attaaaaagg gaaataaaat attttttaa aatatacaaa agaagaagga atccatcatc    720

aaagttttat aaaattgtaa tataatacaa acttgtttgc ttccttgtct ctccctctgt    780

ctctctcatc tctcctatct tctccatata tacttcatct tcacacccaa aactccacac    840

aaaatatctc tccctctatc tgcaaatttt ccaaagttgc atcctttcaa tttccactcc    900

tctctaatat aattcacatt ttcccactat tgctgattca tttttttttg tgaattattt    960

caaacccaca taaaaaaatc tttgtttaaa tttaaaacca ccattgcanc tgg          1013
```

<210> SEQ ID NO 22
<211> LENGTH: 995
<212> TYPE: DNA
<213> ORGANISM: Arabidopsis thaliana
<220> FEATURE:
<221> NAME/KEY: misc_feature
<222> LOCATION: (1)..(995)
<223> OTHER INFORMATION: Ceres Promoter construct YP0385 as found in Promoter Report #146

<400> SEQUENCE: 22

```
actcaagcaa taggacaagc aaaattccaa ttattgtgtt actctattct tctaaatttg     60

aacactaata gactatgaca tatgagtata taatgtgaag tcttaagata ttttcatgtg    120

ggagatgaat aggccaagtt ggagtctgca aacaagaagc tcttgagcca cgacataagc    180

caagttgatg accgtaatta atgaaactaa atgtgtgtgg ttatatatta gggacccatg    240

gccatataca caatttttgt ttctgtcgat agcatgcgtt tatatatatt tctaaaaaaa    300

ctaacatatt tactggattt gagttcgaat attgacacta atataaacta cgtaccaaac    360

tacatatgtt tatctatatt tgattgatcg aagaattctg aactgtttta gaaaatttca    420

atacacttaa cttcatctta caacggtaaa agaaatcacc actagacaaa caatgcctca    480

taatgtctcg aaccctcaaa ctcaagagta tacattttac tagattagag aatttgatat    540

cctcaagttg ccaaagaatt ggaagctttt gttaccaaac ttagaaacag aagaagccac    600
```

```
aaaaaaagac aaagggagtt aaagattgaa gtgatgcatt tgtctaagtg tgaaaggtct    660

caagtctcaa ctttgaacca taataacatt actcacactc cctttttttt tctttttttt    720

tcccaaagta cccttttttaa ttccctctat aacccactca ctccattccc tctttctgtc    780

actgattcaa cacgtggcca cactgatggg atccaccttt cctcttaccc acctcccggt    840

ttatataaac ccttcacaac acttcatcgc tctcaaacca actctctctt ctctcttctc    900

tcctctcttc tacaagaaga aaaaaaacag agcctttaca catctcaaaa tcgaacttac    960

tttaaccacc aaatactgat tgaacacact tgaaa                               995
```

```
<210> SEQ ID NO 23
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0633 as found in
      Promoter Report #153

<400> SEQUENCE: 23

ttaatctgag tcctaaaaac tgttatactt aacagttaac gcatgatttg atggaggagc     60

catagatgca attcaatcaa actgaaattt ctgcaagaat ctcaaacacg gagatctcaa    120

agtttgaaag aaaatttatt tcttcgactc aaaacaaact tacgaaattt aggtagaact    180

tatatacatt atattgtaat tttttgtaac aaaatgtttt tattattatt atagaatttt    240

actggttaaa ttaaaaatga atagaaaagg tgaattaaga ggagagagga ggtaaacatt    300

ttcttctatt ttttcatatt ttcaggataa attattgtaa aagtttacaa gatttccatt    360

tgactagtgt aaatgaggaa tattctctag taagatcatt atttcatcta cttcttttat    420

cttctaccag tagaggaata aacaatattt agctcctttg taaatacaaa ttaattttcg    480

ttcttgacat cattcaattt taattttacg tataaaataa aagatcatac ctattagaac    540

gattaaggag aaatacaatt cgaatgagaa ggatgtgccg tttgttataa taaacagcca    600

cacgacgtaa acgtaaaatg accacatgat gggccaatag acatggaccg actactaata    660

atagtaagtt acattttagg atggaataaa tatcataccg acatcagttt gaaagaaaag    720

ggaaaaaaag aaaaaataaa taaaagatat actaccgaca tgagttccaa aaagcaaaaa    780

aaaagatcaa gccgacacag acacgcgtag agagcaaaat gactttgacg tcacaccacg    840

aaaacagacg cttcatacgt gtccctttat ctctctcagt ctctctataa acttagtgag    900

accctcctct gttttactca caaatatgca aactagaaaa caatcatcag gaataaaggg    960

tttgattact tctattggaa agaaaaaaat ctttggaaaa                         1000
```

```
<210> SEQ ID NO 24
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0564 as found in
      Promoter Report #156

<400> SEQUENCE: 24

aacaaaatag tcccgcaggt taaaacctag tattttacaa aaatatagac aaataaaata     60

aaaatgaact atcgtggatt tagttagaga aatccataca aaaataaatt gcattgagaa    120

actttagatg acgactaagt aatataagat tttgcattga gaaagcttac atgtcaccct    180
```

```
aatttctatc aaaagggttt ctgatactaa ttggaaccat gtgagaaact atccatagaa    240

atgatgatct tatctagtta tcatgagctg atgactttga atattccaca gtcactaaac    300

gcatgtttat ttctcagctt tatgaatctg tatgtagaca cactttcgta ttttcttcac    360

ttttgtgtat ttgtattgcc cattcctctt ttaccaacca ataaaaaaag cagtcttttt    420

tttgtttggt caagcattgg cactctttgt caatcaatta cccaagggat atataataat    480

aaattggaat aatgaaagta gttcatcata aggttcgtga ttattaactt ctacttttgt    540

ttatattcaa tagattaaga tgccgtgtat gataaggaga gcaaaagtaa tccgatagag    600

atcacagcaa tattcattac aaaatagttt tcaaataaaa acacatgatc aaaaagtgac    660

tcacaaaaac acatgatacg tacgtgggat gctaatccta aagcaacaag gccacaaggg    720

caaaatatgt agctttcatg ctttggcaaa gcgaaaactc tagttaagct tacctaacag    780

aaaaaataac ccccaaaaaa gcgttacgtt ccaaacattt agacagggta cacgtgaatg    840

actcccactt tttttaaaaa aataatagta ctatcaattc aaatgtgtaa acaacaaaaa    900

aaaaaaatgt gtaagtaacg tctgtaattg atttgataag ataaaaaaat cttgattaat    960

ttttctataa attgaagcct ttcctcttta catttcgtta                          1000
```

```
<210> SEQ ID NO 25
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0569 as found in
      Promoter Report #158

<400> SEQUENCE: 25

gagtcaaaaa atgaattaaa taaaacggtg taatcttaaa ctgtctttag cacgttacga     60

tgaaatttca attttcgact aatctttgac cctaaacaat aggtaaccac cgtcaccgta    120

ttaaatgctt tttctattct aagaaataca gataagtttc cacgtattgt attcgtccca    180

caaatattca taaggaggaa ataatatcct ttttttatag aagcaaatgg aaataatgtg    240

aacaaaaatc caagatctat tacaaaataa aatattttaa aaatttagga aagacaatcg    300

atattattag cagtttagtc cgaaaaatgc cgaaatacac tcaatcatag agatattact    360

tttattatta ccaattttga cacaaatcaa ttgttaaaac ttcctaaaaa gtaaaattct    420

ctaattgaat atataaataa aatatttcaa atgtgatttt tatttacaaa ctttacaaat    480

gttaataata tattcaccta aactgaaaac atctaaatgt cataaaattt gtatcttatt    540

cctaattctg attttttttt aatataaagt tataaacaca attagtagat aatctcatta    600

ttcataatta tggattattc ggcgattttc actattgttt ttcaccacta attatgccac    660

cttgccagct gtattcacac acacacacac actctacaca agcaaaactt aaagtatgca    720

tttttattaa ttatggttca tccattttat tacagaagaa taaatatttc atttgaatga    780

gaataataaa taaaaaggca atgcttttat gatcctctta cctttaatct tcttcgtctc    840

tctatcttcc tcgatctccg ccgattcctt cgtctttccc tttcctctct gtaaaccttt    900

tcttcttctt cttcttcaat gcctccctaa aaccctagac tcagaattct caaaggcgac    960

acctttaacc tcctccactc tgtttctttc tccaacaaaa                          1000

<210> SEQ ID NO 26
<211> LENGTH: 996
<212> TYPE: DNA
<213> ORGANISM: Arabidopsis thaliana
```

<220> FEATURE:
<221> NAME/KEY: misc_feature
<222> LOCATION: (1)..(996)
<223> OTHER INFORMATION: Ceres Promoter construct PT0650 as found in Promoter Report #168

<400> SEQUENCE: 26

```
catacttaat tctaaaaaaa caacacttat agtttataag cagctcttat gataaaaatc     60
tttctgagtt atagctctgt taaacttgta ttcaccccaa aaacggatgt ttcatttctt    120
attttttact tggagtattt tattgtaatt tgtaaaaaaa aatgtaaagt gggggatatc    180
atgaaaaaca acgtcacttt gtttggtcac aatatacatt tgataaaata atggtcgtcg    240
cgtgatttag ttgatttttg ttttatcaac cacgtgtttc acttgatgag tagtttatat    300
agttaacatg attcggccac ttcagatttg ggtttgccca catatgacat accgacatag    360
aaggttaaat ccacgtggga aatgccaata ttcaatgttt ggttttcaaa agagaatcat    420
ttctttatat gatctcaaaa gtatggaatt gaaatgacta atgagcacat gcaattggtg    480
ctatcttaaa aaccgaacgt ctttgaattt aatttgtttt tcaccaaagg tacctaatga    540
aaccctttca ttaaaaaata aaggtaacaa acaaaatttt gtattggaaa aaacattttt    600
tggaatatat aatttggtaa tagaattatg agcaaaaaag aaaaagaaaa gaaagaataa    660
tgagcataat aaagccttta cagtattact aattgggccg agcagttttg ggctcttgat    720
catgtctagt aatcttaaac agacgataaa gttaactgca atttagttgg ttcaggtgag    780
ctaccaaatc caaaaatacg cagattaggt tcaccgtacc ggaacaaacc ggatttatca    840
aaatccttaa gttatacgaa atcacgcttt tccttcgatt tctccgctct tctccactct    900
tcttctctgt tctatcgcag acatttttgt ttgcatacat aataataata cactcttgtc    960
aggatttttg attctctctt tggttttctc ggaaaa                               996
```

<210> SEQ ID NO 27
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct PT0659 as found in Promoter Report #172

<400> SEQUENCE: 27

```
tataataatc ataaaacaag agttgatcaa gtaacatata cataattttg atatagacac     60
catctaaaag cggccggaat atgtaattta gaaattttgt tagtattttt agaatccaag    120
atcgtacata tgtaaatcaa aaacatcact tctatggttc acataattat aaattaataa    180
tttgtacggt ttgaccgcat ctattatata tataaaaaaa tgtctaacat atcccaaatg    240
agaagcatct cgagctattt ataaaatact atacaaattt taaaaatcag taagtacact    300
tgttgttatt aagaaaataa tgatcctaag taactcgtcg acatattcaa ttttggcaac    360
tactttcttg aagcaaacaa aattataagc tagtatcaac aaacatatgg atcatttaag    420
cttcgataag cggtcaacat atgggggaat taggagacaa atcactactt aaaaagaacc    480
actagtcatt actttttgtg gataacatga caatcactac aataaaaact gggcccatca    540
agcccaagaa tactcttaat gacaagtcaa aagagagata gttttgagtt ttgactcctc    600
ggacgaatcg caagactggt cttgtccccc tttcgagttt cccgggaaac ttcctccttc    660
ctctaatctc tctacagttc tcaatttctt gcttcttctc tcacgcttag caattatacc    720
caatcccatt tgaatattac tcttcgccaa catgtcctta aattatctct ttttaatgaa    780
```

```
ttgatcgata aagttctcac ctttatgcct cctcctactt tttccactta atcatcccac    840

ttcctcttca gatgtaagca atgttgtcta gagtcctcct ctgattcaga tttcgttgct    900

gaatcttttg taaaactctg ttctttgtat gtcgagaagc caaattcagg gaatttaggg    960

ttttacaaaa aaataaaaaa gagtttcttt ttttggatg                           999


<210> SEQ ID NO 28
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0684 as found in
      Promoter Report #177

<400> SEQUENCE: 28

tagctagatt tctatataaa cagaagaaag ttaaaaagca aataaaaatt cacaaataga     60

aatcgaacaa aaagctatga aaatataaat accataacct tatggaaaaa cgatgaaatg    120

cttaacaaaa aaaactttgg caatggcatg catgtgcctg taacagaagg cccccataag    180

ctgttagtga tatacaactt aagcaaatgt gcactcttca cgcacttccc gcttttctaa    240

atttcaattt atttgtctac atttttgtcc aaattattga tataattcta ccacgacttc    300

ccccacatgt ccctccaaag agatccgtac tacacagtct accgacagca catgcatgga    360

ttttccaaac catcttcttt aaggataatc cttgacattt ttaatattaa aaaaataaca    420

aaaaattcaa tatataaata acatcctaaa tctatgtttt ggtagaaaac aagttctaaa    480

gttcacattt ggacagtggt tagtacttgg taatcaaaat atttgtttaa gaatcttgac    540

tacttactta gtctaaaccc taacgtacat ggttagacat attagacaca attctattct    600

atagcttctt aacaaacgtt tagcataatc cgaaattggt tttaccaata tttattaccg    660

tacgtgtgtt tttttctgta agaaaggaaa aaaagccaac tcatgattct tctgatattg    720

catgtaatat atttgccaaa taagcttacg acacaaacac aatgacacta tgacagtaag    780

atatcatttc aaaatacgga tatacccccca aattggtggc aatgacaaag aaaaaaagag    840

ttcttcacag tggcacattc gtaatacata tgaactttgg tggttgtttc gtaatataga    900

tcgtacttaa aacctctaaa caccgttctc tttatttgcc atcttcttca ttatcatcat    960

ctccatctct ctctctctct ctctcatttt cttgaaaaag                         1000


<210> SEQ ID NO 29
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0655 as found in
      Promoter Report #179

<400> SEQUENCE: 29

aaatcaatat taatactaaa atttaaacta catttaagtt tgaatctcta aagcttgtgt     60

taatggatag cttggaaagc ttatctttcc ggagaacatt attattgtac aatctattag    120

ctcttgattc ttgaatttag ttagtgcatc tcctgattat gttccacttt cattttcttc    180

taattttagg aatctggatg caaatccagg ttaagtacat ttagcttaat agaaagatga    240

tttgactcgg actgatgaaa atggtgccaa gaccaaaact ctaccactcg gacgagtcag    300

gtcaaaaaca actcaaattg actattgaac catttttcta atctagacca gacaccaaaa    360
```

```
ctctaccaca gctctccgac attggtgggc ctaataaatt cccacaaata ttttttctg    420

ttttcttttt ctataaacgg ttggaattac atcttttgaa cccatatttt tttttgtact    480

aaaatgatta aactcgagcc aaaaaaatat caatttatta ggcaatcact acttgtataa    540

tgcaatttat ggcgtgatta gttccacaac tgcatataga ctatcgaata cttacacttt    600

tatgttttta ggaatgtgag tttggagttt gttaccgaaa aaccaatcaa gttcaagctt    660

aaagccttaa accaatcaaa ccatatcact ttctattttt aggaatgtgg atgcaaatca    720

acattaaata catttagttt ctaaaaccaa tgttaccggt tttgataatt cccacaaata    780

ataagatgtt cataaaaacg tggccaacaa ccatttatgt tcaccaacct aatcgcccct    840

ctctcaaaaa aaaaaaaatc caattttcca attttattta acggtcacat tttcctcatt    900

gcctaattaa aaacattcag acacaaattt agtttcttct tcttttggtt ctgtctgaat    960

ccaattttct tatattttat ttcctccacc accgtgagat                         1000
```

```
<210> SEQ ID NO 30
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0656 as found in
      Promoter Report #180

<400> SEQUENCE: 30

caatatcaca ataatctttc taagttatga aaagaacgtc tactactatt tgtttaaaac     60

tacataggac aacatcaaat cagttttgaa attcattgta aaattctttt aatactaaaa    120

ttgtttacag ttaatgagaa attacaatat tatttttagc agattataat tagaaaatac    180

attattatta ttgatcaatt taccttgcag ttccacgcaa aaccaacaaa ataacaaata    240

acaaagcatt gtgtggaatg acgtaaggat gagtcagcag acaaggagtg agatcgaatc    300

gggtcaagat tatctggttg ggacccgtca catgcacatg gaccctctcc cgtacctaat    360

ccaggttaaa taatcttgat tttctgttta attaccttaa aaacacatta ttattgaaac    420

taataataaa tctcggatct ttggttccga ccatacttgc gaaagatcat tgctttaatg    480

ctaatgtttc tctaattttg atattccttg agattagatt ccctttgcat tgtcttttct    540

tgttaatttg ttagggttca tattcttaca ttattttttt tggcaaagaa aaaaacattt    600

ataaacatat ctaattcgag cctgatctat taatgggtca aataaaagcc tctttggccc    660

aattcaataa actggccaac tggggatcat catagagaca gactactaga gagtagagac    720

gcatcagaaa gaagagaaat tgatcccaca agtttaaaca cgattacaaa ttaaaacgtg    780

ccacgtattc aagacggtga attaacacga cgtggcaagg tatgattgga taacttacgc    840

agctgcctaa caaaaacaag tgatttgagt tttcagatga ttagaaggaa aaaaaattct    900

ggaactttcg agcttctgtt ttgcggtgct ctcaaagctt atatcggatc tcgaatcttg    960

aatcggactc agaacctcgg atcttcgaaa atcgacgaac                         1000
```

```
<210> SEQ ID NO 31
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0657 as found in
      Promoter Report #181
```

<400> SEQUENCE: 31

```
gtttatgcgt ttgatttttg gttctataca gatctctcta tctcttttat gtaatttttg     60
tattcatgga tttcatacag ttcaagttaa gcaaacttac tttgtaataa atgtaccatt    120
gttgttgaga ttatcaataa tcgaatagct ttcttctcta aattttagtc aactaaacaa    180
gtctgttcat tgataaactc atttagataa atttgtggat tttgaaattc tggtaaccaa    240
aagattatgg tttgctacgc gctaatactg gtgattgatt acggcacaaa agagcccagt    300
aaataattat tggcccagtt tagttttggg ccttatgggc caatattatc atcgagcatc    360
caacggtagt gatggagatt tctttatgga atatctgata tccaccgtta gattaagaga    420
cgaggttggc tccgaatagc atatagttaa agggcaaaac cctgcgccgc ccgcgtctct    480
cctctctctg tttcttttct ttttgtttca ttttcttatc tcctcacact cttcgaacaa    540
ggaagaaccc taatctcaag gtaaattcat tatcactgta attttccttt ctattagtgt    600
tttatctctc cggttctagg gtttctctaa tccccgattt tgcaaaatgt cagatatctt    660
tctttcttga ttcatttcgc ttctttctgt agataggatt agtttttgtc ggtgtttggg    720
aatttactgg gttttcaact tctctgtgtg tttgattggg ggatttggta tacctaatcg    780
attgaaaatg attaaattta ggttaaaact actagtcaca tcaccgtgtc ttcatacgca    840
tctgagttta aatctgttcg cgcttacttt cttctcacta gtttcttgta taataagaag    900
tttttgtgaa tgtattatta gcagttaatg tgttcattga ttcttttgga agtgatttgg    960
ggattgatgg attttgcttc ttattatggt ttatacacag                          1000
```

<210> SEQ ID NO 32
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0660 as found in Promoter Report #186

<400> SEQUENCE: 32

```
caagtcaagt tccaatattc taaggagaaa taatagtata ctaaacatac attagagagg     60
ttaaacttct ttttggattt aagtgtgtat gcataggcta tttattctta agtataacta    120
ttaactgtag ctagatttat acaagaaata cataaaactt tatgcatgtg aggtagccat    180
gaatatacgt acatgttgca atcgattata catgttgtat ttggatttct ctatacatgt    240
tttaacttgt cattctctaa gtatatacat accattaata ctgtgggcat gagtttatga    300
taagactttt cttttggaga ccagttttgt tttcctttcc acctatattt gtctataggc    360
ttcacggtac actagtttac aagtgttttt atatgttcta aataaaattg agattttccg    420
gaacggtatg atctgtttgc aaataaggac gtatatataa cagtatcaaa tatatttgtt    480
gttataaggc aataatatat tttctgagat attgcgtgtt acaaaaaaga aatatttgtt    540
aagaaaaaaa aagatggtcg aaaaagggga gtaggtgggg gcggtcggct tttgattagt    600
taataaaaga aaccacacga gtgacctacc gattcgactc aacgagtcta ccgagctaac    660
acagattcaa ctcgctcgag cttcgtttta tgacaagttg gttttttttt ttttttttta    720
attttttcat cttcttgggt ttggttgggt cactcttcag gtcaggtgtg taaaaaaagaa    780
agaaagaaaa gagagattgt tgtgttgtaa ccccttttgac taaaatctaa tgaacttttt    840
taacacaaca aaactccttc agatctgaaa gggttcttct tctctcttag tctctttgtc    900
```

```
cttttattct ccgtcgtcgt ttcatgatct gactctctgg tcttctcttc ttcttcttct    960

tcttctattt tttcttactt cgtcactgtt gtgtctgaac                          1000


<210> SEQ ID NO 33
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0679 as found in
      Promoter Report #203

<400> SEQUENCE: 33

taagaaaaac tgtaggcttg ttgtcagaac aaacatggac ccatgttctc tatgtcccta     60

agatgtgtac caatctcaat tcacttcttt tgttgcacta ttttttaaaa aataactttt    120

attttatatt ttgagatctc cattgcccct gctgcactag acattacagc tcatttttttc   180

cttataattc aatccctagc tatttttctt tcttattagt ttaaactaat catatttggg    240

taattagcgt tgaaactatc tatcatatca attttaatga tacatatgca atactttatg    300

tgagtatatg catgtatgca tgttccaaca tccagattaa tgactaacgt ttaagccctg    360

attttttcag agaaattttg tgttgtacct atgtttgtat tacacacaat atttaccatt    420

gtttaacatg tacacatgtg tttataaatc tccgtacact ataatgcata tttgaaccat    480

atatgacaga aagttttcca ctagttctaa ttacattttg ttgccctttc ctactcgtct    540

attgcctata gaaatattat tttagttatg attaagaatt gggatgcaca ttccgaaatt    600

aattattaaa tgccactatg aagaaccctt gaacatagtc taattcaatt ttaagatcat    660

aaggaacatt aacagtgaca atagctaagg tctctcgaca atgagacaat ccgcttttta    720

aatatataca tataagagat accatattgt atacatatgc agatacaatt acaacttgac    780

caaatttatt caatttctcc ttctctttat atcaataaga aactattcat gatactggac    840

cagcctgttt gaatcttgtc ccatccacaa atctcccaat atataaataa agaaccttca    900

cccgtaaaac caaaaccatc aacaacttca aagctttcta agcaagagat tgagagaaat    960

cggattttct ttctaagact caaaatatct aaaaacaata                          1000


<210> SEQ ID NO 34
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0678 as found in
      Promoter Report #178
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t

<400> SEQUENCE: 34

aattaaatga aacncgcccc taaattagga gggatttggg taagtggtaa cacattcact     60

ggaaacatgt gaagaaagga ggatgtcaag tagctgaaaa ctcagtatag taaccaacgg    120

cttctcacca acctttcatt aataatttgg tcatccctat atttttattc aacattttgt    180

ttttcaatag cttagagcac cttaatacct ttcagtgttt ttttataaaa aaaancaaaa    240
```

```
attgggatta atcatcaatc cccaaatgta acgtttactt agattatgtt catttttcta    300

tacacacaaa tcatattctt ttgttttaat cttcgaaaaa cgagaggaca ttaaataccc    360

ctaaaaaagg aggggacatt actaccaacg tacattaaca tgtttgatag caaacgattt    420

attttgttcg ttttgaaaag gggaaagtaa tgtgtaaatt atgtaaagat taataaactt    480

ttatggtata gtaacatttt cgaataataa gagagggaaa acactcgcca ttgtcggcaa    540

tttagaacca atattagaag ggttttttta gagaaaaagg acttaaaagt ttagagacct    600

taacaacaac ttatttagaa atagacatgc ttaagttgac aacagcgagt ttattttcta    660

tatcgaagaa aaatacgaac tttttcttaa ttagatttcg aatgcatgca ctatcgagaa    720

tcgaccgtca caagaaaaaa ctaatataca tactgtacat atctatattc aatattggtg    780

gggatgggtt taatgtgtat ttataattca tggataaatt cacacaataa ggtccatgaa    840

actagaaggt accaaaaata agcattaatg actctttgcc acttatatat atgattctct    900

catagtacca ttttattctc ccaaacctat cttcttcttc ctctcttgtc tctctcgctc    960

tctctcttct acattgtttc ttgaggtcaa tctattaaaa                        1000
```

<210> SEQ ID NO 35
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0623 as found in Promoter Report #161

<400> SEQUENCE: 35

```
aaagttattg acattttgaa aggaccgtaa atattaccaa aaaactgacg gagttaggat     60

cggccacgta gaaagggaca aagagagaac agtcacggac tcggccagac taagtatggg    120

cctgtctgaa tccaaactca gctaagttcc aaaagcataa agagagatgt gtaatgaaat    180

gaacgtattc tagaaacgaa agcaatgtta tgctttgttt ttgagccaca tgtttttggg    240

agatggagag aatctttttt acgtttttaa cctaacccac ttggcacttg gccaaaaaag    300

tgagaagaaa ctgtggcgaa tgagtaggcc acgccatgga ctttgttcct tgtccttcaa    360

aagttaaatt tatgttatgc gtggggacaa tctaagcaac gtggttcctt taaatatcgc    420

agcttcctct tttacacttt tggagcctac gtgttttgtt ttggaccggc caaatacacg    480

agtcagtcag tttagaaata atttggatgt ccaaaaatct tggagatcca aataaaataa    540

ttagcatgtt ttagttcata agaatatgaa atgtagataa actgtctata ttaatttttc    600

catagaattg gctttttatc gaggtgatgt acttaatgac tttgttgatt actactcgta    660

taacaataaa gaatatgata ctatgtgaga cttataatga atttggtgtg tgttaattaa    720

tccagttgaa acagtttaat aacaaatcag aataaaaatt gtagtaagaa aatttgaacg    780

ctgatccttc aacctagata gtgaaccttt caaatactat atgattcacg tgtaatgttt    840

ttgaccgttg gttatttttg tgtgaactat attaacttat caatatcgaa aggctaaata    900

agtaaataac taaaagaaag ttcaggaaac aactcgacct aatgacctat catttctgat    960

cacccgtcct ataaatacat acgtaagatc attcgttact                        1000
```

<210> SEQ ID NO 36
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0613 as found in
Promoter Report #163

<400> SEQUENCE: 36

```
ttaatactaa cattgtagaa agccacaaaa aagaaattga aatgtgagta gatgctgagt     60

cagaggtttg gtcaatacac aacagctaat tgagataata ttatacacgt cacgatgact    120

tgttttttct cctcccaact tgttaatttc tttattctta aaattaaacc atcgcaaaaa    180

cagaagaaca cagctgtttt tctcgactcc caatttctat tttgctgcta aggacatttc    240

atttcattat ttcccaattc aggactcctt agattttcct aaatttgttt tcctaacttg    300

ctctctctca ttctaacatt ttctcatttt tttagattat cttgtacttt ttagtagatt    360

attttatcag gttttacaaa catacattga cattctaaaa agggcttcta aaaattcagt    420

gtggaatgct gatatactaa aaaaaggtca tgcaaaatta tctacgattt atctaaaatt    480

agataatttg ccatatataa ctattaacta ataatcgatc ctttgatttt ttgtttagat    540

aaaacgaaac agctatatct tttttttttg ttatcggatt ttaatcgaat aaaagctgaa    600

aaataacagt tatatcttct tctttttttaa ctaatgaaac agttatatct taaacaaaca    660

acagaaacag taaaatatta atgcaaatcc gcgtcaagag ataaatttta acaaactaat    720

aacaattgag ataagattag cgcaaaagaa actctaattt tagagcgtgt aaacacaaac    780

acgtcttgaa agtaaacgtg aattacacgc ttctaaaacg agcgtgagtt ttggttataa    840

cgaagatacg gtgaagtgtg acacctttct acgttaattt cagtttgagg acacaactca    900

agttatgttt gatatctaag gacttgcact gtctccaaat ctgcaggaag gactttttga    960

ttggatcaat ataaatacca tctccattct cgtctccttc                         1000
```

<210> SEQ ID NO 37
<211> LENGTH: 669
<212> TYPE: DNA
<213> ORGANISM: Arabidopsis thaliana
<220> FEATURE:
<221> NAME/KEY: misc_feature
<222> LOCATION: (1)..(669)
<223> OTHER INFORMATION: Ceres Promoter construct PT0848 as found in
Promoter Report #190

<400> SEQUENCE: 37

```
tctctttaaa tcagttaact aaccgtttat atatttacga taaggtttga agagattatt     60

gataaaataa tacatttcat aatcccgcgt tcaaccgttt aaagtaacat ttaagttgac    120

tatatctaat tttttttcca ttaaatatgg agctggtaaa ctttatcaac ttctaaaaag    180

tgtaacaaca aaaattaggt caatcacaat tctgtttttt ttattatttt ggattgactt    240

ccaattgcaa atagtcttag tgatcaccat tatcatacat atatacatca agtaggtttc    300

atcatgatat accacaaagt atttgacaag ccatatggtt ttggatcaaa aagtcggtcc    360

aaaattaatg ttttatgtgc aagaaccgac ccattgtaca cacgtgttaa catcttcaag    420

actttcatct ctatttttct tttggtcatt aagataccca ttgatccgaa tctgttacat    480

tcccacctac ttttttaatt tttactatcc actccaaatt aaacacaacc gatgatttta    540

ataattggaa gcttttaaaa atatttcaaa acaagcctct ttgtgtttgt ctatatatat    600

acacgtaata agaaggtgaa tgaatctcac agcttacttg ttctaaggct tccaataacg    660

aaaacagta                                                            669
```

<210> SEQ ID NO 38
<211> LENGTH: 623

```
<212> TYPE: DNA
<213> ORGANISM: Arabidopsis thaliana
<220> FEATURE:
<221> NAME/KEY: misc_feature
<222> LOCATION: (1)..(623)
<223> OTHER INFORMATION: Ceres Promoter construct PT0852 as found in
      Promoter Report #192

<400> SEQUENCE: 38

aatttatctt atgttcatgt gtcaaagtgg tagtgaatct agtgacgtta ttgattaatc     60

aagattactt ttatctttct gtgcaaaatt tcaagattac tctaaagtcg atatatgcta    120

ctatgacgta gttttgggac aattacgtat agagtcataa aaacaataag cagaataata    180

atccatttaa gtacattgtg aatttgtgat aatggaatta tttgacaata cttttccaaa    240

ataaaaacta atttaattac tgtattaatt attttagtaa aacaatattt tcattacaat    300

gtttgttgtg aatccaaaaa agtattgttt ccaaagaact caaatgacat caatatgtct    360

ataataacct cgtgtagctg tatgttagaa tctagccgaa ttgttttatt gttgtcggtg    420

tacgcaacaa acgaaccaca catactttga aacgtggcac aatataagtg ggtcaccaat    480

gtagctgaca actataccat ctatctgatc cgatcgctct tataacataa gcgtatggga    540

taccattttc tcggacaaag ctgaaatccc taaagaaaaa acacttctcc aaacttttca    600

tctccgatat ctctttaact aac                                            623


<210> SEQ ID NO 39
<211> LENGTH: 615
<212> TYPE: DNA
<213> ORGANISM: Arabidopsis thaliana
<220> FEATURE:
<221> NAME/KEY: misc_feature
<222> LOCATION: (1)..(615)
<223> OTHER INFORMATION: Ceres Promoter construct PT0857 as found in
      Promoter Report #200

<400> SEQUENCE: 39

agacacaacg tgttctgttc ttgtggtttt tgttgttttg atcatcttga aagacccttt     60

tttatgacaa taatcagaca acaaaaactc tttcaacaac tacataacca ctctcactat    120

cttgcttaat tctaacagag tttgaaatgt gagaaacgtg gtttggtttt tttttttgtt    180

ggagaaaaag gaaatcattt ctgtatttcc tgattcataa ttaataattt taaggtctta    240

tcatacaaaa gtgactcaat gattggtcga gagtgtatta aattttaata aaatttattt    300

aaagttcttg aatctttgtc tatttatact tttcttatgc ttgtggagtg gtttactgct    360

actgaagata aggcaagata tgggcgattg ctttttagtt gtttattaca ttcaccaacc    420

tgatattggc aaacgacact aggagatgaa ctgtcagaat ctgatatgaa atttttgcca    480

ccaaaaaaga tcactaccaa catataataa ttgatatgga tttgcttata tatataggtt    540

acggttgtta tctaaactgc attataacac tcaaacacaa gtcaaagtac ctcctgcttc    600

cacttgttct ctgcc                                                     615


<210> SEQ ID NO 40
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0757 as found in
      Promoter Report #255

<400> SEQUENCE: 40
```

aaagattatc tattaggtat ttacttcttc taatatgttt ttttttttta atatataaat 60
ggaagctata catgaaatga caaaaattca tgacatgtag agtgtaacta ttaatgtcta 120
ttgacgtaac aatagtggat tgaaaaacaa attacttttg ttttagcttg atgtatacta 180
cactaatcag ctgaaagaaa gaaaaaaaaa tccctccaat tgagatagta agagtaaaaa 240
cttattttac ttaatacaag ctgaaaattt taccctagat cctcctaact tttctttatt 300
ctctttccaa cataactatt ctaaaattta gtcaatcaca cacatctcta ctttactgat 360
tagatagtat ccgactttag tttctgattt ctctattaat atcgttagtc attatctcca 420
attctctcaa tcattagtcc cttttcaaca cacaccgctc gtattttgca tcagttacac 480
gttgaaagta ttaaatattg taatatttta ataaatagtc atcgtgggga tgtagctcaa 540
atggtagagc gctcgcttag catgcgagag gtacggggat cgataccccg catctccact 600
tagttactat tttaaaacag ttttgttatt tagtgaaaaa gtcaactatt gaaagatagg 660
tgaaaactcc gtgagtctca agcaagaccc acaagttacc tgagcttttt tcttttcttt 720
tcccggcagc tacttggatg aaaagaaaca gctgccgttt caaattcact cattttccga 780
cagtgaacag agccatatag acttgagcga agaatctttt tgccttttct catctattgg 840
ctaatcagaa aaatttaatt ccattgactt ttattcgatt acctcatttt ctattataat 900
atacacagag gtaccaaatt tcaacagtag taggcagata cctattgtct tagaaaacgt 960
tttctctttg ttctgttttt tgacacaaag gaagaagaag 1000

<210> SEQ ID NO 41
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0764 as found in
      Promoter Report #256

<400> SEQUENCE: 41
aacataaatt ttttataatg aaatttctaa ttcgagaaaa aaaaatttag tcacttccga 60
tccacaaaat ctgagttaag aaattgaaaa agaagagcta aatgttttat gtttatggaa 120
cattatttta aatgttattt taggtagtca aatgggttat ctttgggcca gacattagtc 180
attgaggagg cccacaaagg tatagaacta gagtaacgaa gccttgcctt gaaggcaata 240
atcgcttctc ccacatcgga agtttgagga tggatactcg tctgtgacat agtataaata 300
aagaacatgg tcgaagcttg caaattactt acctggacgg ggtcaactcg tgatcaagaa 360
gacgagtggc ctaggctagt gaattccatt gcacataacg gaagggtgct tagcttaagg 420
tcttcccttg tggaagagcc tgcgtcatta tttgtggcag agggggtttg cgttcgcgca 480
gcccctacca ttcccagtag ttcaatcttt tgttcatgaa tacccatggc ctaggctagt 540
ggcttcctgc acttgaggtg cgctaagcct aaggtttccc caaatggcca agtgggagat 600
cctgcgtcat tatttgttgc cttggggggc tgcgttcgcg cggcccattc catccgcaat 660
agttcaatct ttttagctct ctggtaactg ttataacatc tgaggtcttt ctttaattgt 720
tcacgctttt ggtggagcta ttttattgaa ggttgttaat ttgactttgg agatgcaatc 780
ttctaatcaa atctccacgt gagaagcgag gattctctcc tcgtcattat ttatccttcc 840
caattagagt aatcacactt ttctgtcaca tatgaattat taaaatcaga acttaagcga 900
aatccttcga ccactaaaga agaaaatccc taacaaatct cagagtttgt gttaatttct 960
tctttcctta catcttttcc agaagaaaaa aagctgaaag 1000

<210> SEQ ID NO 42
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0767 as found in
Promoter Report #257

<400> SEQUENCE: 42

```
ttaaacccgg gaatctggta aaatgtttgg attttggaac ataagtacaa tgggatgatg      60

tgacttctgc tagaaaccaa aaagatttcc aataaacaat ttacatgatg aacctaaaag     120

aagaagaaga agcaaacatc attttactta ccgtgtctaa atttataaat ttctttgtat     180

tatcaatgtg tattgtcgat cacgacacaa tcatattgtt tatcttcatt tttttgttaa     240

tcatatagag ggcaccctta atcatatttg gttattgttt atgcagttct ttaattctcg     300

agtaaccaat aagacagaaa attatcttac acgtgggctt ctaccaagat taatgtctct     360

catcatcgtc cttgtccaca ttaaaacaaa tccaaataca catatcttta gaaacataat     420

aagtaacaaa attatcacag ccaataatat cggaaacttt tgttttattc taaactttgt     480

ctccctattc gttctttcat aaatttatgt tctaatcacc actgatgacg atgatgaacc     540

cattatcttt tttttctttt ttaatatgaa cccattaact ttctagagcc aatcaaaata     600

gctgtacaaa agaaaagggt gtcataaaat aacttgtttg cttcatccat cttatatttg     660

agtacaagaa attagtagga tatttaatct tggcaaaacc tttgctaaga aaatattgag     720

tacaagtttt aagtggtggt ccatccaaga agctcatttg aactattaat ataccttgtt     780

catataatat gtaatttatt aacgtatatg taagtaaaat tttaaaaaga aaacaaaacg     840

gtccaaagtt gtaccctctt taccaatcag aaacctaaca ctaaactctc tctgtctctc     900

tctcttacat atataaaaac aaacctctcc aactctgaac tcaactcata tctctaatca     960

ctaaaacata ccacaaagaa gaaacataaa aaaaaaaagt                          1000
```

<210> SEQ ID NO 43
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0776 as found in
Promoter Report #259

<400> SEQUENCE: 43

```
ggcacaacgt gggaagattc tctcacgacc atcatctttc atgtgtgttt ttttaatgac      60

gccattcgaa acaaaacatt ctcccgacta atgaagacat gcggaaactc aacctagctc     120

gaccgccaag gatgatataa ctaaccttat aaccaataaa aactttgcgt tctttagtta     180

ctcatattta agtgaagttt aatcatttgt aaaaaaacat tgtttgtgtc aaatcattgg     240

tgaggtagaa ctaaaatggt agttttctta aaagactttg atcttgccta attagccatc     300

atctttgaat agaaaatagt tatattggac agtaagtgag acacattctc tgcccatgtt     360

tcactgtccc acaaatctct aatgaggaca aagctttaca agtcactcag tgttttatga     420

tttagctagc tgttcagaaa cccacgattt cttcatatta tatatcccat tatcattatt     480

ttaatcttct ttctcaccgc ttagttgttt gatattgcac agatcagcaa gataatcctt     540

caggatatgg ttatggaatt agtgctcctc aaaattttcg gttcgacttt attcacaatt     600
```

```
tagcatttgg gtatgcatat gaaacaaact tataatctaa tttcgttttc tcaaacacaa    660

ttcacaattt aacacacgaa gatagatgaa aacatcaagg aaattgtatc actttttcta    720

ctatgtaatg tcacagatgc agaaacaaag cgaactactt gctatcatac aaattgttat    780

gacgccaatg gaactcgcat attattccac cgaacgaaaa agaaacacaa tcatgataaa    840

ataattgaga gagattaaat aaaattagat tctgactaat cattgttttt cagcttttgg    900

tttccactct cttattatca acttcgcttg ggaccttcaa atctcagttg cacaaaaatg    960

ccataaaact agccaaaaag tgaagaaata gaggagaaaa                         1000
```

<210> SEQ ID NO 44
<211> LENGTH: 362
<212> TYPE: DNA
<213> ORGANISM: Arabidopsis thaliana
<220> FEATURE:
<221> NAME/KEY: misc_feature
<222> LOCATION: (1)..(362)
<223> OTHER INFORMATION: Ceres Promoter construct PT0889 as found in Promoter Report #260

<400> SEQUENCE: 44

```
cggttgacac gtgaatacgt aagtttgtaa ctaaccgtag catatgatat cttttcaatg     60

gtggcgcgtg gggagcacaa gttattgatt tgcctcgtcg gcgtccacca ccattatcgc    120

cggattttta tatattcacg tagaagaaga atgagaagac gaaaaccaac ttctacttct    180

tctcagtggc tctctcttta tctttcttgg agtttagtta gagattttaa cgttgcaaat    240

ggatcaacca atgaaaccaa aaacttgctc tgaatctgat tttgctgatg attcctctgc    300

ttcttcttct tcttcttcgg gacaaaatct caggttttag tgcttaaaga tgttaacttt    360

ac                                                                   362
```

<210> SEQ ID NO 45
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0585 as found in Promoter Report #267

<400> SEQUENCE: 45

```
tgaagtcatt taatatgagt ttgacattag gtaaacctaa tctatgagat tatagaatgt     60

agcaaaacta tcaatgtttc ttttccaaaa tattttgtgg tttttctttt tggttcatta    120

tgttttgtta tttgtgaatt attttaatat gaagtaatta tattgatttt atatgatata    180

catattattt tgatataaaa tttaacactt atccattaaa atagcatggg cataatcaaa    240

atcgggacta ttacgatgaa aaagatagtt aaattgtatg ataaaataaa atgtgtaaga    300

ttaaaatttt gggttttaga aaattactaa acaaaatata gacaaagtat gttgactatt    360

atttaaaatt taaatatcat caataagata tagttaaagt cattaagtgt atagcaaaat    420

gaaaattcta agattaaaat tcgattaaaa ttttttttac taaattaaat atttaaaaat    480

agggattatc atttactatt tacaattcta atatcatggg taaaaattga taactttttt    540

taaacccgcc tatctaggtg ggcctaacct agtttactaa ttactatatg attaacttat    600

taccactttt acttcttctt ttttggtcaa attactttat tgttttttat aaagtcaaat    660

tactctttgc attgtaaata atagtagtaa ctaaaatctt aaaacaaaat attcaacctt    720

tcccattatt ggaatggtaa tgtcttcaac accattgacc aacgttaagg aatgtctttt    780
```

```
aatatttttg gaacctaaat gctaatactg tataccacaa tcacttatga gtattgaagt    840

tgagatagag gaggtacaag gagaccttat ctgcagaaga caaaaagcca tttttagcaa    900

aactaaagaa agaaaaaaga ttgaaacaca aatatgcgcc actcgtagtc cacccctatc    960

tctttggcaa aagccacttc actctttttc ccttttttata                        1000


<210> SEQ ID NO 46
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0565 as found in
      Promoter Report #268

<400> SEQUENCE: 46

caccaaatat agtgttattt caatactaaa atggtgttat ggttggagat gccctaaaga     60

taaacatgac gagacacgag atttattaat ttcttgatca accataactt aataacttaa    120

tattaatttc acttaataat ttccaattaa gtgaatcttt acttcaccaa aagttcctaa    180

cgaactctta ttttctagca tcaatattac catgaactag catcaatact atcatgaaaa    240

attcctactt cctatccaac tcttaataac aatgctagtc ttaacaatat tcatcaaaaa    300

cttgatatag accttctaac ttagccacga ctagtatcgg tgaataccaa aattaatgta    360

ttcatgagaa cttgagattt ctctaatgta ttcttgttac taaacaagta acaacactca    420

agaaatatca tgatcaaata ttttactcat aaactccata tttcacattt tgaaaatttt    480

aaacagcaaa tcacattgaa ttttcgtggt aaaagtattt aaaattgaaa aatagcagct    540

cctgatttca atgtataaat ttatctttat atggtttatg tctccaactt attttaaaaa    600

agagagaaag agcacccaaa aggtgaccgt ttgaaattcg aatttatttc cgtttgaaat    660

tcgaattcaa aaaaagtaaa ccgaaccgag tctcgttact gactgtcaca cattgtttcc    720

ctaaaagcta attaacccat acgtggcgta atataacagg tcagtgatca atactaaata    780

acagacatac acctttaaaa ttcgtgcacg ctccaaaaca aaatctacac ttcaaaatca    840

acggtcacga tcattcctca aatttcaaaa aattatttaa cctcacttcc ttcgctttgt    900

ttttaaaacc tctctctctt tctctttctc tttcgccatt aaaactctgt ttcctttttc    960

agagattctc agagaagatt cattttaccc taagaaaaaa                        1000
```

PROMOTER, PROMOTER CONTROL ELEMENTS, AND COMBINATIONS, AND USES THEREOF

This Nonprovisional application is a Divisional of Ser. No. 11/233,726 filed on Sep. 23, 2005 which claims priority under 35 U.S.C. §119(e) on U.S. Provisional Application No(s). 60/612,891; 60/613,134; and 60/637,174 filed on Sep. 23, 2004; Sep. 23, 2004 and Dec. 16, 2004, the entire contents of which are hereby incorporated by reference.

FIELD OF THE INVENTION

The present invention relates to promoters and promoter control elements that are useful for modulating transcription of a desired polynucleotide. Such promoters and promoter control elements can be included in polynucleotide constructs, expression cassettes, vectors, or inserted into the chromosome or as an exogenous element, to modulate in vivo and in vitro transcription of a polynucleotide. Host cells, including plant cells, and organisms, such as regenerated plants therefrom, with desired traits or characteristics using polynucleotides comprising the promoters and promoter control elements of the present invention are also a part of the invention.

BACKGROUND OF THE INVENTION

This invention relates to the field of biotechnology and, in particular, to specific promoter sequences and promoter control element sequences which are useful for the transcription of polynucleotides in a host cell or transformed host organism.

One of the primary goals of biotechnology is to obtain organisms, such as plants, mammals, yeast, and prokaryotes having particular desired characteristics or traits. Examples of these characteristic or traits abound and may include, for example, in plants, virus resistance, insect resistance, herbicide resistance, enhanced stability or additional nutritional value. Recent advances in genetic engineering have enabled researchers in the field to incorporate polynucleotide sequences into host cells to obtain the desired qualities in the organism of choice. This technology permits one or more polynucleotides from a source different than the organism of choice to be transcribed by the organism of choice. If desired, the transcription and/or translation of these new polynucleotides can be modulated in the organism to exhibit a desired characteristic or trait. Alternatively, new patterns of transcription and/or translation of polynucleotides endogenous to the organism can be produced. Both approaches can be used at the same time.

SUMMARY OF THE INVENTION

The present invention is directed to isolated polynucleotide sequences that comprise promoters and promoter control elements from plants, especially *Arabidopsis thaliana, Glycine max, Oryza sativa*, and *Zea mays*, and other promoters and promoter control elements functional in plants.

It is an object of the present invention to provide isolated polynucleotides that are promoter sequences. These promoter sequences comprise, for example, (1) a polynucleotide having a nucleotide sequence as set forth in the Sequence Listing or a fragment thereof;

(2) a polynucleotide having a nucleotide sequence having at least 80% sequence identity to a sequence as set forth in the Sequence Listing or a fragment thereof; and (3) a polynucleotide having a nucleotide sequence which hybridizes to a sequence as set forth in the Sequence Listing under a condition establishing a Tm-20° C.

It is another object of the present invention to provide isolated polynucleotides that are promoter control element sequences. These promoter control element sequences comprise, for example, (1) a polynucleotide having a nucleotide sequence as set forth in SEQ ID NOs: 1-46 or a fragment thereof;

(2) a polynucleotide having a nucleotide sequence having at least 80% sequence identity to a sequence as set forth in SEQ ID NOs: 1-46 or fragment thereof; and (3) a polynucleotide having a nucleotide sequence which hybridizes to a sequence as set forth in SEQ ID NOs: 1-46 under a condition establishing a Tm-20° C.

Promoter or promoter control element sequences of the present invention are capable of modulating preferential transcription.

In another embodiment, the present promoter control elements are capable of serving as or fulfilling the function, for example, as a core promoter, a TATA box, a polymerase binding site, an initiator site, a transcription binding site, an enhancer, an inverted repeat, a locus control region, or a scaffold/matrix attachment region.

It is yet another object of the present invention to provide a polynucleotide that includes at least a first and a second promoter control element. The first promoter control element is a promoter control element sequence as discussed above and the second promoter control element is heterologous to the first control element. Moreover, the first and second control elements are operably linked. Such promoters may modulate transcript levels preferentially in a tissue or under particular conditions.

In another embodiment, the present isolated polynucleotide comprises a promoter or a promoter control element as described above, wherein the promoter or promoter control element is operably linked to a polynucleotide to be transcribed.

In another embodiment of the present vector, the promoter and promoter control elements of the instant invention are operably linked to a heterologous polynucleotide that is a regulatory sequence.

It is another object of the present invention to provide a host cell comprising an isolated polynucleotide or vector as described above or fragment thereof. Host cells include, for instance, bacterial, yeast, insect, mammalian, and plant. The host cell can comprise a promoter or promoter control element exogenous to the genome. Such a promoter can modulate transcription in cis- and in trans-.

In yet another embodiment, the present host cell is a plant cell capable of regenerating into a plant.

It is yet another embodiment of the present invention to provide a plant comprising an isolated polynucleotide or vector described above.

It is another object of the present invention to provide a method of modulating transcription in a sample that contains either a cell-free system of transcription or host cell. This method comprises providing a polynucleotide or vector according to the present invention as described above, and contacting the sample of the polynucleotide or vector with conditions that permit transcription.

In another embodiment of the present method, the polynucleotide or vector preferentially modulates (a) constitutive transcription, (b) stress induced transcription, (c) light induced transcription, (d) dark induced transcription, (e) leaf transcription,
(f) root transcription,
(g) stem or shoot transcription,
(h) silique transcription,
(i) callus transcription,
(j) flower transcription,
(k) immature bud and inflorescence specific transcription, or
(l) senescing induced transcription
(m) germination transcription.

Other and further objects of the present invention will be made clear or become apparent from the following description.

BRIEF DESCRIPTION OF THE FIGURES

FIG. 1 is a schematic representation of the vector pNew-Bin4-HAP1-GFP. The definitions of the abbreviations used in the vector map are as follows:

Ori—the origin of replication used by an *E. coli* host
RB—sequence for the right border of the T-DNA from pMOG800
BstXI—restriction enzyme cleavage site used for cloning
HAP1VP16—coding sequence for a fusion protein of the HAP1 and VP16 activation domains
NOS—terminator region from the nopaline synthase gene
HAP1UAS—the upstream activating sequence for HAP 1
5ERGFP—the green fluorescent protein gene that has been optimized for localization to the endoplasmic reticulum
OCS2—the terminator sequence from the octopine synthase 2 gene
OCS—the terminator sequence from the octopine synthase gene
p28716 (a.k.a 28716 short)—promoter used to drive expression of the PAT (BAR) gene
PAT (BAR)—a marker gene conferring herbicide resistance
LB—sequence for the left border of the T-DNA from pMOG800
Spec—a marker gene conferring spectinomycin resistance
TrfA—transcription repression factor gene
RK2-OriV —origin of replication for *Agrobacterium*

FIG. 2

Figure 2:
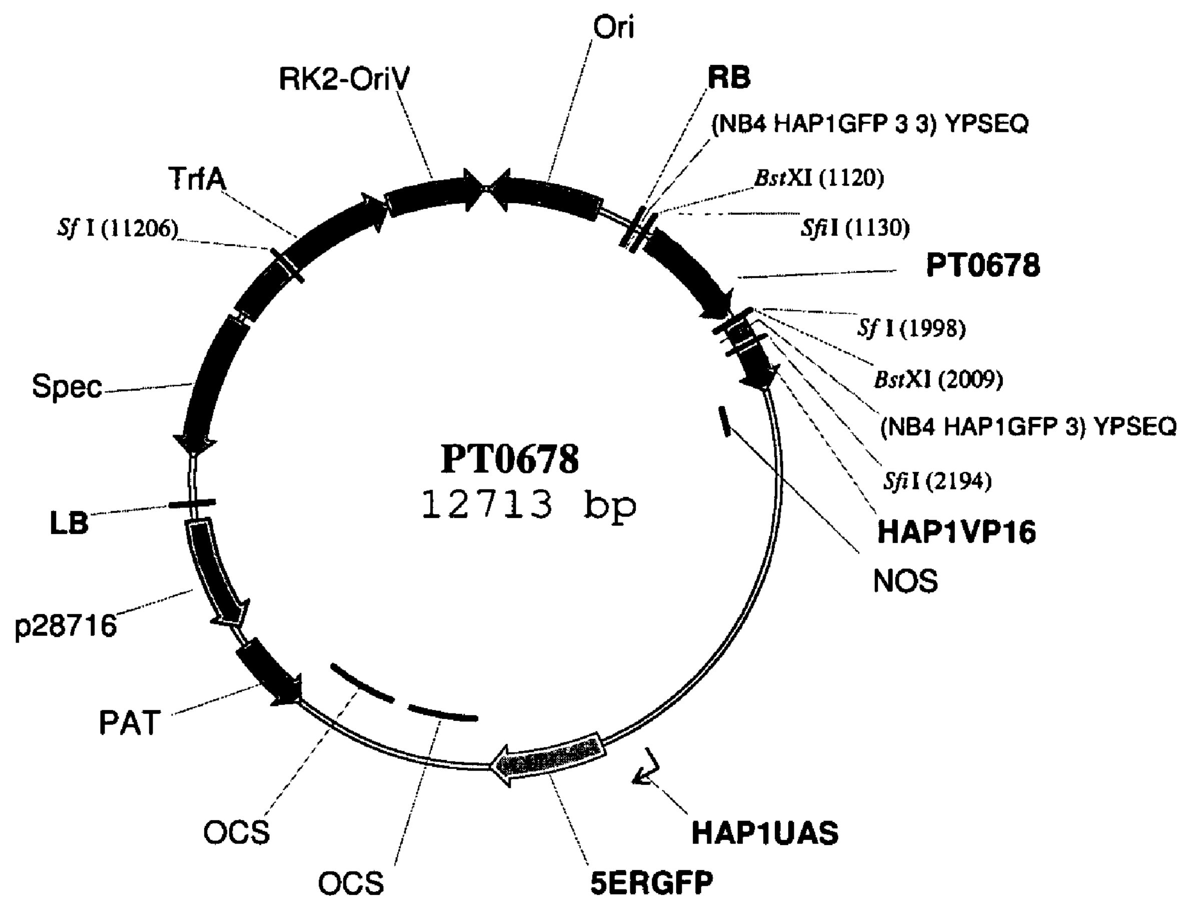

FIG. 2 is a schematic representation of the vector PT0678. The definitions of the abbreviations used in the vector map are as described above.

FIG. 3

FIG. 3 is a schematic of a gene.

DETAILED DESCRIPTION OF THE INVENTION

1. Definitions

Chimeric: The term "chimeric" is used to describe polynucleotides or genes, as defined supra, or constructs wherein at least two of the elements of the polynucleotide or gene or construct, such as the promoter and the polynucleotide to be transcribed and/or other regulatory sequences and/or filler sequences and/or complements thereof, are heterologous to each other.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Core Promoter: This is the minimal stretch of contiguous DNA sequence that is sufficient to direct accurate initiation of transcription by the RNA polymerase II machinery (for review see: Struhl, 1987, *Cell* 49: 295-297; Smale, 1994, In *Transcription: Mechanisms and Regulation* (eds R. C. Conaway and J. W. Conaway), pp 63-81/Raven Press, Ltd., New York; Smale, 1997, *Biochim. Biophys. Acta* 1351: 73-88; Smale et al., 1998, *Cold Spring Harb. Symp. Quant. Biol.* 58: 21-31; Smale, 2001, *Genes & Dev.* 15: 2503-2508; Weis and Reinberg, 1992, *FASEB J.* 6: 3300-3309; Burke et al., 1998, *Cold Spring Harb. Symp. Quant. Biol* 63: 75-82). There are several sequence motifs, including the TATA box, initiator (Inr), TFIIB recognition element (BRE) and downstream core promoter element (DPE), that are commonly found in core promoters, however not all of these elements occur in all promoters and there are no universal core promoter elements (Butler and Kadonaga, 2002, Genes & Dev. 16: 2583-2592).

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. A similar analysis can be applied to polynucleotides. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed. Examples of domains include, without limitation, AP2, helicase, homeobox, zinc finger, etc.

Endogenous: The term "endogenous," within the context of the current invention refers to any polynucleotide, polypeptide or protein sequence which is a natural part of a cell or organisms regenerated from said cell. In the context of promoter, the term "endogenous coding region" or "endogenous cDNA" refers to the coding region that is naturally operably linked to the promoter.

Enhancer/Suppressor: An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

Exogenous: As referred to within, "exogenous" is any polynucleotide, polypeptide or protein sequence, whether chimeric or not, that is introduced into the genome of a host cell or organism regenerated from said host cell by any means other than by a sexual cross. Examples of means by which this can be accomplished are described below, and include *Agrobacterium*-mediated transformation (of dicots—e.g. Salomon et al. EMBO J. 3:141 (1984); Herrera-Estrella et al. EMBO J. 2:987 (1983); of monocots, representative papers are those by Escudero et al., Plant J. 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Gene: The term "gene," as used in the context of the current invention, encompasses all regulatory and coding sequence contiguously associated with a single hereditary unit with a genetic function (see FIG. 3). Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes encoding proteins are comprised of "exons" (coding sequences), which may be interrupted by "introns" (non-coding sequences). In some instances complexes of a plurality of protein or nucleic acids or other molecules, or of any two of the above, may be required for a gene's function. On the other hand a gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, in an artificial chromosome, in a plasmid, in any other sort of vector, or as a separate isolated entity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other.

Homologous: In the current invention, a "homologous" gene or polynucleotide or polypeptide refers to a gene or polynucleotide or polypeptide that shares sequence similarity with the gene or polynucleotide or polypeptide of interest. This similarity may be in only a fragment of the sequence and often represents a functional domain such as, examples including without limitation a DNA binding domain or a domain with tyrosine kinase activity. The functional activities of homologous polynucleotide are not necessarily the same.

Inducible Promoter: An "inducible promoter" in the context of the current invention refers to a promoter, the activity of which is influenced by certain conditions, such as light, temperature, chemical concentration, protein concentration, conditions in an organism, cell, or organelle, etc. A typical example of an inducible promoter, which can be utilized with the polynucleotides of the present invention, is PARSK1, the promoter from an *Arabidopsis* gene encoding a serine-threonine kinase enzyme, and which promoter is induced by dehydration, abscissic acid and sodium chloride (Wang and Goodman, Plant J. 8:37 (1995)). Examples of environmental conditions that may affect transcription by inducible promoters include anaerobic conditions, elevated temperature, the presence or absence of a nutrient or other chemical compound or the presence of light.

Modulate Transcription Level: As used herein, the phrase "modulate transcription" describes the biological activity of a promoter sequence or promoter control element. Such modulation includes, without limitation, includes up- and down-regulation of initiation of transcription, rate of transcription, and/or transcription levels.

Mutant: In the current invention, "mutant" refers to a heritable change in nucleotide sequence at a specific location. Mutant genes of the current invention may or may not have an associated identifiable phenotype.

Operable Linkage: An "operable linkage" is a linkage in which a promoter sequence or promoter control element is connected to a polynucleotide sequence (or sequences) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of mRNA encoding the polynucleotide and if the nature of the linkage between the two DNA sequences does not (1) result in the introduction of a frame-shift mutation, (2) interfere with the ability of the promoter sequence to direct the expression of the protein, antisense RNA or ribozyme, or (3) interfere with the ability of the DNA template to be transcribed. Thus, a promoter sequence would be operably linked to a polynucleotide sequence if the promoter was capable of effecting transcription of that polynucleotide sequence.

Optional Promoter Fragments: The phrase "optional promoter fragments" is used to refer to any sub-sequence of the promoter that is not required for driving transcription of an operationally linked coding region. These fragments comprise the 5' UTR and any exon(s) of the endogenous coding region. The optional promoter fragments may also comprise any exon(s) and the 3' or 5' UTR of the gene residing upstream of the promoter (that is, 5' to the promoter). Optional promoter fragments also include any intervening sequences that are introns or sequence that occurs between exons or an exon and the UTR.

Orthologous: "Orthologous" is a term used herein to describe a relationship between two or more polynucleotides or proteins. Two polynucleotides or proteins are "orthologous" to one another if they serve a similar function in different organisms. In general, orthologous polynucleotides or proteins will have similar catalytic functions (when they encode enzymes) or will serve similar structural functions (when they encode proteins or RNA that form part of the ultrastructure of a cell).

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444

(1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used.

Plant Promoter: A "plant promoter" is a promoter capable of initiating transcription in plant cells and can modulate transcription of a polynucleotide. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill.

Plant Tissue: The term "plant tissue" includes differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoter: A "promoter" is a DNA sequence that directs the transcription of a polynucleotide. Typically a promoter is located in the 5' region of a polynucleotide to be transcribed, proximal to the transcriptional start site of such polynucleotide. More typically, promoters are defined as the region upstream of the first exon; more typically, as a region upstream of the first of multiple transcription start sites; more typically, as the region downstream of the preceding gene and upstream of the first of multiple transcription start sites; more typically, the region downstream of the polyA signal and upstream of the first of multiple transcription start sites; even more typically, about 3,000 nucleotides upstream of the ATG of the first exon; even more typically, 2,000 nucleotides upstream of the first of multiple transcription start sites. The promoters of the invention comprise at least a core promoter as defined above. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include UARs and optionally, other DNA sequences that affect transcription of a polynucleotide such as a synthetic upstream element.

Promoter Control Element: The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats.

Public sequence: The term "public sequence," as used in the context of the instant application, refers to any sequence that has been deposited in a publicly accessible database prior to the filing date of the present application. This term encompasses both amino acid and nucleotide sequences. Such sequences are publicly accessible, for example, on the BLAST databases on the NCBI FTP web site (accessible via the internet). The database at the NCBI FTP site utilizes "gi" numbers assigned by NCBI as a unique identifier for each sequence in the databases, thereby providing a non-redundant database for sequence from various databases, including GenBank, EMBL, DBBJ, (DNA Database of Japan) and PDB (Brookhaven Protein Data Bank).

Regulatory Sequence: The term "regulatory sequence," as used in the current invention, refers to any nucleotide sequence that influences transcription or translation initiation and rate, or stability and/or mobility of a transcript or polypeptide product. Regulatory sequences include, but are not limited to, promoters, promoter control elements, protein binding sequences, 5' and 3' UTRs, transcriptional start sites, termination sequences, polyadenylation sequences, introns, certain sequences within amino acid coding sequences such as secretory signals, protease cleavage sites, etc.

Related Sequences: "Related sequences" refer to either a polypeptide or a nucleotide sequence that exhibits some degree of sequence similarity with a reference sequence.

Specific Promoters: In the context of the current invention, "specific promoters" refers to a subset of promoters that have a high preference for modulating transcript levels in a specific tissue or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used with the polynucleotides of the present invention, are: PTA29, a promoter which is capable of driving gene transcription specifically in tapetum and only during anther development (Koltonow et al., Plant Cell 2:1201 (1990); RCc2 and RCc3, promoters that direct root-specific gene transcription in rice (Xu et al., Plant Mol. Biol. 27:237 (1995); TobRB27, a root-specific promoter from tobacco (Yamamoto et al., Plant Cell 3:371 (1991)). Examples of tissue-specific promoters under developmental control include promoters that initiate transcription only in certain tissues or organs, such as root, ovule, fruit, seeds, or flowers. Other specific promoters include those from genes encoding seed storage proteins or the lipid body membrane protein, oleosin. A few root-specific promoters are noted above. See also "Preferential transcription".

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$−5° C. to $T_m$−10° C. Medium or moderate stringency conditions are those providing $T_m$−20° C. to $T_m$−29° C. Low stringency conditions are those providing a condition of $T_m$−40° C. to $T_m$−48° C. The relationship of hybridization conditions to $T_m$ (in ° C.) is expressed in the mathematical equation $$T_m=81.5-16.6(\log_{10}[Na^+])+0.41(\%\ G+C)-(600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6\log\{[Na^+]/(1+0.7[Na^+])\}+0.41(\%\ G+C)-500/L0.63(\%\ \text{formamide}) \quad (2)$$

where L is the length of the probe in the hybrid. (P. Tijessen, "Hybridization with Nucleic Acid Probes" in *Laboratory Techniques in Biochemistry and Molecular Biology*, P. C. vand der Vliet, ed., c. 1993 by Elsevier, Amsterdam). The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., J. Mol. Biol. 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene can be substantially free of other plant genes. Other examples include, but are not limited to, ligands substantially free of receptors (and vice versa), a growth factor substantially free of other growth factors and a transcription binding factor substantially free of nucleic acids.

Suppressor: See "Enhancer/Suppressor"

TATA to start: "TATA to start" shall mean the distance, in number of nucleotides, between the primary TATA motif and the start of transcription.

Transgenic plant: A "transgenic plant" is a plant having one or more plant cells that contain at least one exogenous polynucleotide introduced by recombinant nucleic acid methods.

Translational start site: In the context of the present invention, a "translational start site" is usually an ATG or AUG in a transcript, often the first ATG or AUG. A single protein encoding transcript, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single polynucleotide to be transcribed may have multiple transcriptional start sites, some of which may be specific for transcription in a particular cell-type or tissue or organ. "+1" is stated relative to the transcription start site and indicates the first nucleotide in a transcript.

Upstream Activating Region (UAR): An "Upstream Activating Region" or "UAR" is a position or orientation dependent nucleic acid element that primarily directs tissue, organ, cell type, or environmental regulation of transcript level, usually by affecting the rate of transcription initiation. Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

Untranslated region (UTR): A "UTR" is any contiguous series of nucleotide bases that is transcribed, but is not translated. A 5' UTR lies between the start site of the transcript and the translation initiation codon and includes the +1 nucleotide. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc). Likewise, polynucleotide variants can consist of changes that add or delete a specific UTR or exon sequence. It will be understood that there may be sequence variations within sequence or fragments used or disclosed in this application. Preferably, variants will be such that the sequences have at least 80%, preferably at least 90%, 95, 97, 98, or 99% sequence identity. Variants preferably measure the primary biological function of the native polypeptide or protein or polynucleotide.

2. Introduction

The polynucleotides of the invention comprise promoters and promoter control elements that are capable of modulating transcription.

Such promoters and promoter control elements can be used in combination with native or heterologous promoter fragments, control elements or other regulatory sequences to modulate transcription and/or translation.

Specifically, promoters and control elements of the invention can be used to modulate transcription of a desired polynucleotide, which includes without limitation:

(a) antisense;
(b) ribozymes;
(c) coding sequences; or
(d) fragments thereof.

The promoter also can modulate transcription in a host genome in cis- or in trans-.

In an organism, such as a plant, the promoters and promoter control elements of the instant invention are useful to produce preferential transcription which results in a desired pattern of transcript levels in a particular cells, tissues, or organs, or under particular conditions.

3. Table of Contents

The following description of the present invention is outlined in the following table of contents.

A. Identifying and Isolating Promoter Sequences of the Invention
(1) Cloning Methods
(2) Chemical Synthesis
B. Isolating Related Promoter Sequences
(1) Relatives Based on Nucleotide Sequence Identity
C. Promoter Control Elements of the Invention
(1) Promoter Control Element Configuration
(2) Those Identifiable by Bioinformatics
(3) Those Identifiable by In Vitro and In Vivo Assays
(4) Non-Natural Control Elements
D. Constructing Promoters and Control Elements
(1) Combining Promoters and Promoter Control Elements
(2) Number of Promoter Control Elements
(3) Spacing Between Control Elements
(4) Other Promoters
E. Vectors
(1) Modification of Transcription by Promoters and Promoter Control Elements
(2) Polynucleotide to be Transcribed
(3) Other Regulatory Elements
(4) Other Components of Vectors
F. Insertion of Polynucleotides and Vectors Into a Host Cell
(1) Autonomous of the Host Genome
(2) Integrated into the Host Genome
G. Utility A. Identifying and Isolating Promoter Sequences of the Invention The promoters and promoter control elements of the present invention are presented in SEQ ID NOs: 1-46 and were identified from *Arabidopsis thaliana* or *Oyza sativa*. Additional promoter sequences encompassed by the invention can be identified as described below.

(1) Cloning Methods

Isolation from genomic libraries of polynucleotides comprising the sequences of the promoters and promoter control elements of the present invention is possible using known techniques.

For example, polymerase chain reaction (PCR) can amplify the desired polynucleotides utilizing primers designed from sequences in the row titled "The spatial expression of the promoter-marker-vector". Polynucleotide libraries comprising genomic sequences can be constructed according to Sambrook et al., *Molecular Cloning: A Laboratory Manual,* $2^{nd}$ Ed. (1989) Cold Spring Harbor Press, Cold Spring Harbor, N.Y.), for example.

Other procedures for isolating polynucleotides comprising the promoter sequences of the invention include, without limitation, tail-PCR, and 5' rapid amplification of cDNA ends (RACE). See, for tail-PCR, for example, Liu et al., *Plant J* 8 (3): 457-463 (September, 1995); Liu et al., *Genomics* 25: 674-681 (1995); Liu et al., *Nucl. Acids Res.* 21 (14): 3333-3334 (1993); and Zoe et al., *BioTechniques* 27 (2): 240-248 (1999); for RACE, see, for example, *PCR Protocols: A Guide to Methods and Applications*, (1990) Academic Press, Inc.

(2) Chemical Synthesis

In addition, the promoters and promoter control elements described in SEQ ID NOs: 1-46 can be chemically synthesized according to techniques in common use. See, for example, Beaucage et al., *Tet. Lett*. (1981) 22: 1859 and U.S. Pat. No. 4,668,777.

Such chemical oligonucleotide synthesis can be carried out using commercially available devices, such as, Biosearch 4600 or 8600 DNA synthesizer, by Applied Biosystems, a division of Perkin-Elmer Corp., Foster City, Calif., USA; and Expedite by Perceptive Biosystems, Framingham, Mass., USA.

Synthetic RNA, including natural and/or analog building blocks, can be synthesized on the Biosearch 8600 machines, see above.

Oligonucleotides can be synthesized and then ligated together to construct the desired polynucleotide.

B. Isolating Related Promoter Sequences

Included in the present invention are promoter and promoter control elements that are related to those described in SEQ ID NOs: 1-46. Such a related sequence can be isolated utilizing (a) nucleotide sequence identity;
(b) coding sequence identity; or
(c) common function or gene products.

Relatives can include both naturally occurring promoters and non-natural promoter sequences. Non-natural related promoters include nucleotide substitutions, insertions or deletions of naturally-occurring promoter sequences that do not substantially affect transcription modulation activity. For example, the binding of relevant DNA binding proteins can still occur with the non-natural promoter sequences and promoter control elements of the present invention.

According to current knowledge, promoter sequences and promoter control elements exist as functionally important regions, such as protein binding sites, and spacer regions. These spacer regions are apparently required for proper positioning of the protein binding sites. Thus, nucleotide substitutions, insertions and deletions can be tolerated in these spacer regions to a certain degree without loss of function.

In contrast, less variation is permissible in the functionally important regions, since changes in the sequence can interfere with protein binding. Nonetheless, some variation in the functionally important regions is permissible so long as function is conserved.

The effects of substitutions, insertions and deletions to the promoter sequences or promoter control elements may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

(1) Relatives Based on Nucleotide Sequence Identity

Included in the present invention are promoters exhibiting nucleotide sequence identity to those described in SEQ ID NOs: 1-46.

Typically, such related promoters exhibit at least 80% sequence identity, preferably at least 85%, more preferably at least 90%, and most preferably at least 95%, even more preferably, at least 96%, 97%, 98% or 99% sequence identity compared to those shown in SEQ ID NOs: 1-46. Such sequence identity can be calculated by the algorithms and computers programs described above.

Usually, such sequence identity is exhibited in an alignment region that is at least 75% of the length of a sequence shown in SEQ ID NOs: 1-46; more usually at least 80%; more usually, at least 85%, more usually at least 90%, and most usually at least 95%, even more usually, at least 96%, 97%, 98% or 99% of the length of a sequence shown in Table 1 in the section entitled "The predicted promoter sequence".

The percentage of the alignment length is calculated by counting the number of residues of the sequence in region of strongest alignment, e.g., a continuous region of the sequence that contains the greatest number of residues that are identical to the residues between two sequences that are being aligned. The number of residues in the region of strongest alignment is divided by the total residue length of a sequence in SEQ ID NOs: 1-46.

These related promoters may exhibit similar preferential transcription as those promoters described in Table 1 in the section entitled "The predicted promoter sequence".

Construction of Polynucleotides

Naturally occurring promoters that exhibit nucleotide sequence identity to those shown in SEQ ID NOs: 1-46 can be isolated using the techniques as described above. More specifically, such related promoters can be identified by varying stringencies, as defined above, in typical hybridization procedures such as Southern blots or probing of polynucleotide libraries, for example.

Non-natural promoter variants of those shown in SEQ ID NOs: 1-46 can be constructed using cloning methods that incorporate the desired nucleotide variation. See, for example, Ho, S, N., et al. Gene 77:51-59 1989, describing a procedure site directed mutagenesis using PCR.

Any related promoter showing sequence identity to those shown in Table can be chemically synthesized as described above.

Also, the present invention includes non-natural promoters that exhibit the above-sequence identity to those in SEQ ID NOs: 1-46.

The promoters and promoter control elements of the present invention may also be synthesized with 5' or 3' extensions, to facilitate additional manipulation, for instance.

Testing of Polynucleotides

Polynucleotides of the invention were tested for activity by cloning the sequence into an appropriate vector, transforming plants with the construct and assaying for marker gene expression. Recombinant DNA constructs were prepared which comprise the polynucleotide sequences of the invention inserted into a vector suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996);

(b) YAC: Burke et al., Science 236:806-812 (1987);

(c) PAC: Sternberg N. et al., Proc Natl Acad Sci USA. January; 87 (1):103-7 (1990);

(d) Bacteria-Yeast Shuttle Vectors: Bradshaw et al., Nucl Acids Res 23: 4850-4856 (1995);

(e) Lambda Phage Vectors: Replacement Vector, e.g., Frischauf et al., J. Mol Biol 170: 827-842 (1983); or Insertion vector, e.g., Huynh et al., In: Glover N M (ed) DNA Cloning: A practical Approach, Vol. 1 Oxford: IRL Press (1985); T-DNA gene fusion vectors Walden et al., Mol Cell Biol 1: 175-194 (1990); and (g) Plasmid vectors: Sambrook et al., infra.

Typically, the construct comprises a vector containing a sequence of the present invention operationally linked to any marker gene. The polynucleotide was identified as a promoter by the expression of the marker gene. Although many marker genes can be used, Green Fluorescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin. Vectors can also include origins of replication, scaffold attachment regions (SARs), markers, homologous sequences, introns, etc.

C. Promoter Control Elements of the Invention

The promoter control elements of the present invention include those that comprise a sequence shown in SEQ ID NOs: 1-46 and fragments thereof. The size of the fragments can range from 5 bases to 10 kilobases (kb). Typically, the fragment size is no smaller than 8 bases; more typically, no smaller than 12; more typically, no smaller than 15 bases; more typically, no smaller than 20 bases; more typically, no smaller than 25 bases; even more typically, no more than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

(1) Promoter Control Element Configuration

A common configuration of the promoter control elements in RNA polymerase II promoters can be found in "Models for prediction and recognition of eukaryotic promoters", T. Werner, Mammalian Genome, 10, 168-175 (1999).

Promoters are generally modular in nature. Promoters can consist of a basal promoter which functions as a site for assembly of a transcription complex comprising an RNA polymerase, for example RNA polymerase II. A typical transcription complex will include additional factors such as $TF_{II}B$, $TF_{II}D$, and $TF_{II}E$. Of these, $TF_{II}D$ appears to be the only one to bind DNA directly. The promoter might also contain one or more promoter control elements such as the elements discussed above. These additional control elements may function as binding sites for additional transcription factors that have the function of modulating the level of transcription with respect to tissue specificity and of transcriptional responses to particular environmental or nutritional factors, and the like.

One type of promoter control element is a polynucleotide sequence representing a binding site for proteins. Typically, within a particular functional module, protein binding sites constitute regions of 5 to 60, preferably 10 to 30, more preferably 10 to 20 nucleotides. Within such binding sites, there are typically 2 to 6 nucleotides which specifically contact amino acids of the nucleic acid binding protein.

The protein binding sites are usually separated from each other by 10 to several hundred nucleotides, typically by 15 to 150 nucleotides, often by 20 to 50 nucleotides.

Further, protein binding sites in promoter control elements often display dyad symmetry in their sequence. Such elements can bind several different proteins, and/or a plurality of sites can bind the same protein. Both types of elements may be combined in a region of 50 to 1,000 base pairs.

Binding sites for any specific factor have been known to occur almost anywhere in a promoter. For example, functional AP-1 binding sites can be located far upstream, as in the rat bone sialoprotein gene, where an AP-1 site located about 900 nucleotides upstream of the transcription start site suppresses expression. Yamauchi et al., Matrix Biol., 15, 119-130 (1996). Alternatively, an AP-1 site located close to the transcription start site plays an important role in the expression of Moloney murine leukemia virus. Sap et al., Nature, 340, 242-244, (1989).

(2) Those Identifiable by Bioinformatics

Promoter control elements from the promoters of the instant invention can be identified utilizing bioinformatic or computer driven techniques.

One method uses a computer program AlignACE to identify regulatory motifs in genes that exhibit common preferential transcription across a number of time points. The program identifies common sequence motifs in such genes. See, Roth et al., Nature Biotechnol. 16: 949-945 (1998); Tavazoie et al., Nat Genet 1999 July; 22 (3):281-5;

Genomatix, also makes available a GEMS Launcher program and other programs to identify promoter control elements and configuration of such elements. Genomatix is located in Munich, Germany.

Other references also describe detection of promoter modules by models independent of overall nucleotide sequence similarity. See, for instance, Klingenhoff et al., Bioinformatics 15, 180-186 (1999).

Protein binding sites of promoters can be identified as reported in "Computer-assisted prediction, classification, and delimination of protein binding sites in nucleic acids", Frech, et al., Nucleic Acids Research, Vol. 21, No. 7, 1655-1664, 1993.

Other programs used to identify protein binding sites include, for example, Signal Scan, Prestridge et al., Comput. Appl. Biosci. 12: 157-160 (1996); Matrix Search, Chen et al., Comput. Appl. Biosci. 11: 563-566 (1995), available as part of Signal Scan 4.0; MatInspector, Ghosh et al., Nucl. Acid Res. 21: 3117-3118 (1993) available via the internet and ConsInspector, Frech et al., Nucl. Acids Res. 21: 1655-1664 (1993), available via the internet; TFSearch; and TESS.

Frech et al., "Software for the analysis of DNA sequence elements of transcription", Bioinformatics & Sequence Analysis, Vol. 13, no. 1, 89-97 (1997) is a review of different software for analysis of promoter control elements. This paper also reports the usefulness of matrix-based approaches to yield more specific results.

For other procedures, see, Fickett et al., Curr. Op. Biotechnol. 11: 19-24 (2000); and Quandt et al., Nucleic Acids Res., 23, 4878-4884 (1995).

(3) Those Identifiable by In-Vitro and In-Vivo Assays

Promoter control elements also can be identified with in-vitro assays, such as transcription detection methods; and with in-vivo assays, such as enhancer trapping protocols.

In-Vitro Assays

Examples of in-vitro assays include detection of binding of protein factors that bind promoter control elements. Fragments of the instant promoters can be used to identify the location of promoter control elements. Another option for obtaining a promoter control element with desired properties is to modify known promoter sequences. This is based on the fact that the function of a promoter is dependent on the interplay of regulatory proteins that bind to specific, discrete nucleotide sequences in the promoter, termed motifs. Such interplay subsequently affects the general transcription machinery and regulates transcription efficiency. These proteins are positive regulators or negative regulators (repressors), and one protein can have a dual role depending on the context (Johnson, P. F. and McKnight, S. L. (1989) Annu. Rev. Biochem. 58:799-839).

One type of in-vitro assay utilizes a known DNA binding factor to isolate DNA fragments that bind. If a fragment or promoter variant does not bind, then a promoter control element has been removed or disrupted. For specific assays, see, for instance, B. Luo et al., *J. Mol. Biol.* 266:470 (1997), S. Chusacultanachai et al., *J. Biol. Chem.* 274:23591 (1999), D. Fabbro et al., *Biochem. Biophys. Res. Comm.* 213:781 (1995)).

Alternatively, a fragment of DNA suspected of conferring a particular pattern of specificity can be examined for activity in binding transcription factors involved in that specificity by methods such as DNA footprinting (e.g. D. J. Cousins et al., *Immunology* 99:101 (2000); V. Kolla et al., *Biochem. Biophys. Res. Comm.* 266:5 (1999)) or "mobility-shift" assays (E. D. Fabiani et al., *J. Biochem.* 347:147 (2000); N. Sugiura et al., *J. Biochem* 347:155 (2000)) or fluorescence polarization (e.g. Royer et al., U.S. Pat. No. 5,445,935). Both mobility shift and DNA footprinting assays can also be used to identify portions of large DNA fragments that are bound by proteins in unpurified transcription extracts prepared from tissues or organs of interest.

Cell-free transcription extracts can be prepared and used to directly assay in a reconstitutable system (Narayan et al., *Biochemistry* 39:818 (2000)).

In-Vivo Assays

Promoter control elements can be identified with reporter genes in in-vivo assays with the use of fragments of the instant promoters or variants of the instant promoter polynucleotides.

For example, various fragments can be inserted into a vector, comprising a basal or "core" promoter, for example, operably linked to a reporter sequence, which, when transcribed, can produce a detectable label. Examples of reporter genes include those encoding luciferase, green fluorescent protein, GUS, neo, cat and bar. Alternatively, reporter sequence can be detected utilizing AFLP and microarray techniques.

In promoter probe vector systems, genomic DNA fragments are inserted upstream of the coding sequence of a reporter gene that is expressed only when the cloned fragment contains DNA having transcription modulation activity (Neve, R. L. et al. (1979) Nature 277:324-325). Control elements are disrupted when fragments or variants lacking any transcription modulation activity. Probe vectors have been designed for assaying transcription modulation in *E. coli* (An, G. et al. (1979) J. Bact. 140:400-407) and other bacterial hosts (Band, L. et al. (1983) Gene 26:313-315; Achen, M. G., Gene 45:45-49 (1986)), yeast (Goodey, A. R. et al. (1986) Mol. Gen. Genet. 204:505-511) and mammalian cells (Pater, M. M. et al. (1984) J. Mol. App. Gen. 2:363-371).

A different design of a promoter/control element trap includes packaging into retroviruses for more efficient delivery into cells. One type of retroviral enhancer trap was described by von Melchner et al. (Genes Dev. 1992; U.S. Pat. No. 5,364,783). The basic design of this vector includes a reporter protein coding sequence engineered into the U3 portion of the 3' LTR. No splice acceptor consensus sequences are included, limiting its utility to work as an enhancer trap only. A different approach to a gene trap using retroviral vectors was pursued by Friedrich and Soriano (Genes Dev. 1991), who engineered a lacZ-neo fusion protein linked to a splicing acceptor. LacZ-neo fusion protein expression from trapped loci allows not only for drug selection, but also for visualization of β-galatactosidase expression using the chromogenic substrate, X-gal.

A general review of tools for identifying transcriptional regulatory regions of genomic DNA is provided by J. W. Fickett et al. (2000) (*Curr. Opn. Biotechnol.* 11:19).

(4) Non-Natural Control Elements

Non-natural control elements can be constructed by inserting, deleting or substituting nucleotides into the promoter control elements described above. Such control elements are capable of transcription modulation that can be determined using any of the assays described above.

D. Constructing Promoters with Control Elements (1) Combining Promoters and Promoter Control Elements The promoter polynucleotides and promoter control elements of the present invention, both naturally occurring and synthetic, can be combined with each other to produce the desired preferential transcription. Also, the polynucleotides of the invention can be combined with other known sequences to obtain other useful promoters to modulate, for example, tissue transcription specific or transcription specific to certain conditions. Such preferential transcription can be determined using the techniques or assays described above.

Fragments, variants, as well as the full-length sequences of SEQ ID NOs: 1-46 and relatives are useful alone or in combination.

The location and relation of promoter control elements within a promoter can affect the ability of the promoter to modulate transcription. The order and spacing of control elements is a factor when constructing promoters.

(2) Number of Promoter Control Elements

Promoters can contain any number of control elements. For example, a promoter can contain multiple transcription binding sites or other control elements. One element may confer tissue or organ specificity; another element may limit transcription to specific time periods, etc. Typically, promoters will contain at least a basal or core promoter as described above. Any additional element can be included as desired. For example, a fragment comprising a basal or "core" promoter can be fused with another fragment with any number of additional control elements.

(3) Spacing Between Control Elements

Spacing between control elements or the configuration or control elements can be determined or optimized to permit the desired protein-polynucleotide or polynucleotide interactions to occur.

For example, if two transcription factors bind to a promoter simultaneously or relatively close in time, the binding sites are spaced to allow each factor to bind without steric hinderance. The spacing between two such hybridizing control elements can be as small as a profile of a protein bound to a control element. In some cases, two protein binding sites can be adjacent to each other when the proteins bind at different times during the transcription process.

Further, when two control elements hybridize the spacing between such elements will be sufficient to allow the promoter polynucleotide to hairpin or loop to permit the two elements to bind. The spacing between two such hybridizing control elements can be as small as a t-RNA loop, to as large as 10 kb.

Typically, the spacing is no smaller than 5 bases; more typically, no smaller than 8; more typically, no smaller than 15 bases; more typically, no smaller than 20 bases; more typically, no smaller than 25 bases; even more typically, no more than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

Such spacing between promoter control elements can be determined using the techniques and assays described above.

(4) Other Promoters

The following are promoters are induced under stress conditions and can be combined with those of the present invention: ldh1 (oxygen stress; tomato; see Germain and Ricard. 1997. Plant Mol Biol 35:949-54), GPx and CAT (oxygen stress; mouse; see Franco et al. (1999) Free Radic Biol Med 27:1122-32), ci7 (cold stress; potato; see Kirch et al. (1997) Plant Mol Biol. 33:897-909), Bz2 (heavy metals; maize; see Marrs and Walbot (1997) Plant Physiol 113:93-102), HSP32 (hyperthermia; rat; see Raju and Maines (1994) Biochim Biophys Acta 1217:273-80); MAPKAPK-2 (heat shock; *Drosophila*; see Larochelle and Suter (1995) Gene 163:209-14).

In addition, the following examples of promoters are induced by the presence or absence of light can be used in combination with those of the present invention: Topoisomerase II (pea; see Reddy et al. (1999) Plant Mol Biol 41:125-37), chalcone synthase (soybean; see Wingender et al. (1989) Mol Gen Genet 218:315-22) mdm2 gene (human tumor; see Saucedo et al. (1998) Cell Growth Differ 9:119-30), Clock and BMAL1 (rat; see Namihira et al. (1999) Neurosci Lett 271:1-4, PHYA (Arabidopsis; see Canton and Quail (1999) Plant Physiol 121:1207-16), PRB-1b (tobacco; see Sessa et al. (1995) Plant Mol Biol 28:537-47) and Ypr10 (common bean; see Walter et al. (1996) Eur J Biochem 239: 281-93).

The promoters and control elements of the following genes can be used in combination with the present invention to confer tissue specificity: MipB (iceplant; Yamada et al. (1995) Plant Cell 7:1129-42) and SUCS (root nodules; broadbean; Kuster et al. (1993) Mol Plant Microbe Interact 6:507-14) for roots, OsSUT1 (rice; Hirose et al. (1997) Plant Cell Physiol 38:1389-96) for leaves, Msg (soybean; Stomvik et al. (1999) Plant Mol Biol 41:217-31) for siliques, cell (Arabidopsis; Shani et al. (1997) Plant Mol Biol 34 (6):837-42) and ACT11 (Arabidopsis; Huang et al. (1997) Plant Mol Biol 33:125-39) for inflorescence.

Still other promoters are affected by hormones or participate in specific physiological processes, which can be used in combination with those of present invention. Some examples are the ACC synthase gene that is induced differently by ethylene and brassinosteroids (mung bean; Yi et al. (1999) Plant Mol Biol 41:443-54), the TAPG1 gene that is active during abscission (tomato; Kalaitzis et al. (1995) Plant Mol Biol 28:647-56), and the 1-aminocyclopropane-1-carboxylate synthase gene (carnation; Jones et al. (1995) Plant Mol Biol 28:505-12) and the CP-2/cathepsin L gene (rat; Kim and Wright (1997) Biol Reprod 57:1467-77), both active during senescence.

E. Vectors

Vectors are a useful component of the present invention. In particular, the present promoters and/or promoter control elements may be delivered to a system such as a cell by way of a vector. For the purposes of this invention, such delivery may range from simply introducing the promoter or promoter control element by itself randomly into a cell to integration of a cloning vector containing the present promoter or promoter control element. Thus, a vector need not be limited to a DNA molecule such as a plasmid, cosmid or bacterial phage that has the capability of replicating autonomously in a host cell. All other manner of delivery of the promoters and promoter control elements of the invention are envisioned. The various T-DNA vector types are a preferred vector for use with the present invention. Many useful vectors are commercially available.

It may also be useful to attach a marker sequence to the present promoter and promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al. (1985) Nature 317: 741-744; Gordon-Kamm et al. (1990) Plant Cell 2: 603-618; and Stalker et al. (1988) Science 242: 419-423). Other marker genes exist which provide hormone responsiveness.

(1) Modification of Transcription by Promoters and Promoter Control Elements

The promoter or promoter control element of the present invention may be operably linked to a polynucleotide to be transcribed. In this manner, the promoter or promoter control element may modify transcription by modulate transcript levels of that polynucleotide when inserted into a genome.

However, prior to insertion into a genome, the promoter or promoter control element need not be linked, operably or otherwise, to a polynucleotide to be transcribed. For example, the promoter or promoter control element may be inserted alone into the genome in front of a polynucleotide already present in the genome. In this manner, the promoter or promoter control element may modulate the transcription of a polynucleotide that was already present in the genome. This polynucleotide may be native to the genome or inserted at an earlier time.

Alternatively, the promoter or promoter control element may be inserted into a genome alone to modulate transcription. See, for example, Vaucheret, H et al. (1998) Plant J 16: 651-659. Rather, the promoter or promoter control element may be simply inserted into a genome or maintained extrachromosomally as a way to divert transcription resources of the system to itself. This approach may be used to downregulate the transcript levels of a group of polynucleotide(s).

(2) Polynucleotide to be Transcribed

The nature of the polynucleotide to be transcribed is not limited. Specifically, the polynucleotide may include sequences that will have activity as RNA as well as sequences that result in a polypeptide product. These sequences may include, but are not limited to antisense sequences, ribozyme sequences, spliceosomes, amino acid coding sequences, and fragments thereof.

Specific coding sequences may include, but are not limited to endogenous proteins or fragments thereof, or heterologous proteins including marker genes or fragments thereof.

Promoters and control elements of the present invention are useful for modulating metabolic or catabolic processes. Such processes include, but are not limited to, secondary product metabolism, amino acid synthesis, seed protein storage, oil development, pest defense and nitrogen usage. Some examples of genes, transcripts and peptides or polypeptides participating in these processes, which can be modulated by the present invention: are tryptophan decarboxylase (tdc) and strictosidine synthase (str1), dihydrodipicolinate synthase (DHDPS) and aspartate kinase (AK), 2S albumin and alpha-, beta-, and gamma-zeins, ricinoleate and 3-ketoacyl-ACP synthase (KAS), *Bacillus thuringiensis* (Bt) insecticidal protein, cowpea trypsin inhibitor (CpTI), asparagine synthetase and nitrite reductase. Alternatively, expression constructs can be used to inhibit expression of these peptides and polypeptides by incorporating the promoters in constructs for antisense use, co-suppression use or for the production of dominant negative mutations.

(3) Other Regulatory Elements

As explained above, several types of regulatory elements exist concerning transcription regulation. Each of these regulatory elements may be combined with the present vector if desired.

(4) Other Components of Vectors

Translation of eukaryotic mRNA is often initiated at the codon that encodes the first methionine. Thus, when constructing a recombinant polynucleotide according to the present invention for expressing a protein product, it is preferable to ensure that the linkage between the 3' portion, preferably including the TATA box, of the promoter and the polynucleotide to be transcribed, or a functional derivative thereof, does not contain any intervening codons which are capable of encoding a methionine.

The vector of the present invention may contain additional components. For example, an origin of replication allows for replication of the vector in a host cell. Additionally, homologous sequences flanking a specific sequence allows for specific recombination of the specific sequence at a desired location in the target genome. T-DNA sequences also allow for insertion of a specific sequence randomly into a target genome.

The vector may also be provided with a plurality of restriction sites for insertion of a polynucleotide to be transcribed as well as the promoter and/or promoter control elements of the present invention. The vector may additionally contain selectable marker genes. The vector may also contain a transcriptional and translational initiation region, and a transcriptional and translational termination region functional in the host cell. The termination region may be native with the transcriptional initiation region, may be native with the polynucleotide to be transcribed, or may be derived from another source. Convenient termination regions are available from the Ti-plasmid of *A. tumefaciens*, such as the octopine synthase and nopaline synthase termination regions. See also, Guerineau et al., (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. 1989) Nucleic Acids Res. 17:7891-7903; Joshi et al. (1987) Nucleic Acid Res. 15:9627-9639.

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831 and 5,436,391; see also and Murray et al., (1989) Nucleic Acids Res. 17:477-498.

Additional sequence modifications include elimination of sequences encoding spurious polyadenylation signals, exon intron splice site signals, transposon-like repeats, and other such sequences well characterized as deleterious to expression. The G-C content of the polynucleotide may be adjusted to levels average for a given cellular host, as calculated by reference to known genes expressed in the host cell. The polynucleotide sequence may be modified to avoid hairpin secondary mRNA structures.

A general description of expression vectors and reporter genes can be found in Gruber et al., "Vectors for Plant Transformation, in Methods in Plant Molecular Biology & Biotechnology" in Glich et al., (Eds. pp. 89-119, CRC Press, 1993). Moreover GUS expression vectors and GUS gene cassettes are available from Clonetech Laboratories, Inc., Palo Alto, Calif. while luciferase expression vectors and luciferase gene cassettes are available from Promega Corp. (Madison, Wis.). GFP vectors are available from Aurora Biosciences.

F. Polynucleotide Insertion Into A Host Cell

The polynucleotides according to the present invention can be inserted into a host cell. A host cell includes but is not limited to a plant, mammalian, insect, yeast, and prokaryotic cell, preferably a plant cell.

The method of insertion into the host cell genome is chosen based on convenience. For example, the insertion into the host cell genome may either be accomplished by vectors that integrate into the host cell genome or by vectors which exist independent of the host cell genome.

(1) Polynucleotides Autonomous of the Host Genome

The polynucleotides of the present invention can exist autonomously or independent of the host cell genome. Vectors of these types are known in the art and include, for example, certain type of non-integrating viral vectors, autonomously replicating plasmids, artificial chromosomes, and the like.

Additionally, in some cases transient expression of a polynucleotide may be desired.

(2) Polynucleotides Integrated into the Host Genome

The promoter sequences, promoter control elements or vectors of the present invention may be transformed into host cells. These transformations may be into protoplasts or intact tissues or isolated cells. Preferably expression vectors are introduced into intact tissue. General methods of culturing plant tissues are provided for example by Maki et al. "Procedures for Introducing Foreign DNA into Plants" in Methods in Plant Molecular Biology & Biotechnology, Glich et al. (Eds. pp. 67-88 CRC Press, 1993) and by Phillips et al. "Cell-Tissue Culture and In-Vitro Manipulation" in Corn & Corn Improvement, 3rd Edition 10 Sprague et al. (Eds. pp. 345-387) American Society of Agronomy Inc. et al. 1988.

Methods of introducing polynucleotides into plant tissue include the direct infection or co-cultivation of plant cell with *Agrobacterium tumefaciens*, Horsch et al. (1985) Science, 227:1229. Descriptions of *Agrobacterium* vector systems and methods for *Agrobacterium*-mediated gene transfer provided by Gruber et al. supra.

Alternatively, polynucleotides are introduced into plant cells or other plant tissues using a direct gene transfer method such as microprojectile-mediated delivery, DNA injection, electroporation and the like. More preferably polynucleotides are introduced into plant tissues using the microprojectile media delivery with the biolistic device. See, for example, Tomes et al., "Direct DNA transfer into intact plant cells via microprojectile bombardment" In: Gamborg and Phillips (Eds.) Plant Cell, Tissue and Organ Culture: Fundamental Methods, Springer Verlag, Berlin (1995).

In another embodiment of the current invention, expression constructs can be used for gene expression in callus culture for the purpose of expressing marker genes encoding peptides or polypeptides that allow identification of transformed plants. Here, a promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells can be transferred to callus shoot-inducing or callus root-inducing media. Gene expression will occur in the callus cells developing on the appropriate media: callus root-inducing promoters will be activated on callus root-inducing media, etc. Examples of such peptides or polypeptides useful as transformation markers include, but are not limited to barstar, glyphosate, chloramphenicol acetyltransferase (CAT), kanamycin, spectinomycin, streptomycin or other antibiotic resistance enzymes, green fluorescent protein (GFP), and β-glucuronidase (GUS), etc. Some of the exemplary promoters of the row titled "The predicted promoter sequence" will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art, for example, by the homologous sequences or T-DNA discussed above or using the cre-lox system (A. C. Vergunst et al. (1998) *Plant Mol. Biol.* 38:393).

G. Utility

Common Uses

In yet another embodiment, the promoters of the present invention can be used to further understand developmental mechanisms. For example, promoters that are specifically induced during callus formation, somatic embryo formation, shoot formation or root formation can be used to explore the effects of overexpression, repression or ectopic expression of target genes, or for isolation of trans-acting factors.

The vectors of the invention can be used not only for expression of coding regions but may also be used in exon-trap cloning, or promoter trap procedures to detect differential gene expression in various tissues (see Lindsey et al. (1993) Transgenic Research 2:3347 and Auch & Reth, et al. Nucleic Acids Research, 18: 674).

Entrapment vectors, first described for use in bacteria (Casadaban and Cohen (1979) Proc. Nat. Aca. Sci. U.S.A., 76: 4530; Casadaban et al. (1980) J. Bacteriol., 143: 971) permit selection of insertional events that lie within coding sequences. Entrapment vectors can be introduced into pluripotent ES cells in culture and then passed into the germline via chimeras (Gossler et al. (1989) Science, 244: 463; Skarnes (1990) Biotechnology, 8: 827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene coupled to a reporter gene. The DNA constructs are inserted into a bacterial strain otherwise lacking the metabolic gene, and the resulting bacteria are used to infect the host organism. Only bacteria expressing the metabolic gene survive in the host organism; consequently, inactive constructs can be eliminated by harvesting only bacteria that survive for some minimum period in the host. At the same time, constitutively active constructs can be eliminated by screening only bacteria that do not express the reporter gene under laboratory conditions. The bacteria selected by such a method contain constructs that are selectively induced only during infection of the host. The IVET approach can be modified for use in plants to identify genes induced in either the bacteria or the plant cells upon pathogen infection or root colonization. For information on IVET see the articles by Mahan et al. (1993) Science 259:686-688, Mahan et al. (1995) PNAS USA 92:669-673, Heithoff et al. (1997) PNAS USA 94:934-939, and Wang et al. (1996) PNAS USA. 93:10434.

Constitutive Transcription

Use of promoters and control elements providing constitutive transcription is desired for modulation of transcription in most cells of an organism under most environmental conditions. In a plant, for example, constitutive transcription is useful for modulating genes involved in defense, pest resistance, herbicide resistance, etc.

Constitutive up-regulation and transcription down-regulation is useful for these applications. For instance, genes, transcripts, and/or polypeptides that increase defense, pest and herbicide resistance may require constitutive up-regulation of transcription. In contrast, constitutive transcriptional down-regulation may be desired to inhibit those genes, transcripts, and/or polypeptides that lower defense, pest and herbicide resistance.

Typically, promoter or control elements that provide constitutive transcription produce transcription levels that are statistically similar in many tissues and environmental conditions observed.

Calculation of P-value from the different observed transcript levels is one means of determining whether a promoter or control element is providing constitutive up-regulation. P-value is the probability that the difference of transcript levels is not statistically significant. The higher the P-value, the more likely the difference of transcript levels is not significant. One formula used to calculate P-value is as follows:

$$\int \varphi(x)dx, \text{ integrated from } a \text{ to } \infty,$$

where $\varphi(x)$ is a normal distribution;

where $a = \frac{|Sx-\mu|}{\sigma}$ (all Samples except $Sx$);

where $Sx$ = the intensity of the sample of intrest where $\mu$ = is the average of the intensities of all samples except $Sx$, $$= \frac{\left(\sum S1 \ldots Sn\right) - Sx}{n-1}$$

where $\sigma(S1 \ldots S11$, not including $Sx)$ = the standard deviation of all sample intensities except $Sx$.

The P-value from the formula ranges from 1.0 to 0.0.

Usually, each P-value of the transcript levels observed in a majority of cells, tissues, or organs under various environmental conditions produced by the promoter or control element is greater than $10^{-8}$; more usually, greater than $10^{-7}$; even more usually, greater than $10^{-6}$; even more usually, greater than $10^{-5}$ or $10^{-4}$.

For up-regulation of transcription, promoter and control elements produce transcript levels that are above background of the assay.

Stress Induced Preferential Transcription

Promoters and control elements providing modulation of transcription under oxidative, drought, oxygen, wound, and methyl jasmonate stress are particularly useful for producing host cells or organisms that are more resistant to biotic and abiotic stresses. In a plant, for example, modulation of genes, transcripts, and/or polypeptides in response to oxidative stress can protect cells against damage caused by oxidative agents, such as hydrogen peroxide and other free radicals.

Drought induction of genes, transcripts, and/or polypeptides is useful to increase the viability of a plant, for example, when water is a limiting factor. In contrast, genes, transcripts, and/or polypeptides induced during oxygen stress can help the flood tolerance of a plant.

The promoters and control elements of the present invention can modulate stresses similar to those described in, for example, stress conditions are VuPLD1 (drought stress; Cowpea; see Pham-Thi et al. (1999) Plant Mol Biol 1257-65), pyruvate decarboxylase (oxygen stress; rice; see Rivosal et al. (1997) Plant Physiol. 114 (3): 1021-29) and chromoplast specific carotenoid gene (oxidative stress; *capsicum*; see Bouvier et al. (1998) Journal of Biological Chemistry 273: 30651-59).

Promoters and control elements providing preferential transcription during wounding or induced by methyl jasmonate can produce a defense response in host cells or organisms. In a plant, for example, preferential modulation of genes, transcripts, and/or polypeptides under such conditions is useful to induce a defense response to mechanical wounding, pest or pathogen attack or treatment with certain chemicals.

Promoters and control elements of the present invention also can trigger a response similar to those described for cf9 (viral pathogen; tomato; see O'Donnell et al. (1998) Plant J 14 (1): 137-42), hepatocyte growth factor activator inhibitor type 1 (HAI-1), which enhances tissue regeneration (tissue injury; human; Koono et al. (1999) J Histochem and Cytochem 47: 673-82), copper amine oxidase (CuAO), induced during ontogenesis and wound healing (wounding; chick-pea; Rea et al. (1998) FEBS Letters 437: 177-82), proteinase inhibitor II (wounding; potato; see Pena-Cortes et al. (1988) Planta 174: 84-89), protease inhibitor II (methyl jasmonate; tomato; see Farmer and Ryan (1990) Proc Natl Acad Sci USA 87: 7713-7716) and two vegetative storage protein genes VspA and VspB (wounding, jasmonic acid, and water deficit; soybean; see Mason and Mullet (1990) Plant Cell 2: 569-579).

Up-regulation and transcription down-regulation are useful for these applications. For instance, genes, transcripts, and/or polypeptides that increase oxidative, flood, or drought tolerance may require up-regulation of transcription. In contrast, transcriptional down-regulation may be desired to inhibit those genes, transcripts, and/or polypeptides that lower such tolerance.

Typically, promoter or control elements, which provide preferential transcription in wounding or under methyl jasmonate induction, produce transcript levels that are statistically significant as compared to cell types, organs or tissues under other conditions.

For preferential up-regulation of transcription, promoter and control elements produce transcript levels that are above background of the assay.

Light Induced Preferential Transcription

Promoters and control elements providing preferential transcription when induced by light exposure can be utilized to modulate growth, metabolism, and development; to increase drought tolerance; and decrease damage from light stress for host cells or organisms. In a plant, for example, modulation of genes, transcripts, and/or polypeptides in response to light is useful (1) to increase the photosynthetic rate;

(2) to increase storage of certain molecules in leaves or green parts only, e.g., silage with high protein or starch content;

(3) to modulate production of exogenous compositions in green tissue, e.g., certain feed enzymes;

(4) to induce growth or development, such as fruit development and maturity, during extended exposure to light;

(5) to modulate guard cells to control the size of stomata in leaves to prevent water loss, or (6) to induce accumulation of beta-carotene to help plants cope with light induced stress.

The promoters and control elements of the present invention also can trigger responses similar to those described in: abscisic acid insensitive 3 (ABI3) (dark-grown *Arabidopsis* seedlings, see Rohde et al. (2000) Plant Cell 12: 35-52), asparagine synthetase (pea root nodules, see Tsai and Coruzzi (1990) EMBO J 9: 323-32), mdm2 gene (human tumor; see Saucedo et al. (1998) Cell Growth Differ 9: 119-30).

Up-regulation and transcription down-regulation are useful for these applications. For instance, genes, transcripts, and/or polypeptides that increase drought or light tolerance may require up-regulation of transcription. In contrast, transcriptional down-regulation may be desired to inhibit those genes, transcripts, and/or polypeptides that lower such tolerance.

Typically, promoter or control elements, which provide preferential transcription in cells, tissues or organs exposed to light, produce transcript levels that are statistically significant as compared to cells, tissues, or organs under decreased light exposure (intensity or length of time).

For preferential up-regulation of transcription, promoter and control elements produce transcript levels that are above background of the assay.

Dark Induced Preferential Transcription

Promoters and control elements providing preferential transcription when induced by dark or decreased light intensity or decreased light exposure time can be utilized to time growth, metabolism, and development, to modulate photosynthesis capabilities for host cells or organisms. In a plant, for example, modulation of genes, transcripts, and/or polypeptides in response to dark is useful, for example, (1) to induce growth or development, such as fruit development and maturity, despite lack of light;

(2) to modulate genes, transcripts, and/or polypeptide active at night or on cloudy days; or (3) to preserve the plastid ultra structure present at the onset of darkness.

The present promoters and control elements can also trigger response similar to those described in the section above.

Up-regulation and transcription down-regulation is useful for these applications. For instance, genes, transcripts, and/or polypeptides that increase growth and development may require up-regulation of transcription. In contrast, transcriptional down-regulation may be desired to inhibit those genes, transcripts, and/or polypeptides that modulate photosynthesis capabilities.

Typically, promoter or control elements, which provide preferential transcription under exposure to dark or decrease light intensity or decrease exposure time, produce transcript levels that are statistically significant.

For preferential up-regulation of transcription, promoter and control elements produce transcript levels that are above background of the assay.

Leaf Preferential Transcription

Promoters and control elements providing preferential transcription in a leaf can modulate growth, metabolism, and development or modulate energy and nutrient utilization in host cells or organisms. In a plant, for example, preferential modulation of genes, transcripts, and/or polypeptide in a leaf, is useful, for example, (1) to modulate leaf size, shape, and development;

(2) to modulate the number of leaves; or (3) to modulate energy or nutrient usage in relation to other organs and tissues Up-regulation and transcription down-regulation is useful for these applications. For instance, genes, transcripts, and/or polypeptides that increase growth, for example, may require up-regulation of transcription. In contrast, transcriptional down-regulation may be desired to inhibit energy usage in a leaf to be directed to the fruit instead, for instance.

Typically, promoter or control elements, which provide preferential transcription in the cells, tissues, or organs of a leaf, produce transcript levels that are statistically significant as compared to other cells, organs or tissues.

For preferential up-regulation of transcription, promoter and control elements produce transcript levels that are above background of the assay.

Root Preferential Transcription

Promoters and control elements providing preferential transcription in a root can modulate growth, metabolism, development, nutrient uptake, nitrogen fixation, or modulate energy and nutrient utilization in host cells or organisms. In a plant, for example, preferential modulation of genes, transcripts, and/or in a leaf, is useful (1) to modulate root size, shape, and development;

(2) to modulate the number of roots, or root hairs;

(3) to modulate mineral, fertilizer, or water uptake;

(4) to modulate transport of nutrients; or (4) to modulate energy or nutrient usage in relation to other organs and tissues.

Up-regulation and transcription down-regulation is useful for these applications. For instance, genes, transcripts, and/or polypeptides that increase growth, for example, may require up-regulation of transcription. In contrast, transcriptional down-regulation may be desired to inhibit nutrient usage in a root to be directed to the leaf instead, for instance.

Typically, promoter or control elements, which provide preferential transcription in cells, tissues, or organs of a root, produce transcript levels that are statistically significant as compared to other cells, organs or tissues.

For preferential up-regulation of transcription, promoter and control elements produce transcript levels that are above background of the assay.

Stem/Shoot Preferential Transcription

Promoters and control elements providing preferential transcription in a stem or shoot can modulate growth, metabolism, and development or modulate energy and nutrient utilization in host cells or organisms. In a plant, for example, preferential modulation of genes, transcripts, and/or polypeptide in a stem or shoot, is useful, for example, (1) to modulate stem/shoot size, shape, and development; or (2) to modulate energy or nutrient usage in relation to other organs and tissues Up-regulation and transcription down-regulation is useful for these applications. For instance, genes, transcripts, and/or polypeptides that increase growth, for example, may require up-regulation of transcription. In contrast, transcriptional down-regulation may be desired to inhibit energy usage in a stem/shoot to be directed to the fruit instead, for instance.

Typically, promoter or control elements, which provide preferential transcription in the cells, tissues, or organs of a stem or shoot, produce transcript levels that are statistically significant as compared to other cells, organs or tissues.

For preferential up-regulation of transcription, promoter and control elements produce transcript levels that are above background of the assay.

Fruit and Seed Preferential Transcription

Promoters and control elements providing preferential transcription in a silique or fruit can time growth, development, or maturity; or modulate fertility; or modulate energy and nutrient utilization in host cells or organisms. In a plant, for example, preferential modulation of genes, transcripts, and/or polypeptides in a fruit, is useful (1) to modulate fruit size, shape, development, and maturity;

(2) to modulate the number of fruit or seeds;

(3) to modulate seed shattering;

(4) to modulate components of seeds, such as, storage molecules, starch, protein, oil, vitamins, anti-nutritional components, such as phytic acid;

(5) to modulate seed and/or seedling vigor or viability;

(6) to incorporate exogenous compositions into a seed, such as lysine rich proteins;

(7) to permit similar fruit maturity timing for early and late blooming flowers; or (8) to modulate energy or nutrient usage in relation to other organs and tissues.

Up-regulation and transcription down-regulation is useful for these applications. For instance, genes, transcripts, and/or polypeptides that increase growth, for example, may require up-regulation of transcription. In contrast, transcriptional down-regulation may be desired to inhibit late fruit maturity, for instance.

Typically, promoter or control elements, which provide preferential transcription in the cells, tissues, or organs of siliques or fruits, produce transcript levels that are statistically significant as compared to other cells, organs or tissues.

For preferential up-regulation of transcription, promoter and control elements produce transcript levels that are above background of the assay.

Callus Preferential Transcription

Promoters and control elements providing preferential transcription in a callus can be useful to modulating transcription in dedifferentiated host cells. In a plant transformation, for example, preferential modulation of genes, transcripts, in callus is useful to modulate transcription of a marker gene, which can facilitate selection of cells that are transformed with exogenous polynucleotides.

Up-regulation and transcription down-regulation is useful for these applications. For instance, genes, transcripts, and/or polypeptides that increase marker gene detectability, for example, may require up-regulation of transcription. In contrast, transcriptional down-regulation may be desired to increase the ability of the calluses to later differentiate, for instance.

Typically, promoter or control elements, which provide preferential transcription in callus, produce transcript levels that are statistically significant as compared to other cell types, tissues, or organs. Calculation of P-value from the different observed transcript levels is one means of determining whether a promoter or control element is providing such preferential transcription.

Usually, each P-value of the transcript levels observed in callus as compared to, at least one other cell type, tissue or organ, is less than $10^{-4}$; more usually, less than $10^{-5}$; even more usually, less than $10^{-6}$; even more usually, less than $10^{-7}$ or $10^{-8}$.

For preferential up-regulation of transcription, promoter and control elements produce transcript levels that are above background of the assay.

Flower Specific Transcription

Promoters and control elements providing preferential transcription in flowers can modulate pigmentation; or modulate fertility in host cells or organisms. In a plant, for example, preferential modulation of genes, transcripts, and/or polypeptides in a flower, is useful, (1) to modulate petal color; or (2) to modulate the fertility of pistil and/or stamen.

Up-regulation and transcription down-regulation is useful for these applications. For instance, genes, transcripts, and/or polypeptides that increase pigmentation, for example, may require up-regulation of transcription. In contrast, transcriptional down-regulation may be desired to inhibit fertility, for instance.

Typically, promoter or control elements, which provide preferential transcription in flowers, produce transcript levels that are statistically significant as compared to other cells, organs or tissues.

For preferential up-regulation of transcription, promoter and control elements produce transcript levels that are above background of the assay.

Immature Bud and Inflorescence Preferential Transcription

Promoters and control elements providing preferential transcription in a immature bud or inflorescence can time growth, development, or maturity; or modulate fertility or viability in host cells or organisms. In a plant, for example, preferential modulation of genes, transcripts, and/or polypeptide in a fruit, is useful, (1) to modulate embryo development, size, and maturity;

(2) to modulate endosperm development, size, and composition;

(3) to modulate the number of seeds and fruits; or (4) to modulate seed development and viability.

Up-regulation and transcription down-regulation is useful for these applications. For instance, genes, transcripts, and/or polypeptides that increase growth, for example, may require up-regulation of transcription. In contrast, transcriptional down-regulation may be desired to decrease endosperm size, for instance.

Typically, promoter or control elements, which provide preferential transcription in immature buds and inflorescences, produce transcript levels that are statistically significant as compared to other cell types, organs or tissues.

For preferential up-regulation of transcription, promoter and control elements produce transcript levels that are above background of the assay.

Senescence Preferential Transcription

Promoters and control elements providing preferential transcription during senescence can be used to modulate cell degeneration, nutrient mobilization, and scavenging of free radicals in host cells or organisms. Other types of responses that can be modulated include, for example, senescence associated genes (SAG) that encode enzymes thought to be involved in cell degeneration and nutrient mobilization (Arabidopsis; see Hensel et al. (1993) Plant Cell 5: 553-64), and the CP-2/cathepsin L gene (rat; Kim and Wright (1997) Biol Reprod 57: 1467-77), both induced during senescence.

In a plant, for example, preferential modulation of genes, transcripts, and/or polypeptides during senescencing is useful to modulate fruit ripening.

Up-regulation and transcription down-regulation is useful for these applications. For instance, genes, transcripts, and/or polypeptides that increase scavenging of free radicals, for example, may require up-regulation of transcription. In contrast, transcriptional down-regulation may be desired to inhibit cell degeneration, for instance.

Typically, promoter or control elements, which provide preferential transcription in cells, tissues, or organs during senescence, produce transcript levels that are statistically significant as compared to other conditions.

For preferential up-regulation of transcription, promoter and control elements produce transcript levels that are above background of the assay.

Germination Preferential Transcription

Promoters and control elements providing preferential transcription in a germinating seed can time growth, development, or maturity; or modulate viability in host cells or organisms. In a plant, for example, preferential modulation of genes, transcripts, and/or polypeptide in a germinating seed, is useful, (1) to modulate the emergence of they hypocotyls, cotyledons and radical; or (2) to modulate shoot and primary root growth and development;

Up-regulation and transcription down-regulation is useful for these applications. For instance, genes, transcripts, and/or polypeptides that increase growth, for example, may require up-regulation of transcription. In contrast, transcriptional down-regulation may be desired to decrease endosperm size, for instance.

Typically, promoter or control elements, which provide preferential transcription in a germinating seed, produce transcript levels that are statistically significant as compared to other cell types, organs or tissues.

For preferential up-regulation of transcription, promoter and control elements produce transcript levels that are above background of the assay.

GFP Experimental Procedures and Results

Procedures

The polynucleotide sequences of the present invention are tested for promoter activity using Green Fluorescent Protein (GFP) assays in the following manner.

Figure 1:
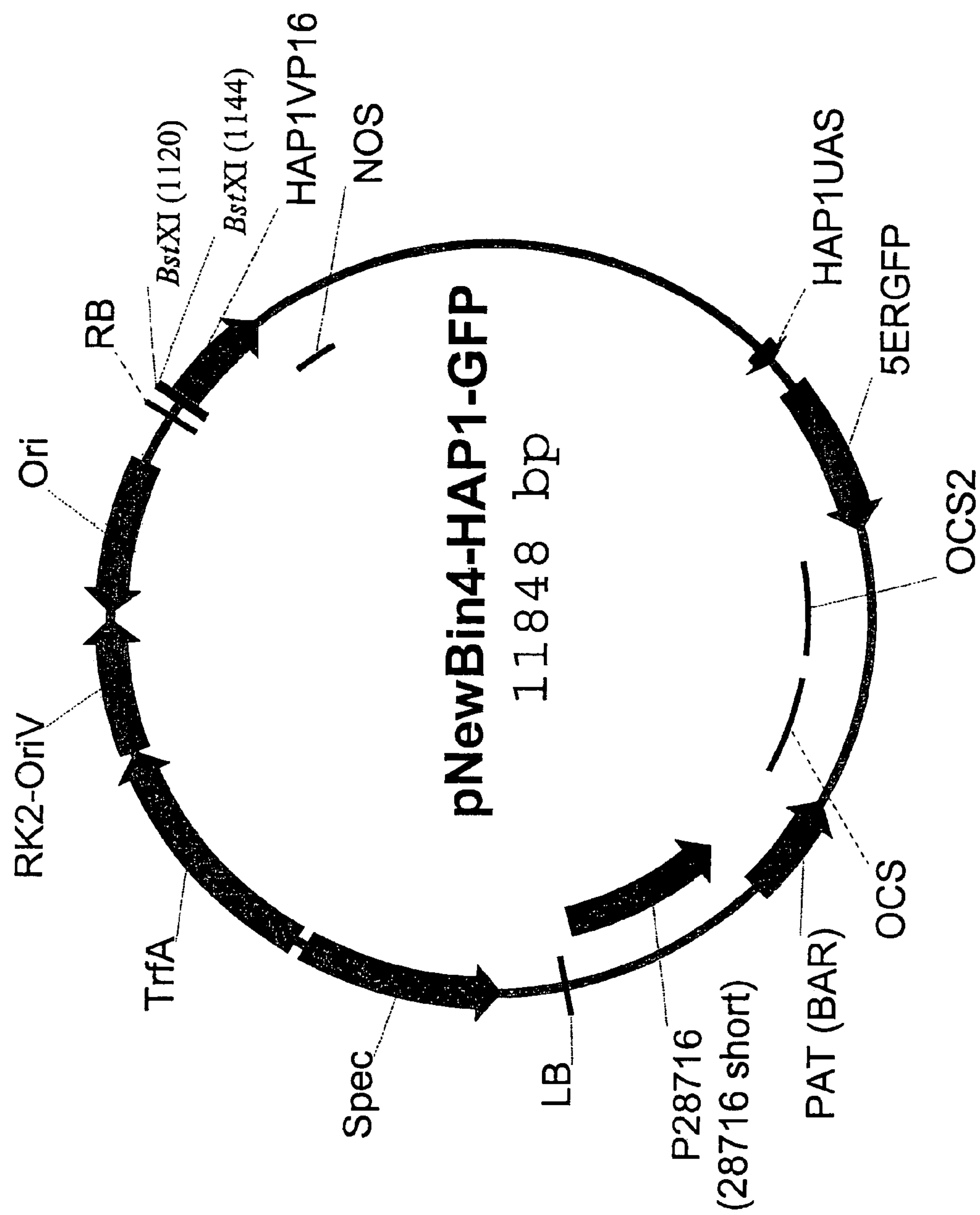
FIG. 1

Approximately 1-2 kb of genomic sequence occurring immediately upstream of the ATG translational start site of the gene of interest is isolated using appropriate primers tailed with BstXI restriction sites. Standard PCR reactions using these primers and genomic DNA are conducted. The resulting product is isolated, cleaved with BstXI and cloned into the BstXI site of an appropriate vector, such as pNewBin4-HAP1-GFP (see FIG. 1).

Transformation

The following procedure is used for transformation of plants

1. Seed Preparation and Plant Growth.

A homogeneous mixture of *Arabidopsis thaliana* seed in a 0.2% Phytagar solution is incubated at 4° C. in the dark for 3 days. Seed is planted in 4 inch pots in a soil mixture of Sunshine Mix, Vermiculite, Marathon and Osmocote. Pots are placed in flats, covered with plastic domes and subsequently subirrigated. After 3 to 4 days, the domes are removed.

Seven to ten days after planting, seedlings are thinned to 20 plants per pot. When 5-10 cm long bolts appear, they are clipped between the first node and the stem base to induce secondary bolts. Six to 7 days after clipping, the plants are transformed via dipping infiltration.

2. Preparation of *Agrobacterium*.

Each 4 inch pot is inverted and the aerial portion of the plants submerged into a 16 oz. polypropylene container holding 200 mls of *Agrobacterium tumefaciens* ($1\times10^7$ bacteria) in Infiltration media (2.2 g MS salts, 50 g sucrose, 110 μg BAP and 0.02% Silwet L-77 per liter). After 5 minutes, the *Agrobacterium* solution is removed while keeping the polypropylene container in place and the pots returned to an upright position. Pots are then placed in flats (10 pots per flat) containing approximately 1 inch of water and covered with shade cloth. After 24 hours, the shade cloth and polypropylene containers are removed.

After flowering, each pot is covered with a ciber plant sleeve. When plants are completely dry, seed is collected and stored.

3. High Throughput Screening—T1 Generation

Transformed seed are placed in pots containing a water saturated soil mixture of Sunshine Mix, Vermiculite, Marathon and Osmocote. Pots are then placed in flats and stored in the dark at 4° C. for at least 2 days. After transferring the flats from the cooler to the greenhouse, they are covered with 55% shade cloth and propagation domes. When the cotyledons are fully expanded the cloth and domes are removed.

Plants are sprayed with a solution of 3 ml concentrated Finale in 48 oz water. Spraying is repeated every 3-4 days until only transformants remain. Transformants are thinned to a maximum of 5 plants per pot.

4. GFP Assay

Tissues are dissected by eye or under magnification using INOX 5 grade forceps and placed on a slide with water and coversliped. An attempt is made to record images of observed expression patterns at earliest and latest stages of development of tissues listed below. Specific tissues will be preceded with High (H), Medium (M), Low (L) designations.

| | |
|---|---|
| Flower | Pedicel, receptacle, nectary, sepal, petal, filament, anther, pollen, carpel, style, papillae, vascular, epidermis, stomata, trichome |
| Silique | Stigma, style, carpel, septum, placentae, transmitting tissue, vascular, epidermis, stomata, abscission zone, ovule |
| Ovule | Pre-fertilization: inner integument, outer integument, embryo sac, funiculus, chalaza, micropyle, gametophyte |
| | Post-fertilization: zygote, inner integument, outer integument, seed coat, primordial, chalaza, miccropyle, early endosperm, mature endosperm, embryo |
| Embryo | Suspensor, preglobular, globular, heart, torpedo, late, mature, provascular, hypophysis, radicle, cotyledons, hypocotyl |
| Stem | Epidermis, cortex, vascular, xylem, phloem, pith, stomata, trichome |
| Leaf | Petiole, mesophyll, vascular, epidermis, trichome, primordial, stomata, stipule, margin |

T1 Mature: These are the T1 plants resulting from independent transformation events. These are screened between stage 6.50-6.90 (means the plant is flowering and that 50-90% of the flowers that the plant will make have developed) which is 4-6 weeks of age. At this stage the mature plant possesses flowers, siliques at all stages of development, and fully expanded leaves. We do not generally differentiate between 6.50 and 6.90 in the report but rather just indicate 6.50. The plants are initially imaged under UV with a Leica Confocal microscope. This allows examination of the plants on a global level. If expression is present, they are imaged using scanning laser confocal micrcopy.

T2 Seedling: Progeny are collected from the T1 plants giving the same expression pattern and the progeny (T2) are sterilized and plated on agar-solidified medium containing M&S salts. In the event that there is no expression in the T1 plants, T2 seeds are planted from all lines. The seedlings are grown in Percival incubators under continuous light at 22° C. for 10-12 days. Cotyledons, roots, hypocotyls, petioles, leaves, and the shoot meristem region of individual seedlings are screened until two seedlings are observed to have the same pattern. Generally found the same expression pattern is found in the first two seedlings. However, up to 6 seedlings are screened before "no expression pattern" is recorded. All constructs are screened as T2 seedlings even if they did not have an expression pattern in the T1 generation.

T2 Mature: The T2 mature plants are screened in a similar manner to the T1 plants. The T2 seeds are planted in the greenhouse, exposed to selection and at least one plant screened to confirm the T1 expression pattern. In instances where there are any subtle changes in expression, multiple plants are examined and the changes noted in the tables.

T3 Seedling: This is done similar to the T2 seedlings except that only the plants for which we are trying to confirm the pattern are planted.

Image Data:

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in Powerpoint specifying organ and specific expressing tissues.

Instrumentation:

An Inverted Leica DM IRB microscope is used with two Fluorescence filter blocks: (1) Blue excitation BP 450-490; long pass emission LP 515 and (2) Green excitation BP 515-560; long pass emission LP 590. The following objectives are used: HC PL FLUOTAR 5×/0.5, HCPL APO 10×/0.4 IMM water/glycerol/oil, HCPL APO 20×/0.7 IMM water/glycerol/oil and HCXL APO 63×/1.2 IMM water/glycerol/oil. A Leica TCS SP2 confocal scanner with a Spectral range of detector optics of 400-850 nm was used with a variable computer controlled pinhole diameter, an Optical zoom 1-32× and four simultaneous detectors: three channels for collection of fluorescence or reflected light and one channel for transmitted light detector. The laser sources are: (1) Blue Ar 458/5 mW, 476 nm/5 mW, 488 nm/20 mW, 514 nm/20 mW, (2) Green HeNe 543 nm/1.2 mW and (3) Red HeNe 633 nm/10 mW.

EXAMPLES

The Examples are organized by an Expression Report for each of the promoters of the invention. They provide the details for expression driven by each of the nucleic acid promoter sequences as observed in transgenic plants. The results are presented as summaries of the spatial expression, which provides information as to gross and/or specific expression in various plant organs and tissues. The observed expression pattern is also presented, which gives details of expression during different generations or different developmental stages within a generation. Additional information is provided regarding the associated gene, the GenBank reference, the source organism of the promoter, and the vector and marker genes used for the construct. The following symbols are used consistently throughout:

T1: First generation transformant

T2: Second generation transformant

T3: Third generation transformant (L): low expression level (M): medium expression level (H): high expression level

Example 1

| Promoter Expression Report # 132 | |
|---|---|
| Promoter Tested In: | *Arabidopsis thaliana*, Wassilewskija (WS) ecotype |
| Spatial expression summary: | |
| Flower | H pollen |
| Silique | H pollen tube H transmitting tissue |
| Primary Root | L epidermis |
| Observed expression pattern: | |
| T1 mature: | Highly specific GFP expression in mature pollen, hydration tube, attachment site and germinating pollen tubes along placenta. |
| T2 seedling: | Weak epidermal expression at root transition zone. |
| Expected expression pattern: | Inducible promoter - induced by different forms of stress (e.g., drought, heat, cold). |
| Selection Criteria: | Microarray |
| Gene: | FAD-linked oxidoreductase family |
| GenBank: | NM_101049 *Arabidopsis thaliana* FAD-linked oxidoreductase family (At1g11770) mRNA, complete cds gi\|18391313\|ref\|NM_101049.1\|[18391313] |
| Source Promoter Organism: | *Arabidopsis thaliana*, Ws |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed.

| Treatment: | Age: | Gen: | Time points: | Events Screened/ Response | Response: |
|---|---|---|---|---|---|
| 1. Cold | 4 wks | T2 | 2 Hr | 2/0 | No |
| | | | 24 Hr post 2 Hr 4 C. | 2/0 | No |
| 2. Heat | 4 wks | T2 | 2 Hr | 2/0 | No |
| | | | 6 Hr | 2/0 | No |
| | | | 24 Hr post 2 Hr 42 C. | 2/0 | No |
| 3. Drought | 4 wks | T2 | 3 Hr air dry | 2/0 | No |
| 4. Drought | 4 wks | T2 | 8 days no water | 2/0 | No |

Inducible expression summary:

| Treatment: | Time point induced: | Organs induced: | Tissues induced: |
|---|---|---|---|

| T1 Mature Plant Expression | Organs/Tissues screened |
|---|---|
| Events Screened: n = 3 | Events Expressing: n = 2 |

-continued

| Promoter Expression Report # 132 | |
|---|---|
| GFP expression as shown below | |
| X Flower | □pedicel □receptacle □nectary □sepal □petal □filament □anther H pollen □carpel □style □papillae □vascular □epidermis □stomata □trichome □silique |
| X Silique | □stigma □style □carpel □septum □placentae H transmitting tissue □vascular □epidermis □stomata □abscission zone □ovule H pollen tube |
| □ Ovule | Pre-fertilization: □inner integument □outer integument □embryo sac □funiculus □chalaza □micropyle □gametophyte Post-fertilization: □zygote □ embryo sack □inner integument □outer integument □endothelium □seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| □ Stem | □epidermis □cortex □vascular □xylem □phloem □pith □stomata □trichome |
| □ Leaf | □petiole □mesophyll □vascular □epidermis □trichome □primordia □stomata □stipule □margin |
| □ Shoot apical meristem | □shoot apical meristem □flower primordium |
| T2 Seedling Expression Events Screened: n = 2 | Tissues Screened Events Expressing: n = 2 |
| Seedlings expressing/Seedlings screened | |
| Event-01: 4/6 Event-02: 2/6 | |
| □ Scheduled GFP Expression Detected | |
| □ Hypocotyl | □epidermis □cortex □vascular □xylem □phloem □stomata |
| □ Cotyledon | □mesophyll □vascular □epidermis □margin □stomata □hydathode |
| □ Rosette Leaf | □mesophyll □vascular □epidermis □trichome □petiole □primordia □stomata □stipule □margin □hydathode |
| X Primary Root | L epidermis □trichoblast □atrichoblast □cortex □endodermis □vascular □xylem □phloem □pericycle □quiescent □columella □root cap □root hairs |
| □ Lateral root | □epidermis □trichoblast □atrichoblast □cortex □endodermis □initials □flanking cells □vascular □lateral root cap |
| □ Shoot apical meristem | □shoot apical meristem |
| Promoter utility | |
| Trait Area: | PG&D, water use and efficiency |
| Sub-trait Area: | Drought, heat, yield |
| Utility: | This promoter sequence can be used to modulate fertility under heat or drought conditions. |
| Construct: | YP0390 |
| Promoter candidate I.D: | 11768778 |
| cDNA I.D: | 23495437 |
| Lines expressing: | YP0390-05, -06 |

Example 2

| Promoter Expression Report #176 | |
|---|---|
| Promoter Tested In: | *Arabidopsis thaliana*, Wassilewskija (WS) ecotype |
| Spatial expression summary: | |
| Flower | H pedicel H sepal H petal H filament M carpel M style H epidermis M silique |
| Silique | M style M carpel H epidermis L ovule |
| Ovule | Post-fertilization: L outer integument |
| Embryo | M heart M torpedo M late |
| Stem | H vascular H pith |
| Hypocotyl | H epidermis |

-continued

Promoter Expression Report #176

| | |
|---|---|
| Cotyledon | H epidermis |
| Rosette Leaf | M epidermis |
| Primary Root | M epidermis L root hairs |
| Lateral root | M epidermis |

Observed expression pattern:

| | |
|---|---|
| T1 mature: | GFP expressed throughout mature plant. In the flower, GFP is first expressed in young buds at the pedicles and sepals, later in the mature flower, GFP expression extends to the sepals, petals, and silique. GFP is not expressed in the anthers or stigma. High GFP expression is observed in heart stage through mature embryos. Weak expression in outer integument of some ovules. High GFP expression throughout vascular and pith regions of stem. |
| T2 seedling: | High GFP expression throughout epidermal cells of seedling. No expression in root caps or guard cells. |
| Expected expression pattern: | Shade Induced |
| Selection Criteria: | Microarray |
| Gene: | allergen V5/Tpx-1-related family protein |
| GenBank: | NM_126057 *Arabidopsis thaliana* allergen V5/Tpx-1-related family protein (At5g66590) mRNA, complete cds gi\|30698237\|ref\|NM_126057.2\|[30698237] |
| Source Promoter Organism: | *Arabidopsis thaliana*, Columbia ecotype |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed.

| Treatment: | Age: | Gen: | Time points: | Events Screened/ Response | Response: |
|---|---|---|---|---|---|
| 1. Far red | 7 days | T2 | 1 Hr | 5/0 | No |
| Far $Red_{730}$ = 525 $\mu W/cm^2$ | | | 24 Hr | 5/0 | No |

Inducible expression summary:

| Treatment: | Time point induced: | Organs induced: | Tissues induced: |
|---|---|---|---|
| 1. Far red | 1 Hr, 24 Hr | No differences observed. | |

T1 Mature Plant Expression Organs/Tissues screened
Events Screened: n = 6 Events Expressing: n = 5

GFP Expression Detected

| | |
|---|---|
| X Flower | H pedicel ☐receptacle ☐nectary H sepal H petal H filament ☐anther ☐pollen M carpel M style ☐papillae ☐vascular H epidermis ☐stomata ☐trichome M silique |
| X Silique | ☐stigma M style M carpel ☐septum ☐placentae ☐transmitting tissue ☐vascular H epidermis ☐stomata ☐abscission zone L ovule |
| X Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐ embryo sack ☐inner integument L outer integument ☐endothelium ☐seed coat ☐primordia ☐chalaza ☐micropyle ☐early endosperm ☐mature endosperm ☐embryo |
| X Embryo | ☐suspensor ☐preglobular ☐globular M heart M torpedo M late ☐mature ☐provascular ☐hypophysis ☐radicle ☐cotyledons |
| X Stem | ☐epidermis ☐cortex H vascular ☐xylem ☐phloem H pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

T2 Seedling Expression Tissues Screened
Events Screened: n = 2 Events Expressing: n = 2

Seedlings expressing/Seedlings screened

Event-01: 4(6)
Event-02: 5(6)

GFP Expression Detected

| | |
|---|---|
| X Hypocotyl | H epidermis ☐ cortex ☐vascular ☐xylem ☐phloem ☐stomata |
| X Cotyledon | ☐mesophyll ☐vascular H epidermis ☐margin ☐stomata ☐hydathode |
| X Rosette Leaf | ☐mesophyll ☐vascular M epidermis ☐trichome ☐petiole ☐primordia ☐stomata ☐stipule ☐margin ☐hydathode |

-continued

| Promoter Expression Report #176 | |
|---|---|
| X Primary Root | M epidermis □trichoblast □atrichoblast □ cortex □endodermis □vascular □xylem □phloem □pericycle □quiescent □columella □root cap<br>L root hairs |
| X Lateral root | M epidermis □trichoblast □atrichoblast □cortex □endodermis □initials □flanking cells □vascular □lateral root cap |
| □ Shoot apical meristem | □shoot apical meristem |

| Promoter utility | |
|---|---|
| Trait Area: | PG&D, nutrients, cold |
| Sub-trait Area: | Seed size, nitrogen use efficiency, cold tolerance |
| Utility: | This promoter sequence can be used to modulate seed size, nitrogen use efficiency, and cold tolerance in seedlings. Nitrogen inducible expression in broad range of tissues can be useful for improving tolerance to low nitrogen. |
| Construct: | PT0681 |
| Promoter candidate I.D: | 15295979 |
| cDNA I.D: | 23541268 (12688858) |
| Lines expressing: | PT0681-01, -03, -04, -05, -06 |

Example 3

| Promoter Expression Report #204 | |
|---|---|
| Promoter Tested In: | *Arabidopsis thaliana*, Wassilewskija (WS) ecotype |
| | Spatial expression summary: |
| Cotyledon | M hydathode |
| Primary Root | H epidermis H root hairs |
| | Observed expression pattern: |
| T1 mature: | No expression. |
| T2 seedling: | GFP predominately expressed throughout root epidermal cells. Highest at GFP expression near hypocotyl root transition zone decreasing toward root tip. |
| Expected expression pattern: | Shade Induced |
| Selection Criteria: | Microarray |
| Gene: | zinc finger (CCCH-type) family protein |
| GenBank: | NM_123793 *Arabidopsis thaliana* zinc finger (CCCH-type) family protein (At5g44260) mRNA, complete cds gi\|30694483\|ref\|NM_123793.2\|[30694483] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed.

| Treatment: | Age: | Gen: | Time points: | Events Screened/ Response | Response: |
|---|---|---|---|---|---|
| 1. Far red | 7 days | T2 | 1 Hr | 2/0 | No |
| Far $Red_{730}$ = 525 μW/cm$^2$ | | | 24 Hr | 2/0 | No |

Inducible expression summary:

| Treatment: | Time point induced: | Organs induced: | Tissues induced: |
|---|---|---|---|
| 1. Far red | | No differences observed. | |

Far $Red_{730}$ = 525 μW/cm$^2$

| T1 Mature Plant Expression | Organs/Tissues screened |
|---|---|
| Events Screened: n = 3 | Events Expressing: n = 0 |

No GFP Expression Detected

| T2 Seedling Expression | Tissues Screened |
|---|---|
| Events Screened: n = 2 | Events Expressing: n = 2 |

Seedlings expressing/Seedlings screened

Event-01: 5/6
Event-02: 5/6

-continued

| Promoter Expression Report #204 | |
|---|---|
| GFP Expression Detected | |
| ☐ Hypocotyl | ☐epidermis ☐cortex ☐vascular ☐xylem ☐phloem ☐stomata |
| X Cotyledon | ☐mesophyll ☐vascular ☐epidermis ☐margin ☐stomata M hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | H epidermis ☐trichoblast ☐atrichoblast ☐cortex ☐endodermis ☐vascular ☐xylem ☐phloem ☐pericycle ☐quiescent ☐columella ☐root cap H root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |
| Promoter utility | |
| Trait Area: | Nutrients |
| Sub-trait Area: | Nitrogen |
| Utility: | This promoter sequence can be used to modulate tolerance to high nitrogen. |
| Construct: | PT0675 |
| Promoter candidate I.D: | 15295952 |
| cDNA I.D: | 24418776 (OCKHAM3-CD) |
| Lines expressing: | PT0675-01, -02 |

Example 4

| Promoter Expression Report #234 | |
|---|---|
| Promoter Tested In: | *Arabidopsis thaliana*, Wassilewskija (WS) ecotype |
| Spatial expression summary: | |
| Ovule | Post-fertilization: H chalaza |
| Hypocotyl | H vascular |
| Cotyledon | H vascular |
| Rosette Leaf | H vascular |
| Primary Root | H vascular |
| Observed expression pattern: | |
| T1 mature: | GFP expressed in vascular connective region of mature ovules. |
| T2 seedling: | GFP expression throughout root and cotyledon vasculature. |
| Expected expression pattern: | Drought inducible - Up regulated In Drought Condition. |
| Selection Criteria: | Microarray |
| Gene: | Expressed protein |
| GenBank: | NM__202299 *Arabidopsis thaliana* expressed protein (At1g54575) mRNA, complete cds gi\|42571874\|ref\|NM__202299.1\|[42571874] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling ☐T2 Mature ☐T3 Seedling |

Inductions completed.

| Treatment: | Age: | Gen: | Time points: | Events Screened/ Response | Response: |
|---|---|---|---|---|---|
| 1. Drought | 7 days | T2 | 3 Hrs air dry | 2/0 | No |
| 2. Drought | 21 days | T2 | 8 days no water | 2/0 | No |

Inducible expression summary:

| Treatment: | Time point induced: | Organs induced: | Tissues induced: |
|---|---|---|---|
| 1. Drought | No increased response observed. | | |
| 2. Drought | No increased response observed under drought conditions. However, additional GFP expression observed in epidermis and vasculature of petals in flowers not observed in primary T1 mature aerial tissue screen. | | |

| T1 Mature Plant Expression | Organs/Tissues screened |
|---|---|
| Events Screened: n = 6 | Events Expressing: n = 2 |

-continued

| Promoter Expression Report #234 | |
|---|---|
| GFP Expression Detected | |
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐funiculus ☐transmitting tissue ☐vascular ☐epidermis ☐stomata ☐abscission zone ☐ovule |
| X Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐ embryo sack ☐funiculus ☐inner integument ☐outer integument ☐endothelium ☐seed coat ☐primordia H chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐root meristem ☐shoot meristem |
| ☐ Stem | ☐epidermis ☐cortex ☐interfascicular region ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |
| T2 Seedling Expression Events Screened: n = 3 | Tissues Screened Events Expressing: n = 2 |
| Seedlings expressing/Seedlings screened | |
| Event-04: 0/6<br>Event-05: 5/6<br>Event-06: 4/6 | |
| GFP Expression Detected | |
| X Hypocotyl | ☐epidermis ☐cortex H vascular ☐xylem ☐phloem ☐stomata |
| X Cotyledon | ☐mesophyll H vascular ☐epidermis ☐margin ☐petiole ☐stomata ☐hydathode |
| X Rosette Leaf | ☐mesophyll H vascular ☐epidermis ☐trichome ☐petiole ☐primordia ☐stomata ☐stipule ☐margin ☐hydathode |
| X Primary Root | ☐epidermis ☐trichoblast ☐atrichoblast ☐cortex ☐endodermis H vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |
| Promoter utility | |
| Trait Area: | Source, PG&D, nutrients |
| Sub-trait Area: | Seed size, nutrient use efficiency |
| Utility: | This promoter sequence can be used to modulate: seed size, and nutrient economy. |
| Construct: | PT0698 |
| Promoter candidate I.D: | 15371554 |
| cDNA I.D: | 23549209 |
| Lines expressing: | PT0698-05, -06; Jun. 21, 2004 |

Example 5

| Promoter Expression Report #235 | |
|---|---|
| Promoter Tested In: | *Arabidopsis thaliana*, Wassilewskija (WS) ecotype |
| Spatial expression summary: | |
| Ovule | Post-fertilization: H mature endosperm H embryo |
| Embryo | H radicle |
| Observed expression pattern: | |
| T1 mature: | High specific expression in the cortical root cells of mature embryos and peripheral endosperm of developing seed. |
| T2 seedling: | No expression observed. |

-continued

| Promoter Expression Report #235 | |
|---|---|
| T2 mature: | No expression observed in mature roots. |
| Expected expression pattern: | Drought - Up in drought not up anywhere else. |
| Selection Criteria: | Microarray |
| Gene: | C2 domain-containing protein/GRAM domain-containing protein |
| GenBank: | NM_124396 *Arabidopsis thaliana* C2 domain-containing protein/GRAM domain-containing protein (At5g50170) mRNA, complete cdsgi\|30695850\|ref\|NM_124396.2\| |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | XT1 Mature XT2 Seedling XT2 Mature ☐T3 Seedling |

Inductions completed.

| Treatment: | Age: | Gen: | Time points: | Events Screened/ Response | Response: |
|---|---|---|---|---|---|
| 1. Drought | 7 days | T2 | 3 Hrs air dry | 2/0 | No |
| 2. Drought | 4 wks | T2 | 8 days no water | 2/0 | No |

Inducible expression summary:

| Treatment: | Time point induced: | Organs induced: | Tissues induced: |
|---|---|---|---|

T1 Mature Plant Expression Organs/Tissues screened
Events Screened: n = 2 Events Expressing: n = 2

GFP Expression Detected

| | |
|---|---|
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐funiculus ☐transmitting tissue ☐vascular ☐epidermis ☐stomata ☐abscission zone ☐ovule |
| X Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐embryo sack ☐funiculus ☐inner integument ☐outer integument ☐endothelium ☐seed coat ☐primordia ☐chalaza ☐micropyle ☐early endosperm H mature endosperm H embryo |
| X Embryo | ☐suspensor ☐preglobular ☐globular ☐heart ☐torpedo ☐late ☐mature ☐provascular ☐hypophysis H radicle ☐cotyledons ☐hypocotyl |
| ☐ Stem | ☐epidermis ☐cortex ☐interfascicular region ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

T2 Seedling Expression Tissues Screened
Events Screened: n = 2 Events Expressing: n = 0

Seedlings expressing/Seedlings screened

Event-01: 0/6
Event-02: 0/6

No GFP Expression Detected

Promoter utility

| | |
|---|---|
| Trait Area: | PG&D, Nutrients |
| Sub-trait Area: | Seed size, seed establishment, nitrogen use efficiency |
| Utility: | This promoter sequence can be used to modulate seed size and nutrient economy when coupled with other appropriate promoter gene constructs. |
| Notes: | Nalefski EA, Falke JJ. 1996. The C2 domain calcium-binding motif: structural and functional diversity. Protein Sci. 5: 2375-90. The C2 domain is a Ca(2+)-binding motif of approximately 130 residues identified in the Ca(2+)-dependent isoforms of protein kinase C. Single and multiple copies of C2 domains have been identified in a growing number of eukaryotic signaling proteins that interact with cellular membranes and mediate a broad array of critical intracellular processes, including membrane trafficking, the generation of lipid-second messengers, activation of GTPases, and the control of protein phosphorylation. As a group, C2 domains display the remarkable property of binding a variety of different ligands and substrates, including Ca2+, phospholipids, inositol polyphosphates, and intracellular proteins. Expanding this functional diversity is the fact that not all proteins containing C2 domains are regulated by Ca2+, suggesting that some C2 domains may play a purely structural role or may have lost the ability to bind Ca2+. |

-continued

| Promoter Expression Report #235 | |
|---|---|
| Construct: | PT0708 |
| Promoter candidate I.D: | 15371629 |
| cDNA I.D: | 23509614 |
| Lines expressing: | PT0708-01, -02 |

Example 6

| Promoter Expression Report #236 | |
|---|---|
| Promoter Tested In: | *Arabidopsis thaliana*, Wassilewskija (WS) ecotype |
| | Spatial expression summary: |
| Flower | M vascular |
| Silique | H vascular |
| Ovule | Post-fertilization: H embryo |
| Embryo | H cotyledons |
| Stem | H vascular H pith |
| Leaf | L vascular |
| Cotyledon | H vascular |
| Rosette Leaf | H mesophyll H vascular H epidermis |
| Primary Root | H vascular |
| | Observed expression pattern: |
| T1 mature: | GFP expression in vasculature of silique, petals, leaf and stem. In silique, GFP is expressed in medial and lateral vasculature of carpels. Not observed in reproductive organs. GFP expression specific to vascular and ground tissues of cotyledon in developing embryos. |
| T2 seedling: | High GFP expression throughout emerging rosette leaves and in vasculature of root and cotyledons. |
| Expected expression pattern: | Drought inducible - Up in drought not up anywhere else. |
| Selection Criteria: | Microarray |
| Gene: | Expressed protein |
| GenBank: | NM_121391 *Arabidopsis thaliana* expressed protein (At5g13880) mRNA, complete cds gi\|18417221\|ref\|NM_121391.1\|[18417221] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed.

| Treatment: | Age: | Gen: | Time points: | Events Screened/Response | Response: |
|---|---|---|---|---|---|
| 1. Drought | 7 days | T2 | 3 air dry | 2/1 | Yes |
| 2. Drought | 4 wks | T2 | 8 days no water | 2/1 | Yes |

Inducible expression summary:

| Treatment: | Time point induced: | Organs induced: | Tissues induced: |
|---|---|---|---|
| 1. Drought | 3 air dry | Rosettes leaf | Epidermis |
| 2. Drought | 8 days no water | Inflorescence, Flowers | Pedicles, Vascular, Guard cells, |
| | | Leaf | Vascular, Guard cells |

| T1 Mature Plant Expression | Organs/Tissues screened |
|---|---|
| Events Screened: n = 3 | Events Expressing: n = 2 |

GFP Expression Detected

| | |
|---|---|
| X Flower | □pedicel □receptacle □nectary □sepal □petal □filament □anther □pollen □carpel □style □papillae M vascular □epidermis □stomata □trichome □silique |
| X Silique | □stigma □style □carpel □septum □placentae □funiculus □transmitting tissue H vascular □epidermis □stomata □abscission zone □ovule |
| X Ovule | Pre-fertilization: □primordia □inner integument □outer integument □embryo sac □funiculus □chalaza □micropyle □gametophyte Post-fertilization: □zygote □suspensor □ embryo sack □funiculus □inner integument □outer integument □endothelium □seed coat □primordia □chalaza □micropyle □early endosperm □mature endosperm H embryo |

-continued

| Promoter Expression Report #236 | |
|---|---|
| X Embryo | ☐suspensor ☐preglobular ☐globular ☐heart ☐torpedo ☐late ☐mature ☐provascular ☐hypophysis ☐radicle H cotyledons ☐hypocotyl |
| X Stem | ☐epidermis ☐cortex ☐interfascicular region H vascular ☐xylem ☐phloem H pith ☐stomata ☐trichome |
| X Leaf | ☐petiole ☐mesophyll L vascular ☐epidermis ☐trichome ☐primordia ☐stomata ☐stipule ☐margin |
| ☐ Shoot apical meristem | ☐shoot apical meristem ☐flower primordium |

| T2 Seedling Expression | Tissues Screened |
|---|---|
| Events Screened: n = 2 | Events Expressing: n = 2 |

| Seedlings expressing/Seedlings screened |
|---|
| Event-01: 6/6 |
| Event-02: 1/6 |

| GFP Expression Detected | |
|---|---|
| ☐ Hypocotyl | ☐epidermis ☐cortex ☐vascular ☐xylem ☐phloem ☐stomata |
| X Cotyledon | ☐mesophyll H vascular ☐epidermis ☐margin ☐petiole ☐stomata ☐hydathode |
| X Rosette Leaf | H mesophyll H vascular H epidermis ☐trichome ☐petiole ☐primordia ☐stomata ☐stipule ☐margin ☐hydathode |
| X Primary Root | ☐epidermis ☐trichoblast ☐atrichoblast ☐cortex ☐endodermis H vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

| Promoter utility | |
|---|---|
| Trait Area: | PG&D, water use efficiency |
| Sub-trait Area: | Seed size, drought tolerance |
| Utility: | This promoter sequence can be used to modulate seed size, drought tolerance, and nutrient use efficiency. |
| Construct: | PT0710 |
| Promoter candidate I.D: | 15371635 |
| cDNA I.D: | 23500258 |
| Lines expressing: | PT0710-01, -02 |

Example 7

| Promoter Expression Report #237 | |
|---|---|
| Promoter Tested In: | *Arabidopsis thaliana*, Wassilewskija (WS) ecotype |
| | Spatial expression summary: |
| Flower | H pollen |
| Ovule | Pre-fertilization: H inner integument H outer integument H micropyle<br>Post-fertilization: H inner integument H outer integument H micropyle |
| Rosette Leaf | H mesophyll M epidermis |
| Primary Root | L epidermis |
| | Observed expression pattern: |
| T1 mature: | GFP expression specific to region of pollen and ovules. GFP appears to be expressed in sperm cells and the vegetative nucleus of pollen cells. GFP is highly expressed in the distal cells of the integuments in the region of the micropyle in developing ovules through mature seed. |
| T2 seedling: | GFP expression in epidermal cells of emerging rosette leaves. Low GFP expression in root epidermal cells near transition zone. |
| Expected expression pattern: | Drought inducible - Up in drought not anywhere else. |
| Selection Criteria: | Microarray |
| Gene: | Expressed protein |
| GenBank: | NM_129154 *Arabidopsis thaliana* expressed protein (At2g35950) mRNA, complete cds gi\|18404005\|ref\|NM_129154.1\|[18404005] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling ☐T2 Mature ☐T3 Seedling |

-continued

Promoter Expression Report #237

Inductions completed.

| Treatment: | Age: | Gen: | Time points: | Events Screened/ Response | Response: |
|---|---|---|---|---|---|
| 1. Drought | 7 days | T2 | 3 hours air dry | 2/0 | No |
| 2. Drought | 4 wks | T2 | 8 days no water | 2/0 | No |

Inducible expression summary:

| Treatment: | Time point induced: | Organs induced: | Tissues induced: |
|---|---|---|---|

T1 Mature Plant Expression Organs/Tissues screened
Events Screened: n = 2 Events Expressing: n = 6

GFP Expression Detected

| | |
|---|---|
| X Flower | □pedicel □receptacle □nectary □sepal □petal □filament □anther H pollen □carpel □style □papillae □vascular □epidermis □stomata □trichome □silique |
| □ Silique | □stigma □style □carpel □septum □placentae □funiculus □transmitting tissue □vascular □epidermis □stomata □abscission zone □ovule |
| X Ovule | Pre-fertilization: □primordia H inner integument H outer integument □embryo sac □funiculus □chalaza H micropyle □gametophyte Post-fertilization: □zygote □suspensor □embryo sack □funiculus H inner integument H outer integument □endothelium □seed coat □primordia □chalaza H micropyle □early endosperm □mature endosperm □embryo |
| □ Embryo | □suspensor □preglobular □globular □heart □torpedo □late □mature □provascular □hypophysis □radicle □cotyledons □hypocotyl |
| □ Stem | □epidermis □cortex □interfascicular region □vascular □xylem □phloem □pith □stomata □trichome |
| □ Leaf | □petiole □mesophyll □vascular □epidermis □trichome □primordia □stomata □stipule □margin |
| □ Shoot apical meristem | □shoot apical meristem □flower primordium |

T2 Seedling Expression Tissues Screened
Events Screened: n = 2 Events Expressing: n = 2

Seedlings expressing/Seedlings screened

Event-06: 2/6
Event-09: 4/6

GFP Expression Detected

| | |
|---|---|
| □ Hypocotyl | □epidermis □cortex □vascular □xylem □phloem □stomata |
| □ Cotyledon | □mesophyll □vascular □epidermis □margin □petiole □stomata □hydathode |
| X Rosette Leaf | H mesophyll □vascular M epidermis □trichome □petiole □primordia □stomata □stipule □margin □hydathode |
| X Primary Root | L epidermis □trichoblast □atrichoblast □cortex □endodermis □vascular □xylem □phloem □pericycle □quiescent □columella □root cap □root hairs |
| □ Lateral root | □epidermis □trichoblast □atrichoblast □cortex □endodermis □initials □flanking cells □vascular □lateral root cap |
| □ Shoot apical meristem | □shoot apical meristem |

Promoter utility

| | |
|---|---|
| Trait Area: | PG&D |
| Sub-trait Area: | Seed size |
| Utility: | This promoter sequence can be used to modulate seed size. |
| Construct: | PT0721 |
| Promoter candidate I.D: | 15371677 |
| cDNA I.D: | 23516060 |
| Lines expressing: | PT0721-06, -09 |

Example 8

| Promoter Expression Report #238 | |
|---|---|
| Promoter Tested In: | *Arabidopsis thaliana*, Wassilewskija (WS) ecotype |
| | Spatial expression summary: |
| Flower | H pollen |
| Embryo | H provascular L radicle |
| Leaf | M vascular |
| Hypocotyl | L epidermis |
| Primary Root | L epidermis |
| | Observed expression pattern: |
| T1 mature: | High GFP specificity throughout vasculature of developing embryo. GFP expression also in vasculature of mature leaves. GFP expressed throughout pollen cells. |
| T2 seedling: | Low GFP expression in epidermal cells of hypocotyl. |
| Expected expression pattern: | Drought inducible - Loudest in drought |
| Selection Criteria: | Microarray |
| Gene: | Em-like protein GEA1 (EM1) |
| GenBank: | NM__115040 *Arabidopsis thaliana* Em-like protein GEA1 (EM1) (At3g51810) mRNA, complete cds gi\|30693538\|ref\|NM__115040.2\|[30693538] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | XT1 Mature X T2 Seedling ☐T2 Mature ☐T3 Seedling |

Inductions completed.

| Treatment: | Age: | Gen: | Time points: | Events Screened/ Response | Response: |
|---|---|---|---|---|---|
| 1. Drought | 7 days | T2 | 3 Hrs air dry | 2/0 | No |
| 2. Drought | 4 wks | T2 | 8 days no water | 2/0 | No |

Inducible expression summary:

| Treatment: | Time point induced: | Organs induced: | Tissues induced: |
|---|---|---|---|

T1 Mature Plant Expression Organs/Tissues screened
Events Screened: n = 3 Events Expressing: n = 2

GFP Expression Detected

| | |
|---|---|
| X Flower | ☐pedicel ☐receptacle ☐nectary ☐sepal ☐petal ☐filament ☐anther H pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐funiculus ☐transmitting tissue ☐vascular ☐epidermis ☐stomata ☐abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐embryo sack ☐funiculus ☐inner integument ☐outer integument ☐endothelium ☐seed coat ☐primordia ☐chalaza ☐micropyle ☐early endosperm ☐mature endosperm ☐embryo |
| X Embryo | ☐suspensor ☐preglobular ☐globular ☐heart ☐torpedo ☐late ☐mature H provascular ☐hypophysis L radicle ☐cotyledons ☐hypocotyl |
| ☐ Stem | ☐epidermis ☐cortex ☐interfascicular region ☐vascular ☐xylem ☐phloem ☐pith ☐stomata ☐trichome |
| X Leaf | ☐petiole ☐mesophyll M vascular ☐epidermis ☐trichome ☐primordia ☐stomata ☐stipule ☐margin |
| ☐ Shoot apical meristem | ☐shoot apical meristem ☐flower primordium |

T2 Seedling Expression Tissues Screened
Events Screened: n = 2 Events Expressing: n = 2

Seedlings expressing/Seedlings screened

Event-01: 3/6
Event-02: 4/7

GFP Expression Detected

| | |
|---|---|
| X Hypocotyl | L epidermis ☐cortex ☐vascular ☐xylem ☐phloem ☐stomata |
| ☐ Cotyledon | ☐mesophyll ☐vascular ☐epidermis ☐margin ☐petiole ☐stomata ☐hydathode |

-continued

| Promoter Expression Report #238 | |
|---|---|
| ☐ Rosette Leaf | ☐mesophyll ☐vascular ☐epidermis ☐trichome ☐petiole ☐primordia ☐stomata ☐stipule ☐margin ☐hydathode |
| X Primary Root | L epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

| Promoter utility | |
|---|---|
| Trait Area: | PG&D, water use efficiency |
| Sub-trait Area: | drought tolerance |
| Utility: | This promoter sequence can be used to modulate: reproductive drought |
| Notes: | Vicient CM, Bies-Etheve N, Delseny M. 2000. Changes in gene expression in the leafy cotyledon1 (lec1) and fusca3 (fus3) mutants of *Arabidopsis thaliana* L. J Exp Bot. 5: 995-1003. In lec1-1 seeds, the AtEm1 gene was expressed at a higher level than in the wild type and earlier in development. Transgenic analysis using 5'-promoter deletions demonstrated that at least two regions of AtEm1 gene promoter interact with the LEC1-dependent transcriptional regulatory pathway. In spite of expression of the AtEm1 promoter and accumulation of AtEm1 mRNA, the corresponding Em1 protein does not accumulate in lec1-1 seeds. The ABA inducibility of the AtEm1 promoter was not affected by the lec1 mutation.[Ceres does not see ABA inducibility in our TxP data]. Gaubier P, Raynal M, Hull G, Huestis GM, Grellet F, Arenas C, Pages M, Delseny M. 1993. Two different Em-like genes are expressed in *Arabidopsis thaliana* seeds during maturation Mol Gen Genet. 238: 409-18. Using a radish cDNA probe, we have isolated and characterized two genomic clones from *Arabidopsis thaliana* (GEA1 and GEA6) encoding two different proteins that are homologous to the "Early methionine-labelled" (Em) protein of wheat. GEA1 differs from GEA6 and Em clones of wheat in that a sequence coding for 20 amino acid residues is tandemly repeated 4 times. These two genomic clones correspond to two genes named AtEm1 and AtEm6. GEA1 appears in immature seeds and is maximum in dry seeds. No expression of either gene could be detected in leaf, stem, or floral buds. Expression of both genes could be detected in immature seeds when the siliques were incubated with abscisic acid (ABA), demonstrating that both genes are ABA responsive. However, examination of the 5' upstream region does not reveal any extensive homology, suggesting that regulation of the two genes differs. In situ hybridization with a GEA1 probe demonstrated that the expression of this gene is essentially located in the provascular tissues of the cotyledons and axis of the dry seed as well as in the epiderm and outer layers of the cortex in the embryo axis. |
| Construct: | PT0740 |
| Promoter candidate I.D: | 15371779 |
| cDNA I.D: | 23635276 |
| Lines expressing: | PT0740-11, -12 |

Example 9

| Promoter Expression Report #111 | |
|---|---|
| Promoter Tested In: | *Arabidopsis thaliana*, Wassilewskija (WS) ecotype |
| | Spatial expression summary: |
| Flower | L pedicel L epidermis |
| Stem | L epidermis |
| Hypocotyl | H epidermis |
| Cotyledon | H mesophyll H vascular H epidermis H petiole |
| Rosette Leaf | H epidermis H petiole |
| Primary Root | H epidermis |
| Lateral root | H lateral root cap |
| | Observed expression pattern: |
| T1 mature: | Low epidermal expression in stem and pedicles near inflorescence apical meristem. |
| T2 seedling: | High epidermal expression in cotyledons, petioles of emerging rosette leaves, hypocotyl, and root. Expression observed in vascular and mesophyll cells of cotyledons. |
| Expected expression pattern: | Drought inducible |
| Selection Criteria: | Ceres expression data |
| Gene: | Hypothetical protein |
| GenBank: | NM_102758 *Arabidopsis thaliana* hypothetical protein (At1g30190) mRNA, complete cds gi\|18397396\|ref\|NM_102758.1\|[18397396] |
| Source Promoter Organism: | *Arabidopsis thaliana*, WS ecotype |
| Vector: | pNewbin4-HAP1-GFP |

-continued

Promoter Expression Report #111

Marker Type: GFP-ER
Generation Screened: XT1 Mature XT2 Seedling □T2 Mature □T3 Seedling Inductions completed:

| Treatment: | Age: | Gen: | Time points: | Events Screened/ Response: | Response: |
|---|---|---|---|---|---|
| 1. Drought | 7 days | T2 | 3 Hrs Air dry | 2/0 | No |
| 2. Drought | 4 weeks | T2 | 10-12 day No H20 | 2/2 | Yes |

Inducible expression summary:

| Treatment: | Time point induced: | Organs induced: | Tissues induced: |
|---|---|---|---|
| 2. Drought | 10-12 day No H20 | Flowers | Pedicel, Epidermis |
| | | Siliques | Epidermis |
| | | Leaf | Epidermis, Vascular |
| | | Stem | Epidermis |

T1 Mature Plant Expression Organs/Tissues screened
Events Screened: n = 6 Events Expressing: n = 2

GFP Expression Detected

X Flower L pedicel □receptacle □nectary □sepal □petal □filament □anther □pollen □carpel □style □papillae □vascular L epidermis □stomata □trichome □silique □ Silique □stigma □style □carpel □septum □placentae □transmitting tissue □vascular □epidermis □stomata □abscission zone □ovule □ Ovule Pre-fertilization: □inner integument □outer integument □embryo sac □funiculus □chalaza □micropyle □gametophyte
Post-fertilization: □zygote □embryo sack □inner integument □outer integument □endothelium □seed coat □primordia □chalaza □micropyle □early endosperm □mature endosperm □embryo □ Embryo □suspensor □preglobular □globular □heart □torpedo □late □mature □provascular □hypophysis □radicle □cotyledons □hypocotyl X Stem L epidermis □cortex □vascular □xylem □phloem □pith □stomata □trichome □ Leaf □petiole □mesophyll □vascular □epidermis □trichome □primordia □stomata □stipule □margin □ Shoot apical meristem □shoot apical meristem □flower primordium T2 Seedling Expression Tissues Screened
Events Screened: n = 2 Events Expressing: n = 2

Seedlings expressing/Seedlings screened

Event-04: 6/6
Event-06: 4/6

□ Scheduled
GFP Expression Detected

X Hypocotyl H epidermis □cortex □vascular □xylem □phloem □stomata

X Cotyledon H mesophyll H vascular H epidermis □margin H petiole □stomata □hydathode X Rosette Leaf □mesophyll □vascular H epidermis □trichome H petiole □primordia □stomata □stipule □margin □hydathode X Primary Root H epidermis □trichoblast □atrichoblast □cortex □endodermis □vascular □xylem □phloem □pericycle □quiescent □columella □root cap □root hairs X Lateral root □epidermis □trichoblast □atrichoblast □cortex □endodermis □initials □flanking cells □vascular H lateral root cap □ Shoot apical meristem □Shoot apical meristem Promoter utility Trait Area: Water use efficiency
Sub-trait Area: Drought
Utility: This promoter sequence can be used to improve:
Modulation growth and development. Modulation of nutrient uptake and loading. Expression of nitrate transports and water pumps. Modulation of drought responses, including modulation of water uptake and transport under drought conditions.

-continued

| Promoter Expression Report #111 | |
|---|---|
| | Notes: Candidate to drive genes involved in osmotic stresses such as NCED. Endogenous promoter induced under drought. |
| Construct: | YP0286 |
| Promoter candidate I.D: | 11768589 |
| cDNA I.D: | 12669548 (OCKHAM3-C) |
| Lines expressing: | YP0286-04, -06; Jul. 3, 2003 |

Example 10

| Promoter Expression Report # 112 | |
|---|---|
| Promoter Tested In: | *Arabidopsis thaliana*, Wassilewskija (WS) ecotype |
| Spatial expression summary: | |
| Flower | L anther |
| Ovule | Post-fertilization: L endothelium |
| Cotyledon | H epidermis H petiole |
| Rosette Leaf | H trichome |
| Primary Root | H epidermis H root hairs |
| Observed expression pattern | |
| T1 mature: | Low GFP expression in endothelium cells of mature ovules and stomium region of developing and dehiscencing anthers. Endothelium expression is very weak and may not have been detected by standard screen. Only tissue with visible GFP expression is analyzed by confocal microscopy. This may account for the expressing/screened ratio. Not expressed in pollen. |
| T2 seedling: | High GFP expression specific to epidermal tissues of cotyledons, root and trichomes of rosette leaves. |
| Expected expression pattern: | Drought-inducible |
| Selection Criteria: | Ceres expression data |
| Gene: | phi-1-related protein |
| GenBank: | NM_125822 *Arabidopsis thaliana* phi-1-related protein (At5g64260) mRNA, complete cds gi\|30697983\|ref\|NM_125822.2\|[30697983] "phosphate-responsive 1 family protein" |
| Source Promoter Organism: | *Arabidopsis thaliana*, WS ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed:

| Treatment: | Age: | Gen: | Time points: | Events Screened/ Response | Response: |
|---|---|---|---|---|---|
| 1. Drought | 7 days | T2 | 3 Hrs air dry | 2/0 | No |
| 2. Drought | 4 weeks | T2 | 10-12 days no H20 | 2/0 | No |

Inducible expression summary:

| Treatment: | Time point induced: | Organs induced: | Tissues induced: |
|---|---|---|---|

1. Drought - No differences observed. Images not shown.
2. Drought - No differences observed. Images not shown.

| T1 Mature Plant Expression | Organs/Tissues screened |
|---|---|
| Events Screened: n = 9 | Events Expressing: n = 3 |

GFP Expression Detected

| | |
|---|---|
| X Flower | □pedicel □receptacle □nectary □sepal □petal □filament L anther □pollen □carpel □style □papillae □vascular □epidermis □stomata □trichome □silique |
| □ Silique | □stigma □style □carpel □septum □placentae □transmitting tissue □vascular □epidermis □stomata □abscission zone □ovule |
| X Ovule | Pre-fertilization: □inner integument □outer integument □embryo sac □funiculus □chalaza □micropyle □gametophyte Post-fertilization: □zygote □ embryo sack □inner integument □outer integument L endothelium □seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| □ Stem | □epidermis □cortex □vascular □xylem □phloem □pith □stomata □trichome |

-continued

| Promoter Expression Report # 112 | |
|---|---|
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

T2 Seedling Expression Tissues Screened
Events Screened: n = 9 Events Expressing: n = 3

Seedlings expressing/Seedlings screened

Event-01: 5/6
Event-02: 3/6
Event-03: Not tested

☐ Scheduled
GFP Expression Detected

| | |
|---|---|
| ☐ Hypocotyl | ☐epidermis ☐cortex ☐vascular ☐xylem ☐phloem ☐stomata |
| X Cotyledon | ☐mesophyll ☐vascular H epidermis ☐margin H petiole ☐stomata ☐hydathode |
| X Rosette Leaf | ☐mesophyll ☐vascular ☐epidermis H trichome ☐petiole ☐primordia ☐stomata ☐stipule ☐margin ☐hydathode |
| X Primary Root | H epidermis ☐trichoblast ☐atrichoblast ☐cortex ☐endodermis ☐vascular ☐xylem ☐phloem ☐pericycle ☐quiescent ☐columella ☐root cap H root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

Induction Screens

1. Drought - No differences observed.
2. Drought - No differences observed.

Promoter utility

| | |
|---|---|
| Trait Area: | PG&D |
| Sub-trait Area: | Yield, Germination and mobilization of nutrient reserves |
| Utility: | This promoter sequence can be used to improve: Modulation seed size and seed shape. Modulation of pollen development and dehiscence and engineering of male sterility. Engineering of plant responses to insects and production and loading of volatiles into trichomes and other epidermal cells. Alteration in loading and transport of metabolites from the soil and environment. Protection against insects and microbes. Modulation of root signaling. Drive CDS that can play a role in shade avoidance. |
| Notes: | Endogenous promoter is up-regulated in far red light. |
| Construct: | YP0289 |
| Promoter candidate I.D: | 11768596 |
| cDNA I.D: | 12326995 |
| Lines expressing: | YP0289-03; Jun. 4, 2003, -10, -13 |

Example 11

Promoter Expression Report #125

| | |
|---|---|
| Promoter Tested In: | *Arabidopsis thaliana*, Wassilewskija (WS) ecotype |

Spatial expression summary:

| | |
|---|---|
| Flower | H pedicel H petal H epidermis |
| Silique | H stigma L style L carpel L septum L epidermis |
| Ovule | Post-fertilization: H outer integument |
| Stem | H epidermis H stomata |
| Hypocotyl | H epidermis |
| Cotyledon | H epidermis |
| Rosette Leaf | H epidermis H trichome |

Observed expression pattern:

| | |
|---|---|
| T1 mature: | GFP expression specific to epidermal cell types. High GFP expression in epidermis of stem decreasing toward pedicles and inflorescence apex. In the flower, high expression observed in epidermal cells of petals and stigma, and lower expression in carpels. High expression in outer integuments of maturing ovules. High expression throughout epidermal cells of mature lower stem. |

-continued

| Promoter Expression Report #125 | |
|---|---|
| T2 seedling: | GFP expression specific to epidermal cell types. High expression in epidermis of hypocotyl, cotyledon, and trichomes of rosette leaves. Not detected in root. Expected expression pattern: Drought inducible Selection Criteria: Public reference; Mol Gen Genet. 1993 Apr; 238 (1-2): 17-25. |
| Gene: | Dehydration-induced protein RD22 |
| GenBank: | NM_122472 *Arabidopsis thaliana* dehydration-induced protein RD22 (At5g25610) mRNA, complete cds gi\|30689960\|ref\|NM_122472.2\|[30689960] |
| Source Promoter Organism: | *Arabidopsis thaliana*, WS ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed:

| Treatment: | Age: | Gen: | Time points: | Events Screened/ Response | Response: |
|---|---|---|---|---|---|
| 1. Drought | 7 days | T2 | 3 Hr air dry | 2/2 | Yes |
| 2. ABA | 10 days | T2 | 2 Hr | 2/0 | No |
| 100 uM | | | 6 Hr | 2/0 | |
| 3. Drought | 4 weeks | T2 | 10-12 days no H20 | 2/2 | Yes |

Inducible expression summary:

| Treatment: | Time point induced: | Organs induced: | Tissues induced: |
|---|---|---|---|
| 1. Drought | 3 Hr air dry | Rosette leaf | Epidermal, Vascular |
| 3. Drought | 10-12 days no H20 | Silique, Leaf, Stem | Epidermal |

T1 Mature Plant Expression Organs/Tissues screened
Events Screened: n = 2 Events Expressing: n = 2

GFP Expression Detected

| | |
|---|---|
| X Flower | H pedicel □receptacle □nectary □sepal H petal □filament □anther □pollen □carpel □style □papillae □vascular H epidermis □stomata □trichome □silique |
| X Silique | H stigma L style L carpel L septum □placentae □transmitting tissue □vascular L epidermis □stomata □abscission zone □ovule |
| X Ovule | Pre-fertilization: □inner integument □outer integument □embryo sac □funiculus □chalaza □micropyle □gametophyte Post-fertilization: □zygote □ embryo sack □inner integument H outer integument □endothelium □seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| X Stem | H epidermis □cortex □vascular □xylem □phloem □pith H stomata □trichome |
| □ Leaf | □petiole □mesophyll □vascular □epidermis □trichome □primordia □stomata □stipule □margin |
| □ Shoot apical meristem | □shoot apical meristem □flower primordium |

T2 Seedling Expression Tissues Screened
Events Screened: n = 2 Events Expressing: n = 2

Seedlings expressing/Seedlings screened

Event-01: 1/6
Event-04: 4/6

□ Scheduled
GFP Expression Detected

| | |
|---|---|
| X Hypocotyl | H epidermis □cortex □vascular □xylem □phloem □stomata |
| X Cotyledon | □mesophyll □vascular H epidermis □margin □stomata □hydathode |
| X Rosette Leaf | □mesophyll □vascular H epidermis H trichome □petiole □primordia □stomata □stipule □margin □hydathode |
| □ Primary Root | □epidermis □trichoblast □atrichoblast □cortex □endodermis □vascular □xylem □phloem □pericycle □quiescent □columella □root cap □root hairs |
| □ Lateral root | □epidermis □trichoblast □atrichoblast □cortex □endodermis □initials □flanking cells □vascular □lateral root cap |
| □ Shoot apical meristem | □shoot apical meristem |

-continued

| Promoter Expression Report #125 | |
|---|---|
| Promoter utility | |
| Trait Area: | PG&D, Stress, Nutrients |
| Sub-trait Area: | Drought, heat and cold |
| Utility: | This promoter sequence can be used to improve: Modulation of compatibility/incompatibility. Modulation seed size and seed shape. Modulation of stem size and shape. Protection against insects and microbes. Modulation of ROS signaling. Uptake of nutrients. Modulation of drought responses including leaf and flower wilting, ovule abortion, infertility and seed abortion. Alteration of seed development and shape, attention of seed dormancy and germination. |
| Notes: | Goh CH, Nam HG, Park YS. Stress memory in plants: a negative regulation of stomatal response and transient induction of rd22 gene to light in abscisic acid-entrained Arabidopsis plants. Plant J. 2003 Oct; 36 (2): 240-55. Iwasaki T, Yamaguchi-Shinozaki K, Shinozaki K. Identification of a cis-regulatory region of a gene in *Arabidopsis thaliana* whose induction by dehydration is mediated by abscisic acid and requires protein synthesis. Mol Gen Genet. 1995 May 20; 247 (4): 391-8. Yamaguchi-Shinozaki K, Shinozaki K. The plant hormone abscisic acid mediates the drought-induced expression but not the seed-specific expression of rd22, a gene responsive to dehydration stress in *Arabidopsis thaliana*. Mol Gen Genet. 1993 Apr; 238 (1-2): 17-25. Endogenous promoter is down-regulated in roots and only mildly and inconsistently up-regulated in drought. |
| Construct: | YP0356 |
| Promoter candidate I.D: | 11768602 |
| cDNA I.D: | 12394809 |
| Lines expressing: | YP0356-01, -04; Oct. 16, 2003 |

Example 12

| Promoter Expression Report #126 | |
|---|---|
| Promoter Tested In: | *Arabidopsis thaliana*, Wassilewskija (WS) ecotype |
| Spatial expression summary: | |
| Ovule | Pre-fertilization: H outer integument<br>Post-fertilization: L outer integument L chalaza |
| Hypocotyl | L vascular |
| Primary Root | L epidermis M vascular M pericycle |
| Observed expression pattern: | |
| T1 mature: | GFP expressed in outer integument of developing ovule primordium. Higher integument expression at chalazal pole observed through maturity. |
| T2 seedling: | Medium to low expression in root vascular bundles weakening toward hypocotyl. Weak expression in epidermal cells at root transition zone. |
| Expected expression pattern: | Drought inducible |
| Selection Criteria: | Ceres, Inc. Expression data |
| Gene: | Putative cytochrome P450 |
| GenBank: | NM_112814 *Arabidopsis thaliana* cytochrome P450, putative (At3g19270) mRNA, complete cds gi\|18402178\|ref\|NM_112814.1\|[18402178] |
| Source Promoter Organism: | *Arabidopsis thaliana*, Columbia ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed: Drought, Heat

| Treatment: | Age: | Gen: | Time points: | Events Screened/Response | Response: |
|---|---|---|---|---|---|
| 1. Drought | 4 wks | T2 | 10-12 d. No H20 | 2/0 | No |
| 2. Drought | 7 days | T2 | 3 hrs Air Dry | 2/0 | No |
| 3. Heat | 7 days | T2 | 1 Hr | 2/0 | No |
| 42 C. | | | 4 Hr | 2/0 | No |
| | | | 24 Hr post-treatment | 2/1 | Yes |

Inducible expression summary:

| Treatment: | Time point induced: | Organs induced: | Tissues induced: |
|---|---|---|---|
| 3. Heat | 24 Hr post-treatment | Rosette leaf | Epidermis Vascular |

-continued

Promoter Expression Report #126

T1 Mature Plant Expression Organs/Tissues screened
Events Screened: n = 2 Events Expressing: n = 2

GFP Expression Detected

| | |
|---|---|
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐ovule |
| X Ovule | Pre-fertilization: ☐inner integument H outer integument ☐embryo sac ☐funiculus ☐chalaza ☐micropyle ☐gametophyte Post-fertilization: ☐zygote ☐ embryo sack ☐inner integument L outer integument ☐endothelium ☐seed coat ☐primordia L chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

T2 Seedling Expression Tissues Screened
Events Screened: n = 2 Events Expressing: n = 2

Seedlings expressing/Seedlings screened

Event-01: 3/5
Event-02: 1/6

☐ Scheduled
GFP Expression Detected

| | |
|---|---|
| X Hypocotyl | ☐epidermis ☐cortex L vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | L epidermis ☐trichoblast ☐atrichoblast ☐cortex ☐endodermis M vascular ☐xylem ☐phloem M pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

Promoter utility

| | |
|---|---|
| Trait Area: | Seed Biology, Stress |
| Sub-trait Area: | Seed fill, seed size, stress during seed fill, stress protection, endosperm production |
| Utility: | This promoter sequence can be used to improve: Protection against ovule and seed abortion. Modulation seed size, seed shape. Modulation of endosperm growth and development. Modulation of heat responses and protection against heat stress. Modulation of water and mineral ion uptake and transport. Loading and transport of metabolites into seeds. Modulation of breeding system. |
| Notes: | Heat stress is a major determinant of seed and fruit yield in many crops, and protection against transient heat stress is a primary goal of modern agriculture. This promoter induces in leaves at approximately 24 hour after heat stress. Few promoters of this kind are available at this time. The leaf induction could protect against water loss from the leaf, offering a possibility of protection against heat and drought conditions, which often coincide. Promoter is mildly induced by drought and drought-like conditions. |
| Construct: | YP0374 |
| Promoter candidate I.D: | 11768817 |
| cDNA I.D: | 12370888 |
| Lines expressing: | YP0374-01, -02 |

Example 13

Promoter Expression Report #127

| | |
|---|---|
| Promoter Tested In: | *Arabidopsis thaliana*, Wassilewskija (WS) ecotype |
| | Spatial expression summary: |
| Flower | M sepal M petal M epidermis |
| Hypocotyl | L epidermis L vascular H stomata |
| Cotyledon | M vascular L epidermis |
| Primary Root | M epidermis M vascular M root hairs |
| | Observed expression pattern: |
| T1 mature: | Expressed in epidermal cells of sepals and petals in developing flowers. |
| T2 seedling: | Medium to low expression in epidermal and vascular cells of hypocotyls and cotyledons. Epidermal and vascular expression at root transition zone decreasing toward root tip. |
| Expected expression pattern: | PEG or Osmotic stress-inducible |
| Selection Criteria: | Ceres expression data |
| Gene: | product = "glycine-rich protein", note: unknown protein |
| GenBank: | NM_100587 *Arabidopsis thaliana* glycine-rich protein (At1g07135) mRNA, complete cds gi\|22329385\|ref\|NM_100587.2\|[22329385] |
| Source Promoter Organism: | *Arabidopsis thaliana*, WS ecotype |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed:

| Treatment: | Age: | Gen: | Time points: | Events Screened/ Response | Response: |
|---|---|---|---|---|---|
| 1. Drought | 7 days | T2 | 3 Hrs airy dry | 2/2 | Yes |
| 2. Drought | 4 weeks | T2 | 10-12 days no H20 | 2/2 | Decrease |

Inducible expression summary:

| Treatment: | Time point induced: | Organs induced: | Tissues induced: |
|---|---|---|---|
| 1. Drought | 3 Hrs airy dry | Cotyledons | Epidermis |

Impeded expression summary:

| Treatment: | Time point impeded: | Organs impeded: | Tissues impeded: |
|---|---|---|---|
| 2. Drought | 10-12 days no H20 | Inflorescence meristem | Sepals |
| | | Sepals | Epidermis, Cortex, Vascular |
| | | Stem | Epidermis, Cortex |
| | | Silique | Epidermis, Cortex |

Notes: Decreased levels of GFP were observed in the primary inflorescence shoot meritem. Stems and siliques were taken from top third of mature plants. No expression observed in stems and siliques from bottom half of secondary inflorescence of mature plants. No differences observed between primary and secondary inflorescence meritems.

| T1 Mature Plant Expression | Organs/Tissues screened |
|---|---|
| Events Screened: n = 2 | Events Expressing: n = 2 |

GFP Expression Detected

| | |
|---|---|
| X Flower | ☐pedicel ☐receptacle ☐nectary M sepal M petal ☐filament ☐anther ☐pollen ☐carpel ☐style ☐papillae ☐vascular M epidermis ☐stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐funiculus ☐ovule |
| ☐ Ovule | Pre-fertilization: ☐inner integument ☐outer integument ☐embryo sac ☐funiculus ☐chalaza ☐micropyle ☐gametophyte Post-fertilization: ☐zygote ☐ embryo sack ☐inner integument ☐outer integument ☐funiculus ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

-continued

| Promoter Expression Report #127 | |
|---|---|
| T2 Seedling Expression Tissues Screened<br>Events Screened: n = 2 Events Expressing: n = 2 | |
| Seedlings expressing/Seedlings screened | |
| Event-02: 4/6<br>Event-06: 5/6 | |
| ☐ Scheduled<br>GFP Expression Detected | |
| X Hypocotyl | L epidermis ☐cortex L vascular ☐xylem ☐phloem H stomata |
| X Cotyledon | ☐mesophyll M vascular L epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | M epidermis ☐trichoblast ☐atrichoblast ☐cortex ☐endodermis M vascular ☐xylem ☐phloem ☐pericycle ☐quiescent ☐columella ☐root cap M root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |
| Promoter utility | |
| Trait Area: | Nutrients, Stress |
| Sub-trait Area: | Drought, Nitrogen uptake |
| Utility: | This promoter sequence can be used to improve: Modulation of water and nutrient uptake and seedling establishment. Modulation of plant-microbe interactions. Changes to flower development and structure. Modulation of responses to drought, especially in the flower and inflorescence and in the stigma. Changes in pollination biology and incompatibility upon drought. |
| Notes: | Endogenous promoter is up-regulated under PEG treatment but not with ABA and drought. |
| Construct: | YP0377 |
| Promoter candidate I.D: | 11768593 |
| cDNA I.D: | 13613778 |
| Lines expressing: | YP0377-02, -06; Oct. 16, 2003 |

Example 14

| Promoter Expression Report #128 | |
|---|---|
| Promoter Tested In: | *Arabidopsis thaliana*, Wassilewskija (WS) ecotype |
| Spatial expression summary: | |
| Flower | H pedicel H receptacle H sepal H petal H filament H anther H carpel H style H stigma H epidermis H stomata H silique |
| Silique | H stigma H style H carpel H septum H placentae H epidermis |
| Stem | L epidermis L cortex H stomata |
| Leaf | H mesophyll H epidermis H trichome H stomata |
| Hypocotyl | H epidermis H stomata |
| Cotyledon | H mesophyll H epidermis |
| Rosette Leaf | H mesophyll H epidermis |
| Primary Root | H epidermis |
| Observed expression pattern: | |
| T1 mature: | Vegetative expression. Not expressed in shoot apical meristem, early flower primordia, pollen and ovules. High expression throughout floral organs. High expression in stem guard cells and cortex cells surrounding stomal chamber (see Table 1. FIG.P). Expression throughout placenta and funiculus but not in any ovule tissue. |
| T2 seedling: | Expressed in all tissues near seedling apex increasing toward root. High root epidermis expression. Not expressed in cotyledon and rosette leaf guard cells (Table.2. G, H.). |
| Expected expression pattern: | Drought inducible |
| Selection Criteria: | Ceres, Inc. microarray |
| Gene: | Responsive to Dehydration 20 |
| GenBank: | NM_128898 *Arabidopsis thaliana* RD20 protein (At2g33380) mRNA, complete cds gi\|30685670\|ref\|NM_128898.2\|[30685670] |

-continued

Promoter Expression Report #128

| | |
|---|---|
| Source Promoter Organism: | *Arabidopsis thaliana*, WS ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed:

| Treatment: | Age: | Gen: | Time points: | Events Screened/ Response | Response: |
|---|---|---|---|---|---|
| 1. Drought | 7 days | T2 | 3 hours air dry | 2/2 | Yes |
| 2. Drought | 7 days | T2 | At Wilt | 2/2 | Yes |
| 3. ABA 100 uM | 7 days | T2 | 6 Hrs | 2/2 | Yes |
| 4. Drought | 4 weeks | T2 | 10-12 days no H20 | 2/2 | Yes |

Inducible expression summary:

| Treatment: | Time point induced: | Organs induced: | Tissues induced: |
|---|---|---|---|
| 1. Drought | 3 hours air dry | Cotyledons | Epidermis |
| | | Hypocotyl | Guard cells |
| 2. Drought | At Wilt | Cotyledons | Epidermis |
| | | Root | Epidermis |
| 3. ABA 100 uM | 6 Hrs | Cotyledons, Rosette leaf | Epidermis, Guard cells Mesophyll, Vasculature |
| 4. Drought | 10-12 days no H20 | Roots | Epidermis |
| | | Flower | Silique, Abscission zone |
| | | Silique | Epidermis |
| | | Leaf | Epidermis, mesophyll |
| | | Stem | Cortex, Epidermis |

| T1 Mature Plant Expression | Organs/Tissues screened |
|---|---|
| Events Screened: n = 3 | Events Expressing: n = 3 |

GFP Expression Detected

| | |
|---|---|
| X Flower | H pedicel H receptacle □nectary H sepal H petal H filament H anther □pollen H carpel H style H stigma □vascular H epidermis H stomata □trichome H silique |
| X Silique | H stigma H style H carpel H septum H placentae □funiculus □transmitting tissue □vascular H epidermis □stomata □abscission zone □ovule |
| □ Ovule | Pre-fertilization: □inner integument □outer integument □embryo sac □funiculus □chalaza □micropyle □gametophyte Post-fertilization: □zygote □embryo sack □inner integument □outer integument □funiculus □endothelium □seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| X Stem | L epidermis L cortex □vascular □xylem □phloem □pith H stomata □trichome |
| X Leaf | □petiole H mesophyll □vascular H epidermis H trichome □primordia H stomata □stipule □margin |
| □ Shoot apical meristem | □shoot apical meristem □flower primordium |

| T2 Seedling Expression | Tissues Screened |
|---|---|
| Events Screened: n = 2 | Events Expressing: n = 2 |

Seedlings expressing/Seedlings screened

Event-01: 4/6
Event-04: 5/6

□ Scheduled
GFP Expression Detected

| | |
|---|---|
| X Hypocotyl | H epidermis □cortex □vascular □xylem □phloem H stomata |
| X Cotyledon | H mesophyll □vascular H epidermis □margin □stomata □hydathode |
| X Rosette Leaf | H mesophyll □vascular H epidermis □trichome □petiole □primordia □stomata □stipule □margin □hydathode |

-continued

| Promoter Expression Report #128 | |
|---|---|
| X Primary Root | H epidermis □trichoblast □atrichoblast □cortex □endodermis □vascular □xylem □phloem □pericycle □quiescent □columella □root cap □root hairs |
| □ Lateral root | □epidermis □trichoblast □atrichoblast □cortex □endodermis □initials □flanking cells □vascular □lateral root cap |
| □ Shoot apical meristem | □shoot apical meristem |

| Promoter utility | |
|---|---|
| Trait Area: | Water stress, Seed Biology, PG&D |
| Sub-trait Area: | Drought, Seed fill |
| Utility: | This promoter sequence can be used to improve: Valuable as drought-inducible promoter for yield protection in drought or heat stress conditions. Modulation of plant growth rate and architecture. Modulation of growth and development in absence of effects on reproductive cells. Enhancement of source strength and seed filling. Engineering of male sterility. |
| Notes: | Takahashi S, Katagiri T, Yamaguchi-Shinozaki K, Shinozaki K. An *Arabidopsis* gene encoding a Ca2+-binding protein is induced by abscisic acid during dehydration. Plant Cell Physiol. 2000 Jul; 41(7): 898-903. Yamaguchi-Shinozaki K, Shinozaki K. The plant hormone abscisic acid mediates the drought-induced expression but not the seed-specific expression of rd22, a gene responsive to dehydration stress in *Arabidopsis thaliana*. Mol Gen Genet. 1993 Apr; 238 (1-2): 17-25. Endogenous gene is up-regulated under drought and ABA. |
| Construct: | YP0380 |
| Promoter candidate I.D: | 11768580 |
| cDNA I.D: | 12462179 (OCKHAM3-CD) |
| Lines expressing: | YP0380 -01, -04, -02; Oct. 16, 2003 |

Example 15

| Promoter Expression Report #129 | |
|---|---|
| Promoter Tested In: | *Arabidopsis thaliana*, Wassilewskija (WS) ecotype |
| Spatial expression summary: | |
| Flower | L pedicel H nectary L epidermis |
| Hypocotyl | L vascular |
| Primary Root | H vascular |
| Observed expression pattern: | |
| T1 mature: | High expression in nectary glands of flowers. Low expression in epidermis of pedicels of developing flowers. |
| T2 seedling: | GFP expressed in root and hypocotyl vasculature. |
| Expected expression pattern: | Drought inducible |
| Selection Criteria: | Ceres, Inc. microarray data |
| Gene: | Unknown expressed protein |
| GenBank: | NM_113878 *Arabidopsis thaliana* expressed protein (At3g29575) mRNA, complete cds gi\|30689672\|ref\|NM_113878.3\|[30689672] |
| Source Promoter Organism: | *Arabidopsis thaliana*, Ws ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed:

| Treatment: | Age: | Gen: | Time points: | Events Screened/ Response | Response: |
|---|---|---|---|---|---|
| 1. Drought | 7 days | T2 | 3 hours air dry | 2/0 | No |
| 2. ABA 100 uM | 7 days | T2 | 6 Hrs | 2/1 | Yes |
| 3. Drought | 4 weeks | T2 | 10-12 days no H20 | 2/2 | Yes |

Inducible expression summary:

| Treatment: | Time point induced: | Organs induced: | Tissues induced: |
|---|---|---|---|
| 2. ABA 100 uM* | 6 Hrs | Root | Vasculature |
| 3. Drought | 10-12 days no H20 | Flower | Sepals, Petals, Silques, Pedicles, Nectaries, Abscission zone |

-continued

| Promoter Expression Report #129 | |
|---|---|
| | Silique Carpels, Epidermis, Vascular<br>Leaf Epidermis, Mesophyll, Vascular<br>Stem Vascular, Pith |
| T1 Mature Plant Expression<br>Events Screened: n = 2 | Organs/Tissues screened<br>Events Expressing: n = 2 |

GFP Expression Detected

| | |
|---|---|
| X Flower | L pedicel ☐receptacle H nectary ☐sepal ☐petal ☐filament ☐anther ☐pollen ☐carpel ☐style ☐papillae ☐vascular L epidermis ☐stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte<br>Post-fertilization: ☐zygote ☐ embryo sack ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

| T2 Seedling Expression<br>Events Screened: n = 2 | Tissues Screened<br>Events Expressing: n = 2 |
|---|---|

Seedlings expressing/Seedlings screened

Event-05: 1/6
Event-06: 6/6

☐ Scheduled
GFP Expression Detected

| | |
|---|---|
| X Hypocotyl | ☐epidermis ☐cortex L vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | ☐epidermis ☐trichoblast ☐atrichoblast ☐cortex ☐endodermis H vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐Shoot apical meristem |

Promoter utility

| | |
|---|---|
| Trait Area: | PG&D |
| Sub-trait Area: | Breeding biology |
| Utility: | This promoter sequence can be used to improve: Modulation of plant secondary products including volatiles or fragrances. Useful to drive genes important in insect attraction for stimulation of outbreeding and hybridization. Useful for making flowerless plants. Modulation of drought stress tolerance. Modulation of heat stress tolerance. |
| Notes: | Baum SF, Eshed Y, Bowman JL. The *Arabidopsis* nectary is an ABC-independent floral structure.Development. 2001 Nov; 128(22): 4657-67.<br>Endogenous promoter is up-regulated in drought, ABA and far red light. |
| Construct: | YP0381 |
| Promoter candidate I.D: | 11768582 |
| cDNA I.D: | 12736859 (OCKHAM3-CD) |
| Lines expressing: | YP0381 -05, -06; Oct. 16, 2003 |

Example 16

Promoter Expression Report #130

| | |
|---|---|
| Promoter Tested In: | *Arabidopsis thaliana*, Wassilewskija (WS) ecotype |

Spatial expression summary:

| | |
|---|---|
| Flower | H nectary M sepal M vascular |
| Hypocotyl | L vascular |
| Cotyledon | L vascular |
| Rosette Leaf | L vascular |
| Primary Root | H epidermis H root cap L root hairs |

Observed expression pattern:

| | |
|---|---|
| T1 mature: | Expressed in nectary glands of flowers and vasculature of sepals. |
| T2 seedling: | High GFP expression in root epidermal cells through to root cap. Low GFP expression in vasculature aerial organs. |
| Expected expression pattern: | PEG or Osmotic stress-inducible |
| Selection Criteria: | Ceres, Inc. Expression data |
| Gene: | product = "expressed protein" |
| GenBank: | NM_129727 *Arabidopsis thaliana* expressed protein (At2g41640) mRNA, complete cds gi\|30688728\|ref\|NM_129727.2\|[30688728] |
| Source Promoter Organism: | *Arabidopsis thaliana*, Ws ecotype |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed.

| Treatment: | Age: | Gen: | Time points: | Events Screened/ Response | Response: |
|---|---|---|---|---|---|
| 1. Drought | 7 days | T2 | 3 Hr air dry | 2/0 | No |
| 2. Drought | 4 weeks | T2 | 10-12 days no H20 | 2/0 | No |

Inducible expression summary:

| Treatment: | Time point induced: | Organs induced: | Tissues induced: |
|---|---|---|---|
| 1. Drought | No differences observed. Images not shown. | | |
| 2. Drought | No differences observed. Images not shown. | | |

| T1 Mature Plant Expression | Organs/Tissues screened |
|---|---|
| Events Screened: n = 2 | Events Expressing: n = 2 |

GFP Expression Detected

| | |
|---|---|
| X Flower | ☐pedicel ☐receptacle H nectary M sepal ☐petal ☐filament ☐anther ☐pollen ☐carpel ☐style ☐papillae M vascular ☐epidermis ☐stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte Post-fertilization: ☐zygote ☐ embryo sack ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐ trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

| T2 Seedling Expression | Tissues Screened |
|---|---|
| Events Screened: n = 2 | Events Expressing: n = 2 |

Seedlings expressing/Seedlings screened

Event-04: 5/6
Event-05: 4/6

☐ Scheduled
GFP Expression Detected

-continued

| Promoter Expression Report #130 | |
|---|---|
| X Hypocotyl | □epidermis □cortex L vascular □xylem □phloem □stomata |
| X Cotyledon | □mesophyll L vascular □epidermis □margin □stomata □hydathode |
| X Rosette Leaf | □mesophyll L vascular □epidermis □trichome □petiole □primordia □stomata □stipule □margin □hydathode |
| X Primary Root | H epidermis □trichoblast □atrichoblast □cortex □endodermis □ vascular □xylem □phloem □pericycle □quiescent □columella H root cap L root hairs |
| □ Lateral root | □epidermis □trichoblast □atrichoblast □cortex □endodermis □initials □flanking cells □vascular □lateral root cap |
| □ Shoot apical meristem | □shoot apical meristem |

| Induction Screens | |
|---|---|
| 1. Drought | No differences observed. |
| 2. Drought | No differences observed. |

| Promoter utility | |
|---|---|
| Trait Area: | PGD, Stress |
| Sub-trait Area: | Drought, Root Architecture, Nutrient Uptake |
| Utility: | This promoter sequence can be used to improve: Modification of growth and development, especially of flower development. Improvements to nectary tissue and nectar production, and improvements in insect and pollination (outcrossing) biology. Modulation of water and nutrient uptake, loading and transport. |
| Notes: | Nectaries are secretory structures that produce nectar, a solution composed mainly of sugars. Carpels, stamen, sepals, and nectary vasculature are derived from vascular bundles of the receptacle. Endogenous promoter is down-regulated in shoots, siliques and flowers. |
| Construct: | YP0382 |
| Promoter candidate I.D: | 11768592 |
| cDNA I.D: | 12735575 (OCKHAM3-CD) |
| Lines expressing: | -04, -05 (Oct. 16, 2004) |

Example 17

| Promoter Expression Report #131 | |
|---|---|
| Promoter Tested In: | *Arabidopsis thaliana*, Wassilewskija (WS) ecotype |
| Spatial expression summary: | |
| Flower | H filament H anther H stomata |
| Silique | H ovule |
| Ovule | Post-fertilization: H outer integument H seed coat H chalaza |
| Leaf | L vascular H stomata |
| Primary Root | H epidermis |
| Observed expression pattern: | |
| T1 mature: | Very high GFP expression levels in stamens of developing flowers. Low expression in vasculature of leaves and guard cells throughout plant. High expression in outer integument of ovules and in seed coats. High incidence of aborted ovules. |
| T2 seedling: | Low expression in root epidermal cells. |
| Expected expression pattern: | Drought inducible |
| Selection Criteria: | Ceres, Inc. Expression data |
| Gene: | product = "protein phosphatase 2C (PP2C), putative" |
| GenBank: | NM_125312 *Arabidopsis thaliana* protein phosphatase 2C (PP2C), putative (At5g59220) mRNA, complete cds gi\|30697191\|ref\|NM_125312.2\|[30697191] |
| Source Promoter Organism: | *Arabidopsis thaliana*, Ws |
| Vector: | pNewbin4-HAP1-GFP |
| Marker Type: | GFP-ER |
| Generation Screened: | XT1 Mature XT2 Seedling □T2 Mature □T3 Seedling |

Inductions completed:

| Treatment: | Gen: | Time points: | Events Screened/Response | Response: |
|---|---|---|---|---|
| 1. ABA 100 uM | T2 | 6 Hr | 2/1 | Yes |
| | | 16 Hr post-treatment | 2/2 | Yes |

-continued

Promoter Expression Report #131

| | | | | |
|---|---|---|---|---|
| 2. Drought | T2 | 3 Hr air dry | 2/0 | No |
| 3. Drought | T2 | 10-12 days no H20 | 2/2 | Yes |

Inducible expression summary:

| Treatment: | Time point induced: | Organs induced: | Tissues induced: |
|---|---|---|---|
| 1. ABA 100 uM | 6 Hr | Leaf | Vasculature |
| | 16 Hr post-treatment | Cotyledons | Vasculature, Guard cells |
| | | Hypocotyl | Epidermis, Vasculature |
| | | Leaf | Epidermis, Vasculature, Guard cells |
| 3. Drought | 10-12 days no H20 | Flowers | Sepals, Epidermis, Guard cells |
| | | Leaf | Epidermis, Mesophyll |
| | | Stem | Epidermis |

| T1 Mature Plant Expression | Organs/Tissues screened |
|---|---|
| Events Screened: n = 4 | Events Expressing: n = 2 |

GFP Expression Detected

| | |
|---|---|
| X Flower | □pedicel □receptacle □nectary □sepal □petal H filament H anther □pollen □carpel □style □papillae □vascular □epidermis H stomata □trichome □silique |
| X Silique | □stigma □style □carpel □septum □placentae □transmitting tissue □vascular □epidermis □stomata □abscission zone H ovule |
| X Ovule | Pre-fertilization: □inner integument □outer integument □embryo sac □funiculus □chalaza □micropyle □gametophyte Post-fertilization: □zygote □ embryo sack □funiculus □inner integument H outer integument □endothelium H seed coat □primordia H chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| □ Stem | □epidermis □cortex □vascular □xylem □phloem □pith □stomata □trichome |
| X Leaf | □petiole □mesophyll L vascular □epidermis □trichome □primordia H stomata □stipule □margin |
| □ Shoot apical meristem | □shoot apical meristem □flower primordium |

| T2 Seedling Expression | Tissues Screened |
|---|---|
| Events Screened: n = 2 | Events Expressing: n = 2 |

Seedlings expressing/Seedlings screened

Event-01: 4/6
Event-02: 4/5

□ Scheduled
GFP Expression Detected

| | |
|---|---|
| □ Hypocotyl | □epidermis □cortex □vascular □xylem □phloem □stomata |
| □ Cotyledon | □mesophyll □vascular □epidermis □margin □stomata □hydathode |
| □ Rosette Leaf | □mesophyll □vascular □epidermis □trichome □petiole □primordia □stomata □stipule □margin □hydathode |
| X Primary Root | H epidermis □trichoblast □atrichoblast □cortex □endodermis □vascular □xylem □phloem □pericycle □quiescent □columella □root cap □root hairs |
| □ Lateral root | □epidermis □trichoblast □atrichoblast □cortex □endodermis □initials □flanking cells □vascular □lateral root cap |
| □ Shoot apical meristem | □shoot apical meristem |

Promoter utility

| | |
|---|---|
| Trait Area: | PG&D, Nutrients, Seed Biology |
| Sub-trait Area: | Seed size, heat tolerance, drought |
| Utility: | This promoter sequence can be used to improve: Modulation of seed size and seed shape by transgene-induced alteration of endosperm loading and/or integument growth. Modulation of flower structure and development especially stamen and anther development. Modulation of root growth and improved water and nutrient loading and transport. Engineering of male sterility and manipulation of stamen and anther development. |

-continued

| Promoter Expression Report #131 | |
|---|---|
| | Improved drought and heat stress tolerance. Improved seedling performance in drought and heat stress conditions. Making longer filaments to improve fertility. |
| Notes: | Sulpice R, Tsukaya H, Nonaka H, Mustardy L, Chen TH, Murata N. Enhanced formation of flowers in salt-stressed *Arabidopsis* after genetic engineering of the synthesis of glycine betaine. Plant J. 2003 Oct; 36(2): 165-76. Saez A, Apostolova N, Gonzalez-Guzman M, Gonzalez-Garcia MP, Nicolas C, Lorenzo O, Rodriguez PL. Gain-of-function and loss-of-function phenotypes of the protein phosphatase 2C HAB1 reveal its role as a negative regulator of abscisic acid signalling. Plant J. 2004 Feb; 37(3): 354-369. Tahtiharju S, Palva T. Antisense inhibition of protein phosphatase 2C accelerates cold acclimation in *Arabidopsis thaliana*. Plant J. 2001 May; 26(4): 461-70. Endogenous promoter is induced in drought and drought-like conditions. |
| Construct: | YP0388 |
| Promoter candidate I.D: | 11768590 |
| cDNA I.D: | 13593066 (OCKHAM3-CD) |
| Lines expressing: | YP0388-01, -05; Oct. 24, 2003 |

Example 18

| Promoter Expression Report # 133 | |
|---|---|
| Promoter Tested In: | *Arabidopsis thaliana*, Wassilewskija (WS) ecotype |
| Spatial expression summary: | |
| Flower | H sepal H petal H anther H style |
| Silique | H style H ovule |
| Ovule | Prefertilization: H outer integument<br>Postfertilization: H outer integument L seed coat |
| Leaf | H vascular |
| Primary Root | H epidermis |
| Observed expression pattern: | |
| T1 mature: | High GFP expression in the style, sepals, petals, and anthers in flowers. Expressed in outer integuments of ovule primordia through developing seed stages and in remnants of aborted ovules. High vasculature expression in leaf |
| T2 seedling: | Medium to low root epidermal expression at root transition zone decreasing toward root tip. Specific to epidermal cells flanking lateral roots. |
| Expected expression pattern: | Drought-inducible |
| Selection Criteria: | Ceres expression data |
| Gene: | PAR-related protein |
| GenBank: | NM_124618 *Arabidopsis thaliana* photoassimilate-responsive protein PAR-related protein (At5g52390) mRNA, complete cds gi\|30696178\|ref\|NM_124618.2\|[30696178] |
| Source Promoter Organism: | *Arabidopsis thaliana*, Ws ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed:

| Treatment: | Age: | Gen: | Time points: | Events Screened/ Response | Response: |
|---|---|---|---|---|---|
| 1. Drought | 7 days | T2 | 3 Hrs air dry | 2/0 | No |
| 2. Drought | 4 weeks | T2 | 10-12 days no H20 | 2/2 | Yes |

Inducible expression summary:

| Treatment: | Time point induced: | Organs induced: | Tissues induced: |
|---|---|---|---|
| 2. Drought | 10-12 days no H20 | Flowers | Sepals, Petals, Anthers, Silique |
| | | Silique | Carpels, Epidermis, Cortex |
| | | Leaf | Epidermis, Mesophyll |

| T1 Mature Plant Expression | Organs/Tissues screened |
|---|---|
| Events Screened: n = 4 | Events Expressing: n = 3 |

-continued

| Promoter Expression Report # 133 | |
|---|---|
| GFP Expression Detected | |
| X Flower | □pedicel □receptacle □nectary H sepal H petal □filament H anther □pollen □carpel H style □papillae □vascular □epidermis □stomata □trichome □silique |
| X Silique | □stigma H style □carpel □septum □placentae □funiculus □transmitting tissue □vascular □epidermis □stomata □abscission zone H ovule |
| X Ovule | Pre-fertilization: □inner integument H outer integument □embryo sac □funiculus □chalaza □micropyle □gametophyte<br>Post-fertilization: □zygote □ embryo sack □inner integument H outer integument □funiculus □endothelium L seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| □ Stem | □epidermis □cortex □vascular □xylem □phloem □pith □stomata □trichome |
| X Leaf | □petiole □mesophyll H vascular □epidermis □trichome □primordia □stomata □stipule □margin |
| □ Shoot apical meristem | □shoot apical meristem □flower primordium |
| T2 Seedling Expression Tissues Screened<br>Events Screened: n = 2 Events Expressing: n = 2 | |
| Seedlings expressing/Seedlings screened | |
| Event-01: 2/4<br>Event-02: 5/5 | |
| □ Scheduled<br>GFP Expression Detected | |
| □ Hypocotyl | □epidermis □cortex □vascular □xylem □phloem □stomata |
| □ Cotyledon | □mesophyll □vascular □epidermis □margin □stomata □hydathode |
| □ Rosette Leaf | □mesophyll □vascular □epidermis □trichome □petiole □primordia □stomata □stipule □margin □hydathode |
| X Primary Root | H epidermis □trichoblast □atrichoblast □cortex □endodermis □vascular □xylem □phloem □pericycle □quiescent □columella □root cap □root hairs |
| □ Lateral root | □epidermis □trichoblast □atrichoblast □cortex □endodermis □initials □flanking cells □vascular □lateral root cap |
| □ Shoot apical meristem | □shoot apical meristem |
| Promoter utility | |
| Trait Area: | Abiotic stresses, PG&D |
| Sub-trait Area: | Drought, Root architecture |
| Utility: | This promoter sequence can be used to improve: Modulation self incompatability including gametophytic incompatibility. Modulation of flower development and structure. Modulation of seed size and shape. Altered seed uptake of water and mineral ions and an altered seed dormancy and germination. Modulation of drought responses including leaf and flower wilting, ovule abortion, infertility and seed abortion. |
| Notes: | Fujita K, Okada M, Lei K, Ito J, Ohkura K, Adu-Gyamfi JJ, Mohapatra PK.<br>Effect of P-deficiency on photoassimilate partitioning and rhythmic changes in fruit and stem diameter of tomato (*Lycopersicon esculentum*) during fruit growth.<br>J Exp Bot. 2003 Nov; 54(392): 2519-28.<br>Murillo I, Roca R, Bortolotti C, Segundo BS.<br>Engineering photoassimilate partitioning in tobacco plants improves growth and productivity and provides pathogen resistance.<br>Plant J. 2003 Nov; 36(3): 330-41.<br>The endogenous gene is consistently induced under drought conditions but not surrogate drought treatments. |
| Construct: | YP0396 |
| Promoter candidate I.D: | 11768788 |
| cDNA I.D: | 12646726 |
| Lines expressing: | YP0396-02, -03; Oct. 24, 2003 |

Example 19

Promoter Expression Report # 143

| | |
|---|---|
| Promoter Tested In: | *Arabidopsis thaliana*, Wassilewskija (WS) ecotype |

Spatial expression summary:

| | |
|---|---|
| Primary Root | L epidermis L trichoblast L atrichoblast L root hair |

Observed expression pattern:

| | |
|---|---|
| T1 mature: | No expression. |
| T2 seedling: | Low expression in root epidermal cells at transition zone decreasing to expression in single cells at mid root. |
| Expected expression pattern: | Drought inducible. |
| Selection Criteria: | Ceres, Inc. Expression data |
| Gene: | Unknown protein. |
| GenBank: | NM_101546 *Arabidopsis thaliana* expressed protein (At1g16850) mRNA, complete cds gi\|18394408\|ref\|NM_101546.1\|[18394408] |
| Source Promoter Organism: | *Arabidopsis thaliana*, WS ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed:

| Treatment: | Age: | Gen. | Time points: | Events Screened/Response | Response: |
|---|---|---|---|---|---|
| 1. Drought | 4 wks | T2 | 10-12 d. No H20 | 3/3 | Yes |
| 2. Drought | 7 days | T2 | 3 Hr. Air Dry | 2/0 | No |
| 3. Cold 4 C. | 7 days | T2 | 2 Hr | 0/3 | No |
| | | | 6 Hr. | 0/3 | No |
| | | | 24 Hr post-treatment | 3/2 | Yes |
| 4. ABA 100 um | 7 days | T2 | 6 Hr. | 2/2 | Yes |

Inducible expression summary:

| Treatment: | Time point induced: | Organs induced: | Tissues induced: |
|---|---|---|---|
| 1. Drought | 10-12 d. No H20: | Flowers | Sepals Petals Guard cells |
| 3. Cold 4 C. | 24 Hr post-treatment: | Cotyledons | Epidermis Vascular |
| | | Root | Epidermis Vascular |
| 4. ABA 100 um | 6 Hr | Cotyledons | Vascular |

T1 Mature Plant Expression Organs/Tissues screened
Events Screened: n = 3 Events Expressing: n = 0

No GFP Expression Detected

T2 Seedling Expression Tissues Screened
Events Screened: n = 3 Events Expressing: n = 3

Seedlings expressing/Seedlings screened

Event-01: 3/6
Event-02: 3/6
Event-03: 2/6

□ Scheduled
GFP Expression Detected

| | |
|---|---|
| □ Hypocotyl | □epidermis □cortex □vascular □xylem □phloem □stomata |
| □ Cotyledon | □mesophyll □vascular □epidermis □margin □stomata □hydathode |
| □ Rosette Leaf | □mesophyll □vascular □epidermis □trichome □petiole □primordia □stomata □stipule □margin □hydathode |
| X Primary Root | L epidermis L trichoblast L atrichoblast □cortex □endodermis □vascular □xylem □phloem □pericycle □quiescent □columella □root cap L root hairs |
| □ Lateral root | □epidermis □trichoblast □atrichoblast □cortex □endodermis □initials □flanking cells □vascular □lateral root cap |
| □ Shoot apical meristem | □shoot apical meristem |

Promoter utility

| | |
|---|---|
| Trait Area: | PG&D, Nutrients |
| Sub-trait Area: | Drought, Nutrient uptake |

-continued

| Promoter Expression Report # 143 | |
|---|---|
| Utility: | This promoter sequence can be used to improve: Modulation of root growth rate, size and shape. Modulation of leaf growth, size and shape. Modulation of water and nutrient uptake. Modulation of plant-microbe including plant rhizobium interactions. Useful for making insecticidal proteins for protection against root worm. Modulation of drought responses and protection against drought and desiccation. Modulation of cold stress responses and protection against cold stress. |
| Notes: | This promoter can have multiple utilities, both in plant growth and development and in protection against plant stress. Few promoters of this kind are available at this time. In stress, this promoter can be useful for protecting against drought and cold which are sometimes associated (at high latitude and/or high altitude) and sometimes not associated (in temperate regions), suggesting potentially very versatile utility or protection against abiotic stress. The cold-induction could be very valuable since roots are very sensitive to cold stress. The drought induction in the leaf could protect against water loss through the leaf. Endogenous promoter induced in heat and drought as well as surrogate drought treatments. |
| Construct: | YP0337 |
| Promoter candidate I.D: | 11768598 |
| cDNA I.D: | 12326510 |
| Lines expressing: | YP0337-01, -02, -03; Oct. 16, 2003 |

Example 20

| Promoter Expression Report #144 | |
|---|---|
| Promoter Tested In: | *Arabidopsis thaliana*, Wassilewskija (WS) ecotype |
| | Spatial expression summary: |
| Primary Root | H epidermis H trichoblast H atrichoblast |
| | Observed expression pattern: |
| T1 mature: | No expression. |
| T2 seedling: | Root specific GFP expression. High expression throughout root epidermal cells. |
| Expected expression pattern: | Drought inducible |
| Selection Criteria: | Ceres expression data |
| Gene: | Heat shock transcription factor family |
| GenBank: | NM_113182 *Arabidopsis thaliana* heat shock transcription factor family (At3g22830) |
| Source Promoter Organism: | *Arabidopsis thaliana*, WS ecotype |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed:

| Treatment: | Age: | Gen: | Time points: | Events Screened/ Response | Response: |
|---|---|---|---|---|---|
| 1. Drought | 7 days | T2 | 3 Hrs air dry | 2/0 | No |
| 2. Drought | 4 weeks | T2 | 10-12 days no H20 | 2/2 | Yes |

Inducible expression summary:

| Treatment: | Time point induced: | Organs induced: | Tissues induced: |
|---|---|---|---|
| 1. Drought | 3 Hrs air dry | None detected. | |
| 2. Drought | 10-12 days no H20 | Leaf | Epidermis, Vascular |

| T1 Mature Plant Expression | Organs/Tissues screened |
|---|---|
| Events Screened: n = 3 | Events Expressing: n = 0 |

No GFP Expression Detected

| T2 Seedling Expression | Tissues Screened |
|---|---|
| Events Screened: n = 2 | Events Expressing: n = 2 |

-continued

| Promoter Expression Report #144 | |
|---|---|
| Seedlings expressing/Seedlings screened | |
| Event-01: 4/6<br>Event-02: 3/4 | |
| ☐ Scheduled | |
| GFP Expression Detected | |
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | H epidermis H trichoblast H atrichoblast ☐cortex ☐endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |
| Promoter utility | |
| Trait Area: | PG&D, Nutrients, Stress, Pest Protection |
| Sub-trait Area: | Drought, Nutrient uptake |
| Utility: | This promoter sequence can be used to improve: Modulation of root growth rate, size and shape. Modulation of water and nutrient uptake. Modulation of plant-microbe including plant rhizobium interactions. Useful for making insecticidal proteins for protection against root worm. Protection against drought stress conditions. Protection against heat stress conditions. |
| Notes: | Endogenous promoter up-regulated under drought, heat and PEG. |
| Construct: | YP0384 |
| Promoter candidate I.D: | 11768599 |
| cDNA I.D: | 12730108 (OCKHAM3-CD) |
| Lines expressing: | YP0384-01, -02; Oct. 24, 2003 |

Example 21

| Promoter Expression Report #146 | |
|---|---|
| Promoter Tested In: | *Arabidopsis thaliana*, Wassilewskija (WS) ecotype |
| | Spatial expression summary: |
| Flower | L receptacle |
| Silique | L abscission zone |
| Primary Root | H epidermis |
| | Observed expression pattern: |
| T1 mature: | Weak GFP expression specific to abscission zone of mature flowers. |
| T2 seedling: | Weak expression in root epidermal cells. Expression rapidly decreases from root transition zone to mid root. |
| Expected expression pattern: | Drought inducible |
| Selection Criteria: | Ceres expression data |
| Gene: | Neoxanthin cleavage enzyme |
| GenBank: | NM_112304 *Arabidopsis thaliana* 9-cis-epoxycarotenoid dioxygenase [neoxanthin cleavage enzyme](NC1)(NCED1), putative (At3g14440) mRNA, complete cds |
| Source Promoter Organism: | *Arabidopsis thaliana*, WS ecotype |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed:

| Treatment: | Age: | Gen: | Time points: | Events Screened/ Response | Response: |
|---|---|---|---|---|---|
| 1. Drought | 7 days | T2 | 3 Hr air dry | 2/2 | Yes |
| 2. ABA 100 uM | 7 days | T2 | 6 Hr | 4/1 | Yes |
| 3. Drought | 4 weeks | T2 | 10-12 days no | 2/0 | No |

-continued

| Promoter Expression Report #146 | | | |
|---|---|---|---|
| H20 | | | |
| Inducible expression summary: | | | |
| Treatment: | Time point induced: | Organs induced: | Tissues induced: |
| 1. Drought | 3 Hr air dry | Hypocotyl, Cotyledon, Rosette Leaf, Primary Root | Epidermis, vascular |
| 2. ABA 100 uM | 6 Hr | Cotyledon | Epidermis |
| 3. Drought | 10-12 days no H20 | No differences observed. | |

| T1 Mature Plant Expression | Organs/Tissues screened |
|---|---|
| Events Screened: n = 6 | Events Expressing: n = 3 |

| GFP Expression Detected | |
|---|---|
| X Flower | ☐pedicel L receptacle ☐nectary ☐sepal ☐petal ☐filament ☐anther ☐pollen ☐carpel ☐style ☐papillae ☐vascular ☐epidermis ☐stomata ☐trichome ☐silique |
| X Silique | ☐stigma ☐style ☐carpel ☐septum ☐placentae ☐transmitting tissue ☐vascular ☐epidermis ☐stomata L abscission zone ☐ovule |
| ☐ Ovule | Pre-fertilization: ☐inner integument ☐outer integument ☐embryo sac ☐funiculus ☐chalaza ☐micropyle ☐gametophyte Post-fertilization: ☐zygote ☐ embryo sack ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

| T2 Seedling Expression | Tissues Screened |
|---|---|
| Events Screened: n = 4 | Events Expressing: n = 3 |

Seedlings expressing/Seedlings screened

Event-01: 5/6
Event-02: 5/6

☐ Scheduled

| GFP Expression Detected | |
|---|---|
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | H epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

| Promoter utility | |
|---|---|
| Trait Area: | PG&D, Stress |
| Sub-trait Area: | Flower abscission, Drought |
| Utility: | This promoter sequence can be used to improve: Delaying or accelerating flower abscission in canola. Delaying or accelerating fruit drop. Making flowerless plants. Modulation of water and mineral nutrient uptake. Useful to drive genes important in corn root worm resistance and other interactions involving roots and pests or microbes. Enhanced tolerance of drought conditions. Enhanced tolerance of heat conditions. |
| Notes: | Milborrow BV. The pathway of biosynthesis of abscisic acid in vascular plants: a review of the present state of knowledge of ABA biosynthesis. J Exp Bot. 2001 Jun; 52(359): 1145-64. Review. Qin X, Zeevaart JA. The 9-cis-epoxycarotenoid cleavage reaction is the key regulatory step of abscisic acid biosynthesis in water-stressed bean. |

-continued

| Promoter Expression Report #146 | |
|---|---|
| | Proc Natl Acad Sci USA. 1999 Dec 21; 96(26): 15354-<br>Endogenous promoter generally up-regulated under drought. |
| Construct: | YP0385 |
| Promoter candidate I.D: | 11768579 |
| cDNA I.D: | 12658348 (OCKHAM3-C) |
| Lines expressing: | YP0385-02, -03, -06; Oct. 24, 2004 |

Example 22

| Promoter Expression Report #153 | |
|---|---|
| Promoter Tested In: | *Arabidopsis thaliana*, Wassilewskija (WS) ecotype |
| | Spatial expression summary: |
| Flower | L pedicel L sepal M style M silique |
| Silique | M style M septum |
| Stem | L epidermis L cortex H pith |
| Hypocotyl | L epidermis |
| Cotyledon | L mesophyll L epidermis |
| Primary Root | L epidermis L cortex |
| | Observed expression pattern: |
| T1 mature: | GFP expression in vegetative tissues. Highly expressed in ground tissues of leaf and stem. Not detected in vascular tissue. In flowers, expressed in epidermal cells of sepals and in style-valve margin region of silique. Not expressed in carpels, placenta or ovules. Specific expression localized to group of cells at the junction of the stem and pedicle. |
| T2 seedling: | Expressed throughout epidermal cells of seedling. Also expressed in mesophyll cells of cotyledon, and cortex cells in root. |
| Expected expression pattern: | Drought Inducible |
| Selection Criteria: | Public |
| Gene: | RD29A |
| GenBank: | NM_124610 *Arabidopsis thaliana* low-temperature-responsive protein 78 (LTI78)/desiccation-responsive protein 29A (RD29A) (At5g52310) mRNA, complete cds gi\|306961 |
| Source Promoter Organism: | *Arabidopsis thaliana*, Columbia ecotype |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed:

| Treatment: | Age: | Gen: | Time points: | Events Screened/ Response | Response: |
|---|---|---|---|---|---|
| 1. Drought | 7 days | T2 | 3 Hrs air dry | 2/2 | Yes |
| 2. Drought | 4 weeks | T2 | 10-12 days no H20 | 2/2 | Yes |

Inducible expression summary:

| Treatment: | Time point induced: | Organs induced: | Tissues induced: |
|---|---|---|---|
| 1. Drought | 3 Hrs air dry | Hypocotyl | Epidermis, Vascular |
| | | Rosette Leaf | Trichomes, petiole, vascular |
| 2. Drought | 10-12 days no H20 | Inflorescence meristem | SAM, Flowers, Pedicels |
| | | Flowers | Sepals, Siliques |
| | | Sepals | Epidermis |
| | | Silique | Epidermis, Septum |
| | | Stem | Pith, Vascular |
| | | Leaf | Epidermis, Mesophyll, Vascular |

-continued

| Promoter Expression Report #153 | |
|---|---|
| T1 Mature Plant Expression Events Screened: n = 4 | Organs/Tissues screened Events Expressing: n = 4 |
| GFP Expression Detected | |
| X Flower | L pedicel □receptacle □nectary L sepal □petal □filament □anther □pollen □carpel M style □papillae □vascular □epidermis □stomata □trichome M silique |
| X Silique | □stigma M style □carpel M septum □placentae □funiculus □transmitting tissue □vascular □epidermis □stomata □abscission zone □ovule |
| □ Ovule | Pre-fertilization: □primordia □inner integument □outer integument □embryo sac □funiculus □chalaza □micropyle □gametophyte Post-fertilization: □zygote □suspensor □ embryo sack □inner integument □outer integument □funiculus □endothelium □seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| X Stem | L epidermis L cortex □vascular □xylem □phloem H pith □stomata □trichome |
| □ Leaf | □petiole □mesophyll □vascular □epidermis □trichome □primordia □stomata □stipule □margin |
| □ Shoot apical meristem | □shoot apical meristem □flower primordium |
| T2 Seedling Expression Events Screened: n = 2 # 10 | Tissues Screened Events Expressing: n = 2 |
| Seedlings expressing/Seedlings screened | |
| Event-01: 4/6<br>Event-02: 4/6 | |
| GFP Expression Detected | |
| X Hypocotyl | L epidermis □cortex □vascular □xylem □phloem □stomata |
| X Cotyledon | L mesophyll □vascular L epidermis □margin □stomata □hydathode |
| □ Rosette Leaf | □mesophyll □vascular □epidermis □trichome □petiole □primordia □stomata □stipule □margin □hydathode |
| X Primary Root | L epidermis □trichoblast □atrichoblast L cortex □endodermis □vascular □xylem □phloem □pericycle □quiescent □columella □root cap □root hairs |
| □ Lateral root | □epidermis □trichoblast □atrichoblast □cortex □endodermis □initials □flanking cells □vascular □lateral root cap |
| □ Shoot apical meristem | □shoot apical meristem |
| Promoter utility | |
| Trait Area: | PG&D, Stress, Nutrients |
| Sub-trait Area: | Plant architecture, drought, nitrogen uptake |
| Utility: | This promoter sequence can be used to improve: General alterations in growth and development, including modulation of leaf growth and expansion, root growth elongation, branching patterns and phyllotaxy. Useful in controlling silique shatter and seed dispersal. Modulation of incompatibility, especially gametophytic incompatibility. Protection against drought stress conditions. Protection against heat stress conditions. Modulation of plant responses to abiotic stress. |
| Notes: | Endogenous promoter generally induced under drought and cold. |
| Construct: | PT0633 |
| Promoter candidate I.D: | 11768604 |
| cDNA I.D: | 12328867 (OCKHAM3-CD) |
| Lines expressing: | PT0633 01, 02, 04, 06. |

Example 23

| Promoter Expression Report #156 | |
|---|---|
| Promoter Tested In: | *Arabidopsis thaliana*, Wassilewskija WS ecotype |
| | Spatial expression summary: |
| Flower | H sepal H petal H filament H epidermis L stomata |
| Silique | L stomata |
| Stem | L stomata |
| Hypocotyl | L stomata |
| Cotyledon | L stomata |
| Rosette Leaf | L stomata |
| Primary Root | H epidermis H vascular |
| | Observed expression pattern: |
| T1 mature: | Expressed in second and third whorls of floral organs. High GFP expression in epidermal and vascular tissues of petals and stamens in flowers with expression restricted vasculature in sepals. GFP expression in stamens is localized to filaments and connective tissue between locules of anthers. Guard cell expression throughout floral organs and stem. Expression in siliques restricted to guard cells. |
| T2 seedling: | High GFP expression throughout vasculature and epidermal cells near root transition zone of seedling root. Guard cell expression throughout seedlings. |
| Expected expression pattern: | Shoot apex including leaf primordia and parts of leaves |
| Selection Criteria: | Ceres expression data. Greater than 5x up in stm microarray. |
| Gene: | Cys/Met metabolism pyridoxal-phosphate-dependent enzyme family protein |
| GenBank: | NM_105141 *Arabidopsis thaliana* Cys/Met metabolism pyridoxal-phosphate-dependent enzyme family protein (At1g64660) mRNA, complete cds |
| Source Promoter Organism: | *Arabidopsis thaliana*, Columbia ecotype |
| Vector: | pNewbin4-HAP1-GFP |
| Marker Type: | GFP-ER |
| Generation Screened: | X T1 Mature XT2 Seedling ☐T2 Mature ☐T3 Seedling |

| T1 Mature Plant Expression | Organs/Tissues screened |
|---|---|
| Events Screened: n = 2 | Events Expressing: n = 2 |

| GFP Expression Detected | |
|---|---|
| X Flower | ☐pedicel ☐receptacle ☐nectary H sepal H petal H filament ☐anther ☐pollen ☐carpel ☐style ☐papillae ☐vascular H epidermis L stomata ☐trichome ☐silique |
| X Silique | ☐stigma ☐style ☐carpel ☐septum ☐placentae ☐transmitting tissue ☐vascular ☐epidermis L stomata ☐abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐ embryo sack ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| X Stem | ☐epidermis ☐cortex ☐vascular ☐xylem ☐phloem ☐pith L stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

| T2 Seedling Expression | Tissues Screened |
|---|---|
| Events Screened: n = 2 | Events Expressing: n = 2 |

| Seedlings expressing/Seedlings screened |
|---|
| Event-01: 1/6 |
| Event-02: 6/6 |

| ☐ Scheduled<br>GFP Expression Detected | |
|---|---|
| X Hypocotyl | ☐epidermis ☐cortex ☐vascular ☐xylem ☐phloem L stomata |
| X Cotyledon | ☐mesophyll ☐vascular ☐epidermis ☐margin L stomata ☐hydathode |
| X Rosette Leaf | ☐mesophyll ☐vascular ☐epidermis ☐trichome ☐petiole ☐primordia L stomata ☐stipule ☐margin ☐hydathode |

-continued

| Promoter Expression Report #156 | |
|---|---|
| X Primary Root | H epidermis ☐trichoblast ☐atrichoblast ☐cortex ☐endodermis H vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

| Promoter utility | |
|---|---|
| Trait Area: | Nutrients, Stress |
| Sub-trait Area: | Nitrogen uptake, drought |
| Utility: | This promoter sequence can be used to improve: Modulation of flower development and structure. Modulation of drought responses. Modulation of nutrient and water uptake. |
| Notes: | Up-regulated in drought, ABA and far red light treatments. |
| Construct: | PT0564 |
| Promoter candidate I.D: | 11768766 |
| cDNA I.D: | 12348328 |
| Lines expressing: | PT0564-01, -02; 1/12/04. |

Example 24

| Promoter Expression Report #158 | |
|---|---|
| Promoter Tested In: | *Arabidopsis thaliana*, Wassilewskija WS ecotype |
| Spatial expression summary: | |
| Silique | H ovule H gametophyte |
| Hypocotyl | L vascular |
| Primary Root | H vascular H pericycle |
| Observed expression pattern: | |
| T1 mature: | Expression specific to cell types within the developing female gametophyte of the pre-fertilized ovule. GFP levels decrease post-fertilization with degenerating GFP appearing in suspensor cells of embryo and micropylar region in ovules. |
| T2 seedling: | High expression in vascular bundle of root with decreasing expression within hypocotyl. |
| Expected expression pattern: | Expressed primarily in the vascular cylinder of root. |
| Selection Criteria: | Public reference |
| Gene: | Leucine-rich repeat protein kinase |
| GenBank: | NM_126243 *Arabidopsis thaliana* leucine-rich repeat protein kinase, putative (At2g01820) mRNA, complete cds gi\|42568868\|ref\|NM_126243.2\|[42568868] |
| Source Promoter Organism: | *Arabidopsis thaliana*, Columbia ecotype |
| Vector: | pNewbin4-HAP1-GFP |
| Marker Type: | GFP-ER |
| Generation Screened: | X T1 Mature X T2 Seedling ☐T2 Mature ☐T3 Seedling |

| T1 Mature Plant Expression Events Screened: n = 2 | Organs/Tissues screened Events Expressing: n = 2 |
|---|---|

| GFP Expression Detected | |
|---|---|
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| X Silique | ☐stigma ☐style ☐carpel ☐septum ☐placentae ☐transmitting tissue ☐vascular ☐epidermis ☐stomata ☐abscission zone H ovule |
| H Ovule | Pre-fertilization: ☐primordia ☐inner integument ☐outer integument ☐embryo sac ☐funiculus ☐chalaza ☐micropyle H gametophyte Post-fertilization: ☐zygote ☐suspensor ☐embryo sac ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |

-continued

| Promoter Expression Report #158 | |
|---|---|
| ☐ Leaf | ☐petiole ☐mesophyll ☐vascular ☐epidermis ☐trichome ☐primordia ☐stomata ☐stipule ☐margin |
| ☐ Shoot apical meristem | ☐ Shoot apical meristem ☐ Flower primordium |

| T2 Seedling Expression Events Screened: n = 2 | Tissues Screened Events Expressing: n = 2 |
|---|---|

| Seedlings expressing/Seedlings screened |
|---|
| Event-01: 3/6<br>Event-02: 5/6 |

| ☐ Scheduled<br>GFP Expression Detected | |
|---|---|
| X Hypocotyl | ☐epidermis ☐cortex L vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | ☐epidermis ☐trichoblast ☐atrichoblast ☐cortex ☐endodermis H vascular ☐xylem ☐phloem H pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐Shoot apical meristem |

| Promoter utility | |
|---|---|
| Trait Area: | Seeds, PG&D, Nutrients, Stress |
| Sub-trait Area: | Seed number and size, nitrogen uptake |
| Utility: | This promoter sequence can be used to improve: Modulation of fertility control. Modulation of nitrogen and water transport. Modulation of seed fill and seed size. |
| Construct: | PT0569 |
| Promoter candidate I.D: | 11768780 |
| cDNA I.D: | 13578506 (OCKHAM3-CD) |
| Lines expressing: | -01, -03; Jan. 12, 2004. |

Example 25

| Promoter Expression Report #168 | |
|---|---|
| Promoter Tested In: | *Arabidopsis thaliana*, Wassilewskija (WS) ecotype |
| | Spatial expression summary: |
| Ovule | Post-fertilization: H outer integument, H mature endosperm |
| Embryo | H mature |
| Primary Root | H cortex H endodermis |
| | Observed expression pattern: |
| T1 mature: | GFP expression in cellularizing endosperm of pre-torpedo stage ovule and mature embryo and outer integument of developing seed. |
| T2 seedling: | GFP expression in cortex and endodermis cells of roots. Not observed in vascular bundle as described by Haseloff characterization of line H002536. |
| Expected expression pattern: | Vascular exp in root after elongation zone |
| Selection Criteria: | Haseloff two component line HAP1_ID: H002536 |
| Gene: | "transketolase family protein" |
| GenBank: | NM_129013 *Arabidopsis thaliana* transketolase family protein (At2g34590) mRNA, complete cdsgi\|30686124\|ref\|NM_129013.2 |
| Source Promoter Organism: | *Arabidopsis thaliana*, Columbia ecotype |
| Vector: | pNewbin4-HAP1-GFP |
| Marker Type: | GFP-ER |
| Generation Screened: | XT1 Mature XT2 Seedling ☐T2 Mature ☐T3 Seedling |

-continued

| Promoter Expression Report #168 | |
|---|---|
| T1 Mature Plant Expression Events Screened: n = 6 | Organs/Tissues screened Events Expressing: n = 3 |
| GFP Expression Detected | |
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐siligue |
| ☐ Silique | ☐stigma ☐style ☐carpel ☐septum ☐placentae ☐transmitting ☐tissue ☐vascular ☐epidermis ☐stomata ☐abscission zone ☐ovule |
| X Ovule | ☐Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐ embryo sac ☐inner integument H outer integument ☐endothelium ☐seed coat ☐primordia ☐chalaza ☐micropyle ☐early endosperm H mature endosperm ☐embryo |
| X Embryo | ☐suspensor ☐preglobular ☐globular ☐heart ☐torpedo ☐late H mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐ Shoot apical meristem ☐ Flower primordium |
| T2 Seedling Expression Events Screened: n = 2 | Tissues Screened Events Expressing: n = 2 |
| Seedlings expressing/Seedlings screened | |
| Event-03: 1/2<br>Event-04: 2/3 | |
| GFP Expression Detected | |
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | ☐epidermis ☐trichoblast ☐atrichoblast H cortex H endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐Shoot apical meristem |
| Promoter utility | |
| Trait Area: | PG&D, nutrients, Seeds |
| Sub-trait Area: | Root architecture, drought, seed size |
| Utility: | This promoter sequence can be used to improve: Alteration in seed composition. Enhanced desiccation tolerance and seed germination. Modulation endosperm development and composition. Enhanced seedling vigor. Modulation of drought tolerance and protection against drought stress. Modulation of seed size. |
| Notes: | Endosperm and embryo expression is not a common expression pattern. This promoter can be unusual and valuable for manipulation of an entire seed. Endogenous promoter induced by nitrate, heat, and UV-B treatments. Also induced in germinating seeds and root tips. |
| Construct: | PT0650 |
| Promoter candidate I.D: | 15224209 |
| cDNA I.D: | 13602857 |
| Lines expressing: | PT0650-03, -04, -06 |

Example 26

| Promoter Expression Report # 172 | |
|---|---|
| Promoter Tested In: | *Arabidopsis thaliana*, WS ecotype |
| Spatial expression summary: | |
| Embryo | H radicle |
| Primary Root | H root cap |
| Lateral root | H lateral root cap |
| Observed expression pattern: | |
| T1 mature: | High GFP expression and specificity to root cap of primary and lateral roots. Expression in root cap observed from mid-globular to mature embryo. Low expression in mature endosperm. |
| T2 seedling: | High GFP expression and specificity to root cap of main and lateral roots. |
| Expected expression pattern: | Haseloff characterization of line H000737. Expression in epidermis and cortex of primary and secondary roots. Not in root tip. Expression maintained throughout elongation but lost soon after elongation is complete |
| Selection Criteria: | Two component line HAP1_ID: H000737 |
| Gene: | “Scarecrow transcription factor family protein” |
| GenBank: | NM_100626 *Arabidopsis thaliana* scarecrow transcription factor family protein (At1g07520) mRNA, complete cds gi\|42561783\|ref\|NM_100626.2\|[42561783] |
| Source Promoter Organism: | *Arabidopsis thaliana*, Columbia |
| Vector: | pNewbin4-HAP1-GFP |
| Marker Type: | GFP-ER |
| Generation Screened: | XT1 Mature XT2 Seedling ☐T2 Mature ☐T3 Seedling |
| T1 Mature Plant Expression Organs/Tissues screened | |
| Events Screened: n = 5 Events Expressing: n = 3 | |
| GFP Expression Detected | |
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐ embryo sac ☐inner integument ☐outer integument ☐endothelium ☐seed coat ☐primordia ☐chalaza ☐micropyle ☐early endosperm ☐mature endosperm ☐embryo |
| X Embryo | ☐suspensor ☐preglobular ☐globular ☐heart ☐torpedo ☐late ☐mature ☐provascular ☐hypophysis H radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐ Shoot apical meristem ☐ Flower primordium |
| T2 Seedling Expression Tissues Screened | |
| Events Screened: n = 2 Events Expressing: n = 2 | |
| Seedlings expressing/Seedlings screened | |
| Event-01: 3/4 | |
| Event-02: 3/6 | |
| GFP Expression Detected | |
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | ☐epidermis ☐trichoblast ☐atrichoblast ☐cortex ☐endodermis ☐vascular ☐xylem ☐phloem ☐pericycle ☐quiescent ☐columella H root cap ☐root hairs |
| X Lateral root | ☐epidermis ☐trichoblast ☐atrichoblast ☐cortex ☐endodermis ☐initials ☐flanking cells ☐vascular H lateral root cap |
| ☐ Shoot apical meristem | ☐shoot apical meristem |

-continued

| Promoter Expression Report # 172 | |
|---|---|
| Promoter utility | |
| Trait Area: | Nutrients, PG&D, Stress |
| Sub-trait Area: | Nitrogen uptake, drought, root growth |
| Utility: | This promoter sequence can be used to improve: Modulation of root growth. Modulation of nutrient uptake. Modulation of drought stress. Modulation of biotic stress tolerance |
| Notes: | Sabatini S. Heidstra R, Wildwater M, Scheres B. SCARECROW is involved in positioning the stem cell niche in the *Arabidopsis* root meristem. Genes Dev. 2003 Feb 1; 17(3): 354-8. PMID: 12569126<br>Long JA, Woody S, Poethig S, Meyerowitz EM, Barton MK. Transformation of shoots into roots in *Arabidopsis* embryos mutant at the TOPLESS locus. Development. 2002 Jun; 129(12): 2797-806. PMID: |
| Construct: | PT0659 |
| Promoter candidate I.D: | 15224254 |
| cDNA I.D: | 12661578 (OCKHAM3-CD) |
| Lines expressing: | PT0659-02, -05, -04; Apr. 26, 2004 |

Example 27

| Promoter Expression Report #179 | |
|---|---|
| Promoter Tested In: | *Arabidopsis thaliana*, Wassilewskija (WS) ecotype |
| Spatial expression summary: | |
| Silique | H funiculus |
| Hypocotyl | M vascular |
| Cotyledon | L vascular |
| Primary Root | H vascular |
| Observed expression pattern: | |
| T1 mature: | GFP expression specific to funiculus of developing seed, decreasing in maturing seed. No expression observed in funiculus of prefertilized ovules. |
| T2 seedling: | GFP expression observed in vascular tissues of root, hypocotyls, petioles and cotyledons. |
| Expected expression pattern: | H004797: Seems to be expressed in the quiescent center and in all the initials around. Faint expression in vasculature later in the root. |
| Selection Criteria: | Two component line HAP1_ID: H004797 |
| Gene: | "adenylylsulfate kinase 1 (AKN1)" |
| GenBank: | NM_127039 *Arabidopsis thaliana* adenylylsulfate kinase 1 (AKN1) (At2g14750) mRNA, complete cds gi\|30679236\|ref\|NM_127039.2 |
| Source Promoter Organism: | *Arabidopsis thaliana*, Col |
| Vector: | pNewbin4-HAP1-GFP |
| Marker Type: | GFP-ER |
| Generation Screened: | XT1 Mature X T2 Seedling ☐T2 Mature ☐T3 Seedling |
| T1 Mature Plant Expression Events Screened: n = 3 | Organs/Tissues screened Events Expressing: n = 2 |
| GFP Expression Detected | |
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| X Silique | ☐stigma ☐style ☐carpel ☐septum ☐placentae H funiculus ☐transmitting tissue ☐vascular ☐epidermis ☐stomata ☐abscission zone ☐ovule |
| ☐ Ovule | Pre-fertilization: ☐primordia ☐inner integument ☐outer integument ☐embryo sac ☐funiculus ☐chalaza ☐micropyle ☐gametophyte<br>Post-fertilization: ☐zygote ☐suspensor ☐ embryo sac ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |

-continued

| Promoter Expression Report #179 | |
|---|---|
| ☐ Shoot apical meristem | ☐ Shoot apical meristem ☐ Flower primordium |
| T2 Seedling Expression Events Screened: n = 2 | Tissues Screened Events Expressing: n = 2 |
| Seedlings expressing/Seedlings screened | |
| Event-01: 3/6<br>Event-02: 3/6 | |
| GFP Expression Detected | |
| X Hypocotyl | ☐epidermis ☐cortex M vascular ☐xylem ☐phloem ☐stomata |
| X Cotyledon | ☐mesophyll L vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | ☐epidermis ☐trichoblast ☐atrichoblast ☐cortex ☐endodermis H vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐Shoot apical meristem |
| Promoter utility | |
| Trait Area: | PG&D, Nutrients |
| Sub-trait Area: | Seed fill, nutrient uptake |
| Utility: | This promoter sequence can be used to improve: Modulation of nitrogen uptake and transport. Modulation of seed size. |
| Notes: | Endogenous promoter is up-regulated by nitrates and UV-B and down-regulated in siliques. |
| Construct: | PT0655 |
| Promoter candidate I.D: | 15224239 |
| cDNA I.D: | 13616568 |
| Lines expressing: | PT0655-02, -04; Apr. 26, 2004 |

Example 28

| Promoter Expression Report #180 | |
|---|---|
| Promoter Tested In: | *Arabidopsis thaliana*, Wassilewskija WS ecotype |
| Spatial expression summary: | |
| Ovule | H embryo sac H gametophyte H early endosperm |
| Primary Root | L epidermis M cortex H endodermis L root cap |
| Observed expression pattern: | |
| T1 mature: | Low expressivity or penetrance of GFP within endosperm of developing ovules. Expressed in gametophyte of prefertilized through early cellularization stage fertilized ovules. Observed in few ovules per silique. |
| T2 seedling: | GFP expression throughout ground tissues of seedling roots. Not observed in vascular tissues. |
| Expected expression pattern: | Expression in several layers of the root. In colette, primary and secondary root. A few cells of root tip. Very strong expression. Also some patches in leaves and occasionally in the axils of the stem. |
| Selection Criteria: | Two component line HAP1_ID: H003816 |
| Gene: | The DER1 locus encodes ACTIN2 (ACT2), a major actin of the vegetative tissue. *Arabidopsis* mutant, deformed root hairs 1 (der1), that is impaired in root hair development. |
| GenBank: | NM_119078 *Arabidopsis thaliana* Der1-like family protein/degradation in the ER-like family protein (At4g29330) mRNA, complete cdsgi\|30688288\|ref\|NM_119078.3 |
| Source Promoter Organism: | *Arabidopsis thaliana*, Columbia |
| Vector: | pNewbin4-HAP1-GFP |
| Marker Type: | GFP-ER |
| Generation Screened: | X T1 Mature XT2 Seedling ☐T2 Mature ☐T3 Seedling |

-continued

| Promoter Expression Report #180 | |
|---|---|
| T1 Mature Plant Expression Events Screened: n = 6 | Organs/Tissues screened Events Expressing: n = 2 |
| GFP Expression Detected | |
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐ovule |
| X Ovule | Pre-fertilization: ☐primordia ☐inner integument ☐outer integument H embryo sac ☐funiculus ☐chalaza ☐micropyle H gametophyte Post-fertilization: ☐zygote ☐suspensor ☐ embryo sac ☐inner ☐integument ☐outer integument ☐endothelium ☐seed coat ☐primordia ☐chalaza ☐micropyle H early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐ mesophyll ☐vascular ☐epidermis ☐trichome ☐primordia ☐stomata ☐stipule ☐margin |
| ☐ Shoot apical meristem | ☐shoot apical meristem ☐flower primordium |
| T2 Seedling Expression Events Screened: n = 3 | Tissues Screened Events Expressing: n = 3 |
| Seedlings expressing/Seedlings screened | |
| Event-01: 1/6<br>Event-02: 1/6<br>Event-03: 3/6 | |
| GFP Expression Detected | |
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | L epidermis ☐trichoblast ☐atrichoblast M cortex H endodermis ☐vascular ☐xylem ☐phloem ☐pericycle ☐quiescent ☐columella L root cap ☐roat hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐Shoot apical meristem |
| Promoter utility | |
| Trait Area: | Nutrients, Drought, Seeds |
| Sub-trait Area: | Nitrogen uptake, drought |
| Utility: | This promoter sequence can be used to improve: Modulation of fertility control. Modulation of drought tolerance. Modulation of nitrogen uptake and transport. |
| Notes: | Ringli C. Baumberger N, Diet A, Frey B, Keller B. ACTIN2 is essential for bulge site selection and tip growth during root hair development of *Arabidopsis*. Plant Physiol. 2002 Aug; 129(4): 1464-72. PMID: 12177460. Knop M, Finger A, Braun T, Hellmuth K, Wolf DH. Der1, a novel protein specifically required for endoplasmic reticulum degradation in yeast. EMBO J. 1996 Feb 15; 15(4): 753-63. |
| Construct: | PT0656 |
| Promoter candidate I.D: | 15224245 |
| cDNA I.D: | 13593536 (OCKHAM3-CD) |
| Lines expressing: | PT0656-01, -02, -03 |

Example 29

| Promoter Expression Report #181 | |
|---|---|
| Promoter Tested In: | *Arabidopsis thaliana*, Wassilewskija WS ecotype |
| | Spatial expression summary: |

-continued

| Promoter Expression Report #181 | |
|---|---|
| Flower | H anther H silique |
| Silique | H ovule |
| Ovule | Post-fertilization: H zygote H suspensor H outer integument H seed coat<br>H embryo |
| Embryo | H suspensor H heart H torpedo M late L mature |
| Stem | L vascular |
| Shoot apical | L Shoot apical meristem L Flower primordium<br>Meristem |
| Hypocotyl | M epidermis M vascular |
| Cotyledon | M vascular M epidermis |
| Rosette Leaf | H mesophyll M vascular H epidermis H petiole |
| Primary Root | H vascular H root cap |
| Lateral root | H initials |

Observed expression pattern:

| | |
|---|---|
| T1 mature: | Low GFP expression in shoot apical meristem and floral primordia. In flowers, expression observed in the carpels of the developing silique, tapetum tissue of developing anthers, nectarines, and ovules. GFP is expressed in the outer integuments and globular to mature embryos from ovules to mature seed. Expression in embryos is preferentially located in the suspensor cells and embryonic root meristmatic cells. GFP expression in vasculature of stem. |
| T2 seedling: | GFP expression throughout vasculature, mesophyll and epidermis. In root, expression restricted to vascular bundle, lateral root primordia and root cap. |
| Expected expression pattern: | Strong and nice expression in root tip and in the elongation zone. Expression fades out quickly. Also expression in the initials of lateral root (low expression). |
| Selection Criteria: | Two component line HAP1_ID: H004467 |
| Gene: | product = "nascent polypeptide-associated complex (NAC)domain-containing protein/ BTF3b-like transcription factor, putative" |
| GenBank: | NM_101651 *Arabidopsis thaliana* nascent polypeptide-associated complex (NAC) domain-containing protein/BTF3b-like transcription factor, putative (At1g17880) mRNA |
| Source Promoter Organism: | *Arabidopsis thaliana*, Columbia |
| Vector: | pNewbin4-HAP1-GFP |
| Marker Type: | GFP-ER |
| Generation Screened: | XT1 Mature XT2 Seedling □T2 Mature □T3 Seedling |

| T1 Mature Plant Expression | Organs/Tissues screened |
|---|---|
| Events Screened: n = 4 | Events Expressing: n = 4 |

| GFP Expression Detected | |
|---|---|
| X Flower | □pedicel □receptacle □nectary □sepal □petal □filament H anther □pollen H carpel □style □papillae □vascular □epidermis □stomata □trichome<br>H silique |
| X Silique | □stigma □style □carpel □septum □placentae □transmitting tissue □vascular □epidermis □stomata □abscission zone H ovule |
| X Ovule | Pre-fertilization: □primordia □inner integument □outer integument □embryo sac □funiculus □chalaza □micropyle □gametophyte<br>Post-fertilization: H zygote H suspensor □ embryo sack □inner integument H outer integument □endothelium H seed coat □primordia □chalaza □micropyle □early endosperm □mature endosperm H embryo |
| X Embryo | H suspensor □preglobular □globular H heart H torpedo M late L mature □provascular □hypophysis □radicle □cotyledons □hypocotyl |
| X Stem | □epidermis □cortex L vascular □xylem □phloem □pith □stomata □trichome |
| □ Leaf | □petiole □mesophyll □vascular □epidermis □trichome □primordia □stomata □stipule □margin |
| X Shoot apical | L Shoot apical meristem L Flower primordium<br>meristem |

| T2 Seedling Expression | Tissues Screened |
|---|---|
| Events Screened: n = 3 | Events Expressing: n = 3 |

| Seedlings expressing/Seedlings screened |
|---|
| Event-01: 4/4 |
| Event-02: 3/6 |
| Event-03: 2/3 |

| GFP Expression Detected | |
|---|---|
| X Hypocotyl | M epidermis □cortex M vascular □xylem □phloem □stomata |
| X Cotyledon | □mesophyll M vascular M epidermis □margin □stomata □hydathode |

-continued

| Promoter Expression Report #181 | |
|---|---|
| X Rosette Leaf | H mesophyll M vascular H epidermis □trichome H petiole □primordia □stomata □stipule □margin □hydathode |
| X Primary Root | □epidermis □trichoblast □atrichoblast □cortex □endodermis H vascular □xylem □phloem H pericycle □quiescent □columella H root cap □root hairs |
| X Lateral root | □epidermis □trichoblast □atrichoblast □cortex □endodermis H initials □flanking cells □vascular □lateral root cap |
| □ Shoot apical meristem | □Shoot apical meristem |

| Promoter utility | |
|---|---|
| Trait Area: | PG&D, Nutrients, Stress, Seeds |
| Sub-trait Area: | Drought, nitrogen uptake, Seed size, seed fill |
| Utility: | This promoter sequence can be used to improve: Modulation of drought responses. Modulation of nitrogen and water uptake. Modulation of seed size and seed fill. Modulation of leaf angle. |
| Notes: | Nascent Polypeptide-associated Complex Stimulates Protein Import into Yeast Mitochondria. Funfschilling U, Rospert S. Mol Biol Cell. 1999 Oct 1; 10(10): 3289-3299. Down-regulated in germinating seeds and up-regulated in root tips. |
| Construct: | PT0657 |
| Promoter candidate I.D: | 15224248 |
| cDNA I.D: | 13604449 (OCKHAM3-CD) |
| Lines expressing: | PT0657-01, -02, -03, -04; Apr. 26, 2004 |

Example 30

| Promoter Expression Report # 186 | |
|---|---|
| Promoter Tested In: | *Arabidopsis thaliana*, Wassilewskija WS ecotype |
| Spatial expression summary: | |
| Primary Root | L cortex L vascular L pericycle |
| Observed expression pattern: | |
| T1 mature: | No expression observed. |
| T2 seedling: | Low expression in cortex and pericycle cells throughout root. |
| Expected expression pattern: | Expression in vascular or pericycle. |
| Selection Criteria: | Two-component line HAP1_ID: H006530 |
| Gene: | transcriptional factor B3 family protein |
| GenBank: | NM_112785 *Arabidopsis thaliana* transcriptional factor B3 family protein (At3g18990) mRNA, complete cds gi\|42564995\|ref\|NM_112785.3\|[42564995] |
| Source Promoter Organism: | *Arabidopsis thaliana*, Columbia |
| Vector: | pNewbin4-HAP1-GFP |
| Marker Type: | GFP-ER |
| Generation Screened: | XT1 Mature XT2 Seedling □T2 Mature □T3 Seedling |

| T2 Seedling Expression<br>Events Screened: n = 3 | Tissues Screened<br>Events Expressing: n = 2 |
|---|---|

| Seedlings expressing/Seedlings screened |
|---|
| Event-01: 1/3<br>Event-02: 2/6<br>Event-03: 0/6 |

| GFP Expression Detected | |
|---|---|
| □ Hypocotyl | □epidermis □cortex □vascular □xylem □phloem □stomata |
| □ Cotyledon | □mesophyll □vascular □epidermis □margin □stomata □hydathode |
| □ Rosette Leaf | □mesophyll □vascular □epidermis □trichome □petiole □primordia □stomata □stipule □margin □hydathode |
| X Primary Root | □epidermis □trichoblast □atrichoblast L cortex □endodermis L vascular □xylem □phloem L pericycle □quiescent □columella □root cap □root hairs |
| □ Lateral root | □epidermis □trichoblast □atrichoblast □cortex □endodermis □initials □flanking cells □vascular □lateral root cap |
| □ Shoot apical meristem | □Shoot apical meristem |

-continued

| Promoter Expression Report # 186 | |
|---|---|
| Promoter utility | |
| Trait Area: | Stress, Nutrients |
| Sub-trait Area: | Drought, Nitrogen uptake |
| Utility: | This promoter sequence can be used to improve: Modulation of drought tolerance. Modulation of nutrient uptake and transport. |
| Construct: | PT0660 |
| Promoter candidate I.D: | 15224257 |
| cDNA I.D: | 13614201 |
| Lines expressing: | PT0660-01, -02; Apr. 12, 2004 |

Example 31

| Promoter Expression Report #203 | |
|---|---|
| Promoter Tested In: | *Arabidopsis thaliana*, Wassilewskija (WS) ecotype |
| Spatial expression summary: | |
| Hypocotyl | L stomata |
| Cotyledon | L stomata |
| Rosette Leaf | L stomata |
| Primary Root | L epidermis H endodermis |
| Observed expression pattern: | |
| T1 mature: | No expression observed. |
| T2 seedling: | Primary GFP expression in root endodermal cell layer with weak expression in epidermal cells near transition zone. Guard cell expression throughout aerial tissue. |
| Expected expression pattern: | Shade Induced |
| Selection Criteria: | Ceres expression data |
| Gene: | Expressed protein |
| GenBank: | NM_125622 *Arabidopsis thaliana* expressed protein (At5g62280) mRNA, complete cds gi\|30697652\|ref\|NM_125622.2\|[30697652] |
| Source Promoter Organism: | *Arabidopsis thaliana*, Columbia |
| Vector: | pNewbin4-HAP1-GFP |
| Marker Type: | GFP-ER |
| Generation Screened: | XT1 Mature XT2 Seedling □T2 Mature □T3 Seedling |

Inductions completed:

| Treatment: | Age: | Gen: | Time points: | Events Screened/Response | Response: |
|---|---|---|---|---|---|
| 1. Far red Far $Red_{730}$ = 525 μW/cm$^2$ | 7 days | T2 | 1 Hr | 2/0 | No |
| | | | 24 Hr | 2/0 | No |

Inducible expression summary:

| Treatment: | Time point induced: | Organs induced: | Tissues induced: |
|---|---|---|---|
| 1. Far red Far $Red_{730}$ = 525 μW/cm$^2$ | 1 Hr | No differences observed. | |
| | 24 Hr | No differences observed. | |

Observation note: No differences were observed between control and experimental seedlings under far red conditions. Difference in expression levels compared to original T2 seedling screen. Higher expression can be seen in root epidermal cells and no GFP in guard cells can be detected.

| T1 Mature Plant Expression | Organs/Tissues screened |
|---|---|
| Events Screened: n = 3 | Events Expressing: n = 0 |

No GFP Expression Detected

| T2 Seedling Expression | Tissues Screened |
|---|---|
| Events Screened: n = 2 | Events Expressing: n = 2 |

Seedlings expressing/Seedlings screened

Event-01: 2/6
Event-04: 2/6

GFP Expression Detected

| | |
|---|---|
| X Hypocotyl | □epidermis □cortex □vascular □xylem □phloem L stomata |
| X Cotyledon | □mesophyll □vascular □epidermis □margin L stomata □hydathode |

-continued

| Promoter Expression Report #203 | |
|---|---|
| X Rosette Leaf | □mesophyll □vascular □epidermis □trichome □petiole □primordia L stomata □stipule □margin □hydathode |
| X Primary Root | L epidermis □trichoblast □atrichoblast □cortex H endodermis □vascular □xylem □phloem □pericycle □quiescent □columella □root cap □root hairs |
| □ Lateral root | □epidermis □trichoblast □atrichoblast □cortex □endodermis □initials □flanking cells □vascular □lateral root cap |
| □ Shoot apical meristem | □shoot apical meristem |
| **Promoter utility** | |
| Trait Area: | Stress, nutrients |
| Sub-trait Area: | Drought, nitrogen uptake |
| Utility: | This promoter sequence can be used to improve: Modulation of all responses to drought and heat stress. Protection against drought stress. Protection against heat stress. |
| Notes: | Endogenous promoter is down-regulated in heat and drought, up-regulated in far red light and circadian rhythm. |
| Construct: | PT0679 |
| Promoter candidate I.D: | 15295967 |
| cDNA I.D: | 12732583 (OCKHAM3-CD) |
| Lines expressing: | PT0679-01 |

Example 32

| Promoter Expression Report #205 | |
|---|---|
| Promoter Tested In: | *Arabidopsis thaliana*, Wassilewskija (WS) ecotype |
| **Spatial expression summary:** | |
| Silique | L funiculus H ovule |
| Ovule | Post-fertilization: L funiculus H outer integument |
| Hypocotyl | L epidermis |
| Cotyledon | H epidermis H petiole |
| Rosette Leaf | H epidermis H petiole |
| Primary Root | H endodermis |
| **Observed expression pattern:** | |
| T1 mature: | GFP expression highly specific to second cell layer of the outer integument in developing seed. Also expressed at ovule connective site of funiculus. No expression observed in pre-fertilized ovules. |
| T2 seedling: | GFP exhibits expression in a highly polar fashion in cotyledons and rosette leaves. GFP is expressed proximal-distal on the abaxial surface of the petioles of cotyledons and rosette leaves with respect to the shoot apical meristem. Low GFP expression observed on the adaxial surface of petioles of cotyledons and rosette leaves. GFP expression in epidermal cells of hypocotyl at the root transition zone decreases toward apex. Highly specific expression of GFP in endodermis cells of the root. |
| Expected expression pattern: | Shade Induced |
| Selection Criteria: | Ceres expression data |
| Gene: | Acyl CoA reductase, putative |
| GenBank: | NM_122155 *Arabidopsis thaliana* acyl CoA reductase, putative/male-sterility protein, putative (At5g22500) mRNA, complete cds gi\|30688503\|ref\|NM_122155.2\|[30688503] |
| Source Promoter Organism: | *Arabidopsis thaliana*, Columbia ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed.

| Treatment: | Age: | Gen: | Time points: | Events Screened/Response | Response: |
|---|---|---|---|---|---|
| 1. Far red Far Red$_{730}$ = 525 μW/cm$^2$ | 7 days | T2 | 1 Hr | 2/0 | No |
| | | | 24 Hr | 2/0 | No |

Inducible expression summary:

| Treatment: | Time point induced: | Organs induced: | Tissues induced: |
|---|---|---|---|
| 1. Far red | No differences observed. | | |

| T1 Mature Plant Expression | Organs/Tissues screened |
|---|---|
| Events Screened: n = 3 | Events Expressing: n = 3 |

-continued

| Promoter Expression Report #205 | |
|---|---|
| GFP Expression Detected | |
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| X Silique | ☐stigma ☐style ☐carpel ☐septum ☐placentae L funiculus ☐transmitting tissue ☐vascular ☐epidermis ☐stomata ☐abscission zone H ovule |
| X Ovule | Pre-fertilization: ☐primordia ☐inner integument ☐outer integument ☐funiculus ☐embryo sac ☐chalaza ☐micropyle ☐gametophyte Post-fertilization: ☐zygote ☐suspensor ☐ embryo sack L funiculus ☐inner integument H outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

| T2 Seedling Expression<br>Events Screened: n = 2 | Tissues Screened<br>Events Expressing: n = 2 |
|---|---|
| Seedlings expressing/Seedlings screened | |
| Event-01: 2(6)<br>Event-02: 2(6) | |
| GFP Expression Detected | |
| X Hypocotyl | L epidermis ☐cortex ☐vascular ☐xylem ☐phloem ☐stomata |
| X Cotyledon | ☐ mesophyll ☐vascular H epidermis ☐margin H petiole ☐stomata ☐hydathode |
| X Rosette Leaf | ☐ mesophyll ☐vascular H epidermis ☐trichome H petiole ☐primordia ☐stomata ☐stipule ☐margin ☐hydathode |
| X Primary Root | ☐epidermis ☐trichoblast ☐atrichoblast ☐cortex H endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

| Induction Screens | |
|---|---|
| 1. Far red | No differences observed. |

| Promoter utility | |
|---|---|
| Trait Area: | PG&D, nutrients |
| Sub-trait Area: | Nitrogen use efficiency, seed size |
| Utility: | This promoter sequence can be used to modulate seed growth and development, seed dormancy and germination. Also, useful for enhancement of leaf and root growth, resulting in increased source capacity and water and nutrient loading. Useful in procedures and technologies aimed at improving source-sink relationships and seed filling and yield. |
| Notes: | Lardizabal KD, Metz JG, Sakamoto T, Hutton WC, Pollard MR, Lassner MW. Purification of a jojoba embryo wax synthase, cloning of its cDNA, and production of high levels of wax in seeds of transgenic *arabidopsis*. Plant Physiol. 2000 Mar; 122(3): 645-55. Metz JG, Pollard MR, Anderson L, Hayes TR, Lassner MW. Purification of a jojoba embryo fatty acyl-coenzyme A reductase and expression of its cDNA in high erucic acid rapeseed. Plant Physiol. 2000 122: 635-44. |
| Construct: | PT0676 |
| Promoter candidate I.D: | 15295958 |
| cDNA I.D: | 23658955 |
| Lines expressing: | PT0676-01, -02; Apr. 12, 2004 |

Example 33

| Promoter Expression Report #177 | |
|---|---|
| Promoter Tested In: | *Arabidopsis thaliana*, Wassilewskija (WS) ecotype |
| Spatial expression summary: | |
| Flower | H pedicel H petal M filament M anther H epidermis H carpel |
| Silique | H carpel H epidermis |
| Stem | L endodermis H pith |
| Rosette Leaf | L epidermis H trichome H petiole |
| Observed expression pattern: | |
| T1 mature: | Vegetatative expression. GFP expressed in epidermis of stem and pedicels of the inflorescence meristem near the shoot apex. In the Flower, GFP expression is specific to stamen and carpels of siliques. GFP highly expressed in parenchyma cells of stem. No expression in ovules. |
| T2 seedling: | High specific GFP expression in cells at the base of developing trichomes and petioles of rosette leaves. Expression in adventitious trichome cells of the hypocotyls. |
| Expected expression pattern: | Shade Induced |
| Selection Criteria: | Ceres expression data |
| Gene: | expressed protein; “/product = “unknown protein” |
| GenBank: | NM_113862 expressed protein (At3g29370) mRNA, complete |
| Source Promoter Organism: | *Arabidopsis thaliana*, Columbia ecotype |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed.

| Treatment: | Age: | Gen: | Time points: | Events Screened/ Response | Response: |
|---|---|---|---|---|---|
| 1. Far red | 7 days | T2 | 1 Hr | 2/0 | No |
| Far $Red_{730}$ = 525 μW/$cm^2$ | | | 24 Hr | 2/1 | Yes |

Inducible expression summary:

| Treatment: | Time point induced: | Organs induced: | Tissues induced: |
|---|---|---|---|
| 1. Far red<br>Far $Red_{730}$ = 525 μW/$cm^2$ | 24 Hr | Petiole | Epidermis, Cortex, Vascular |

T1 Mature Plant Expression Organs/Tissues screened
Events Screened: n = 6 Events Expressing: n = 2

GFP Expression Detected

| | |
|---|---|
| X Flower | H pedicel ☐receptacle ☐nectary ☐sepal H petal M filament M anther ☐pollen H carpel ☐style ☐papillae ☐vascular H epidermis ☐stomata ☐trichome ☐silique |
| X Silique | ☐stigma ☐style H carpel ☐septum ☐placentae ☐transmitting tissue ☐vascular H epidermis ☐stomata ☐abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐ embryo sack ☐funiculus ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| X Stem | ☐ epidermis ☐cortex L endodermis ☐ vascular ☐xylem ☐phloem H pith ☐stomata ☐trichome |
| ☐ Leaf | ☐petiole ☐ mesophyll ☐vascular ☐epidermis ☐trichome ☐primordia ☐stomata ☐stipule ☐margin |
| ☐ Shoot apical meristem | ☐ Shoot apical meristem ☐ Flower primordium |

T2 Seedling Expression Tissues Screened
Events Screened: n = 2 Events Expressing: n = 2

Seedlings expressing/Seedlings screened

Event-01: 4(6)
Event-05: 3(6)

-continued

| Promoter Expression Report #177 | |
|---|---|
| GFP Expression Detected | |
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| X Rosette Leaf | ☐mesophyll ☐vascular L epidermis H trichome H petiole ☐primordia ☐stomata ☐stipule ☐margin ☐hydathode |
| ☐ Primary Root | ☐epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐Shoot apical meristem |
| Promoter utility | |
| Utility: | This promoter sequence can be used to improve: Modulation of flower and inflorescence structure, especially numbers of flowers per inflorescence and therefore seeds per inflorescence. Modulation of carpel symmetry and number of valves per carpel and number of seeds per carpel. Modulation of shade avoidance responses, especially petiole and leaf elongation under shade. Enhanced seedling and plant performance under shade conditions. Combinational effects or growth, development, fertility and responses to shade. |
| Construct: | PT0684 |
| Promoter candidate I.D: | 15295997 |
| cDNA I.D: | 13486695 |
| Lines expressing: | PT0684-01-05; Apr. 26, 2004 |

Example 34

| Promoter Expression Report #178 | |
|---|---|
| Promoter Tested In: | *Arabidopsis thaliana*, Wassilewskija (WS) ecotype |
| Spatial expression summary: | |
| Flower | H stomata |
| Ovule | Post-fertilization: M endothelium |
| Stem | H stomata |
| Leaf | H stomata |
| Cotyledon | H stomata |
| Rosette Leaf | H stomata |
| Primary Root | M epidermis H pericycle H root hairs |
| Lateral root | H initials H lateral root cap |
| Observed expression pattern: | |
| T1 mature: | High GFP expression in guard cells throughout mature plant aerial tissue and endothelium cell layer of developing seed. |
| T2 seedling: | GFP expression in trichomes and guard cells of cotyledons and rosette leaves. Primary expression in root localized to pericycle cells and lateral root initials and later in mature lateral root cap. Weak epidermal and root hair expression. |
| Expected expression pattern: | Shade Induced |
| Selection Criteria: | Ceres expression data |
| Gene: | short-chain dehydrogenase/reductase (SDR) family protein, oxidoreductase activity |
| GenBank: | NM_120332 *Arabidopsis thaliana* short-chain dehydrogenase/reductase (SDR) family protein (At5g02540) mRNA, complete cds gi\|30679675\|ref\|NM_120332.2\|[30679675] |
| Source Promoter Organism: | *Arabidopsis thaliana*, Columbia |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed:

| Treatment: | Age: | Gen: | Time points: | Events Screened/ Response | Response: |
|---|---|---|---|---|---|
| 1. Far red | 7 days | T2 | 1 Hr | 2/0 | No |
| Far $Red_{730}$ = 525 $\mu W/cm^2$ | | | 24 Hr | 2/2 | Yes |

-continued

| Promoter Expression Report #178 | | | |
|---|---|---|---|
| **Inducible expression summary:** | | | |
| Treatment: | Time point induced: | Organs induced: | Tissues induced: |
| 1. Far red | 1 Hr | No differences observed. | |
| Far $Red_{730}$ = 525 $\mu W/cm^2$ | 24 Hr | Cotyledon | Stomata |
| | | Rosette Leaf | Stomata |

| T1 Mature Plant Expression | Organs/Tissues screened |
|---|---|
| Events Screened: n = 4 | Events Expressing: n = 2 |

GFP Expression Detected

| | |
|---|---|
| X Flower | □pedicel □receptacle □nectary □sepal □petal □filament □anther □pollen □carpel □style □papillae □vascular □epidermis H stomata □trichome □silique |
| □ Silique | □stigma □style □carpel □septum □placentae □transmitting tissue □vascular □epidermis □stomata □abscission zone □ovule |
| X Ovule | Pre-fertilization: □primordia □inner integument □outer integument □embryo sac □funiculus □chalaza □micropyle □gametophyte Post-fertilization: □zygote □suspensor □ embryo sack □inner integument □outer integument M endothelium □seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| X Stem | □epidermis □cortex □vascular □xylem □phloem □pith H stomata □trichome |
| X Leaf | □petiole □mesophyll □vascular □epidermis □trichome □primordia H stomata □stipule □margin |
| □ Shoot apical meristem | □shoot apical meristem □flower primordium |

| T2 Seedling Expression | Tissues Screened |
|---|---|
| Events Screened: n = 2 | Events Expressing: n = 2 |

Seedlings expressing/Seedlings screened

Event-03: 6(6)
Event-04: 5(6)

GFP Expression Detected

| | |
|---|---|
| □ Hypocotyl | □epidermis □cortex □vascular □xylem □phloem □stomata |
| X Cotyledon | □mesophyll □vascular □epidermis □margin H stomata □hydathode |
| X Rosette Leaf | □mesophyll □vascular □epidermis □trichome □petiole □primordia H stomata □stipule □margin □hydathode |
| X Primary Root | M epidermis □trichoblast □atrichoblast □cortex □endodermis □vascular □xylem □phloem H pericycle □quiescent □columella □root cap H root hairs |
| X Lateral root | □epidermis □trichoblast □atrichoblast □cortex □endodermis H initials □flanking cells □vascular H lateral root cap |
| □ Shoot apical meristem | □shoot apical meristem |

Promoter utility

| | |
|---|---|
| Trait Area: | Stress, Nitrogen, PG&D |
| Sub-trait Area: | Drought, drought, nitrogen uptake, root architecture |
| Utility: | This promoter sequence can be used to improve: Tolerance to drought conditions. Tolerance to heat conditions. Modulation of responses to abiotic stress. Modulation of plant interactions with insects and protection against insects. Modulation of production and loading of volatiles into trichomes and other epidermal cells. Enhanced root rate and root size. Modulation of water and mineral ion uptake. Modulation of lateral root initiation and growth and root architecture. |
| Notes: | Endogenous promoter is up-regulated in shoots and siliques and under far red light. |
| Construct: | PT0678 |
| Promoter candidate I.D: | 15295964 |
| cDNA I.D: | 12712683 (OCKHAM3-CD) |
| Lines expressing: | PT0678-03, -04 |

Example 35

| Promoter Expression Report #161 | |
|---|---|
| Promoter Tested In: | *Arabidopsis thaliana*, Wassilewskija (WS) ecotype |
| | Spatial expression summary: |
| Flower | H pedicel H sepal H petal H filament H anther H carpel H style H epidermis H stomata H silique |
| Silique | H style H carpel H transmitting tissue H epidermis H ovule |
| Ovule | Pre-fertilization: L funiculus L outer integument<br>Post-fertilization: H funiculus H outer integument H seed coat |
| Stem | L vascular L phloem |
| Leaf | L vascular |
| Hypocotyl | H epidermis L vascular |
| Cotyledon | L epidermis |
| Rosette Leaf | L vascular L epidermis |
| Primary Root | H epidermis H cortex H endodermis H vascular H quiescent H root cap H root hairs |
| | Observed expression pattern: |
| T1 mature: | GFP expression in sepals, petals, stamens and siliques of developing floral buds through to mature flowers. GFP expression throughout all tissues of stamen excluding pollen. GFP expression throughout all tissues of silique excluding stigma. Within ovules, highest GFP expression is at funiculus, outer integument and mature seed coat. GFP expression in vascular tissues of flowers, stems and leaves. In stem, expression in phloem cells within vascular bundle. Expression in guard cells throughout plant. |
| T2 seedling: | High GFP expression throughout epidermal tissues of seedlings. High GFP expression throughout all root cell types decreasing toward elongation zone. GFP is expressed in root cap and meristem cells. |
| Expected expression pattern: | High in siliques |
| Selection Criteria: | Microarray data |
| Gene: | Chlorophyll A-B binding family protein/early light-induced protein |
| GenBank: | NM_113183 *Arabidopsis thaliana* chlorophyll A-B binding family protein/early light-induced protein (ELIP) (At3g22840) mRNA, complete cds gi\|30686801\| |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling □T2 Mature □T3 Seedling |

| Treatment: | Age: | Gen: | Time points: | Events Screened/Response: | Response: |
|---|---|---|---|---|---|
| 1. Drought | 4 wks | T2 | 8 days no water | 2/0 | No |
| 2. Heat | 7 days | T2 | 2 Hr 42 C. | 3/0 | No |
| | | | 6 Hr 42 C. | 3/0 | No |
| | | | 16 Hrs - Post 42 C. | 3/0 | No |

T1 Mature Plant Expression Organs/Tissues screened
Events Screened: n = 6 Events Expressing: n = 3

| GFP Expression | |
|---|---|
| X Flower | H pedicel □receptacle □nectary H sepal H petal H filament H anther □pollen H carpel H style □papillae □vascular H epidermis H stomata □trichome H silique |
| X Silique | □stigma H style H carpel □septum □ placentae H transmitting tissue □vascular H epidermis □stomata □abscission zone H ovule |
| X Ovule | Pre-fertilization: □primordia □inner integument L outer integument □embryo sac L funiculus □chalaza □micropyle □gametophyte<br>Post-fertilization: □zygote □suspensor □ embryo sac H funiculus □inner integument H outer integument □endothelium H seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| X Stem | □epidermis □cortex L vascular □xylem L phloem □pith □stomata □trichome |
| X Leaf | □petiole □mesophyll L vascular □epidermis □trichome □primordia □stomata □stipule □margin |
| □ Shoot apical meristem | □shoot apical meristem □flower primordium |

T2 Seedling Expression Tissues Screened
Events Screened: n = 3 Events Expressing: n = 3

-continued

| Promoter Expression Report #161 | |
|---|---|
| Seedlings expressing/Seedlings screened | |
| Event-01: 3/4<br>Event-05: 3/6<br>Event-06: 4/6 | |
| X Hypocotyl | H epidermis □cortex L vascular □xylem □phloem □stomata |
| X Cotyledon | □mesophyll □vascular L epidermis □margin □stomata □hydathode |
| X Rosette Leaf | □mesophyll L vascular L epidermis □trichome □petiole □primordia □stomata □stipule □margin □hydathode |
| X Primary Root | H epidermis □trichoblast □atrichoblast H cortex H endodermis H vascular □xylem □phloem □pericycle H quiescent □columella H root cap H root hairs |
| □ Lateral root | □epidermis □trichoblast □atrichoblast □cortex □endodermis □initials □flanking cells □vascular □lateral root cap |
| □ Shoot apical meristem | □shoot apical meristem |
| Promoter utility | |
| Trait Area: | Nutrients, seed yield, water use efficiency |
| Sub-trait Area: | Nitrogen use efficiency, ovule/seed abortion, endosperm cell number/size, endosperm granule number/size, seed enhancement, seed number, harvest index, heat, water potential, drought, moisture stress at seed set |
| Utility: | This promoter sequence can be used to improve: Nitrogen use efficiency, ovule/seed abortion, endosperm cell number/size, endosperm granule number/size, seed enhancement, seed number, harvest index, heat, water potential, drought, moisture stress at seed set |
| Notes: | This promoter is strongly differentially regulated under drought conditions and in a number of tissues. |
| Construct: | PT0623 |
| Promoter candidate I.D: | 11768718 |
| cDNA I.D: | 23644072 |
| Lines expressing: | PT0623-01, -05, -06 |

Example 36

| Promoter Expression Report #163 | |
|---|---|
| Promoter Tested In: | *Arabidopsis thaliana*, Wassilewskija (WS) ecotype |
| Spatial expression summary: | |
| Flower | H pollen |
| Silique | M ovule |
| Ovule | Post-fertilization: M inner integument M endothelium M embryo |
| Embryo | M mature embryo H root tip L radicle |
| Stem | L vascular |
| Primary Root | H epidermis H cortex L root cap H root hairs |
| Observed expression pattern: | |
| T1 mature: | High GFP expression in endothelium cell layer of ovules and root cap of embryos. GFP expressed in pollen. Low GFP expression in stem vascular tissue. |
| T2 seedling: | High GFP expression specific to epidermal cells and root cap. GFP expression in epidermal cells decreases toward root elongation zone where no expression is observed. |
| Expected expression pattern: | Flowers and buds |
| Selection Criteria: | Microarray data |
| Gene: | product = "expressed protein"/note = "similar to myo-inositol oxygenase |
| GenBank: | NM_127538 *Arabidopsis thaliana* expressed protein (At2g19800) mRNA, complete |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | XT1 Mature XT2 Seedling □T2 Mature □T3 Seedling |

| Treatment: | Age: | Gen: | Time points: | Events Screened/Response: | Response: |
|---|---|---|---|---|---|
| 1. Drought | 4 wks | T2 | 8 days no water | 5/0 | No |
| 2. ABA 100 uM | 7 days | T2 | 2 Hr | 4/0 | No |
| | | | 6 Hr | 4/0 | No |

-continued

| Promoter Expression Report #163 | |
|---|---|
| T1 Mature Plant Expression Events Screened: n = 4 | Organs/Tissues screened Events Expressing: n = 2 |
| X Flower | □pedicel □receptacle □nectary □sepal □petal □filament □anther H pollen □carpel □style □papillae □vascular □epidermis □stomata □trichome □silique |
| X Silique | □stigma □style □carpel □septum □placentae □transmitting tissue □vascular □epidermis □stomata □abscission zone M ovule |
| X Ovule | Pre-fertilization: □primordia □inner integument □outer integument □embryo sac □funiculus □chalaza □micropyle □gametophyte Post-fertilization: □zygote □suspensor □ embryo sac M inner integument □outer integument M endothelium □seed coat □primordia □chalaza □micropyle □early endosperm □mature endosperm M embryo |
| X Embryo | □suspensor □preglobular □globular □heart □torpedo □late M mature □provascular □hypophysis H root tip L radicle □cotyledons □hypocotyl |
| X Stem | □epidermis □cortex L vascular □xylem □phloem □pith □stomata □trichome |
| □ Leaf | □petiole □mesophyll □vascular □epidermis □trichome □primordia □stomata □stipule □margin |
| □ Shoot apical meristem | □shoot apical meristem □flower primordium |
| T2 Seedling Expression Events Screened: n = 2 | Tissues Screened Events Expressing: n = 2 |
| Seedlings expressing/Seedlings screened | |
| Event-01: 5/6 Event-02: 4/6 | |
| □ Hypocotyl | □epidermis □cortex □vascular □xylem □phloem □stomata |
| □ Cotyledon | □mesophyll □vascular □epidermis □margin □stomata □hydathode |
| □ Rosette Leaf | □mesophyll □vascular □epidermis □trichome □petiole □primordia □stomata □stipule □margin □hydathode |
| X Primary Root | H epidermis □trichoblast □atrichoblast H cortex □endodermis □vascular □xylem □phloem □pericycle □quiescent □columella L root cap H root hairs |
| □ Lateral root | □epidermis □trichoblast □atrichoblast □cortex □endodermis □initials □flanking cells □vascular □lateral root cap |
| □ Shoot apical meristem | □shoot apical meristem |
| Promoter utility | |
| Trait Area: | Seed, yield, nutrients |
| Sub-trait Area: | Seed enhancement, harvest index, nitrogen use efficiency |
| Utility: | This promoter sequence can be used to improve: Seed enahancement, nutrient uptake and thus yield. |
| Notes: | Lorence A, Chevone BI, Mendes P, Nessler CL. myo-inositol oxygenase offers a possible entry point into plant ascorbate biosynthesis. Plant Physiol. 2004 Mar; 134(3): 1200-5. Epub 2004 Feb 19. |
| Construct: | PT0613 |
| Promoter candidate I.D: | 13148297 |
| cDNA I.D: | 23555688 |
| Lines expressing: | PT0613-01, -04; Feb. 20, 2004 |

Example 37

| Promoter Expression Report #190 | |
|---|---|
| Promoter Tested In: | *Arabidopsis thaliana*, Wassilewskija (WS) ecotype |
| | Spatial expression summary: |
| Flower | H pedicel H carpel H style H epidermis H silique |
| Silique | H style H carpel H epidermis H cortex H abscission zone |
| Stem | H epidermis H cortex |
| Leaf | H epidermis |
| Hypocotyl | L epidermis L stomata |
| Cotyledon | L epidermis L stomata |

-continued

Promoter Expression Report #190

Observed expression pattern:

| | |
|---|---|
| T1 mature: | Vegetative GFP expression. GFP expressed in walls of carpels and not expressed in placenta, ovules or embryo. GFP expression in carpels of developing siliques beginning at floral stage 12 and decreases in mature siliques. GFP also highly expressed in pedicels and abscission zone. High GFP expression in epidermis of leaf. GFP highly expressed throughout epidermis and cortex cells of stem. |
| T2 seedling: | GFP is expressed in epidermis of hypocotyls and cotyledons. Not observed in rosette leaf or root. |
| Expected expression pattern: | Drought inducible - Up regulated under drought |
| Selection Criteria: | Microarray |
| Gene: | expressed protein |
| GenBank: | NM_124750 *Arabidopsis thaliana* expressed protein (At5g53710) mRNA, complete cds gi\|18423543\|ref\|NM_124750.1\|[18423543] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling □T2 Mature □T3 Seedling |

| Treatment: | Age: | Gen: | Time points: | Events Screened/Response: | Response: |
|---|---|---|---|---|---|
| 1. Drought | 7 days | T2 | 3 hours air dry | 2/1 | Yes |
| 2. Drought | 4 wks | T2 | 8 days no water | 2/1 | Yes |

Inducible expression summary:

| Treatment: | Time point induced: | Organs induced: | Tissues induced: |
|---|---|---|---|
| 1. Drought | 3 hours air dry | Hypocotyl | L Epidermis |
| 2. Drought | 8 days no water | Stem | H Epidermis |
| | | Siliques | H Epidermis |

T1 Mature Plant Expression Organs/Tissues screened
Events Screened: n = 4 Events Expressing: n = 4

| | |
|---|---|
| X Flower | H pedicel □receptacle □nectary □sepal □petal □filament □anther □pollen H carpel H style □papillae □vascular H epidermis □stomata □trichome H silique |
| X Silique | □stigma H style H carpel □septum □placentae □funiculus □transmitting tissue □vascular H epidermis H cortex □stomata H abscission zone □ovule |
| □ Ovule | Pre-fertilization: □primordia □inner integument □outer integument □embryo sac □funiculus □chalaza □micropyle □gametophyte Post-fertilization: □zygote □suspensor □ embryo sack □funiculus □inner integument □outer integument □endothelium □seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| X Stem | H epidermis H cortex □interfascicular region □vascular □xylem □phloem □pith □stomata □trichome |
| X Leaf | H epidermis □petiole □mesophyll □vascular □trichome □primordia □stomata □stipule □margin |
| □ Shoot apical meristem | □ Shoot apical meristem □ Flower primordium |

T2 Seedling Expression Tissues Screened
Events Screened: n = 2 Events Expressing: n = 2

Seedlings expressing/Seedlings screened

Event-01: 4/6
Event-02: 5/6

| | |
|---|---|
| X Hypocotyl | L epidermis □cortex □vascular □xylem □phloem L stomata |
| X Cotyledon | □mesophyll □vascular L epidermis □margin □petiole L stomata □hydathode |
| □ Rosette Leaf | □mesophyll □vascular □epidermis □trichome □petiole □primordia □stomata □stipule □margin □hydathode |
| □ Primary Root | □epidermis □trichoblast □atrichoblast □cortex □endodermis □vascular □xylem □phloem □pericycle □quiescent □columella □root cap □root hairs |
| □ Lateral root | □epidermis □trichoblast □atrichoblast □cortex □endodermis □initials □flanking cells □vascular □lateral root cap |
| □ Shoot apical meristem | □Shoot apical meristem |

-continued

| Promoter Expression Report #190 |
|---|
| Induction Screens |
| 1. Drought Seedling<br>Increase GFP expression relative to control is observed in the epidermal tissues of the hypocotyl after 3 Hr air dried seedlings are scanned.<br>2. Drought Mature<br>Events of line PT0848 under drought and controlled conditions. Increase in GFP expression relative to control line observed in stems and siliques of event 01. |

| Promoter utility | |
|---|---|
| Trait Area: | PG&D, Drought |
| Sub-trait Area: | Fruit size, desiccation tolerance, recovery from drought |
| Utility: | Among other uses this promoter sequence can be used to improve: Fruit size, desiccation tolerance, recovery from drought |
| Notes: | Smyth DR, Bowman JL, Meyerowitz EM. Early flower development in *Arabidopsis*. Plant Cell. 1990 Aug; 2(8): 755-67. |
| Construct: | PT0848 |
| Promoter candidate I.D: | 15371545 |
| cDNA I.D: | 23541050 |
| Lines expressing: | PT0848 01-04 |

Example 38

| Promoter Expression Report #192.PT0852 | |
|---|---|
| Promoter Tested In: | *Arabidopsis thaliana*, Wassilewskija (WS) ecotype |
| | Spatial expression summary: |
| Flower | H pedicel H nectary H sepal H petal H anther H epidermis |
| Silique | H abscission zone |
| Ovule | Post-fertilization: L inner integument L seed coat |
| Stem | L epidermis |
| Inflorescence Meristem | L shoot apical meristem |
| Hypocotyl | L epidermis |
| Cotyledon | L epidermis H petiole |
| Rosette Leaf | H epidermis H petiole |
| Primary Root | H epidermis |
| | Observed expression pattern: |
| T1 Mature expression: | High GFP expression levels in the inflorescence meristem. GFP is expressed throughout stem and pedicles near the inflorescence meristem and in sepals, petals and stamens of flowers. High GFP expression at the abscission zone of mature flowers and senescencing siliques. Low GFP expression detected at shoot apical meristem. Increased expression of GFP observed in inner integument cells at micropylar-chalazal poles of ovules and throughout endothelium of developing and mature seed. Low GFP expression throughout stem with increased GFP expression in the trichome producing epidermal base cells. |
| T2 Seedling expression: | High GFP expression in pedicles of cotyledons and rosette leaves and the entire apical region of seedlings. Increased GFP expression in the trichome producing epidermal base cells. High GFP expression in epidermal cells in the hypocotyl-root transition zone and root. |
| Expected expression pattern: | Shade-induced |
| Selection Criteria: | Microarray data |
| Gene: | Long hypocotyl in far-red 1 (HFR1)/reduced phytochrome signaling (REP1)/basic helix-loop-helix FBI1 protein (FBI1)/reduced sensitivity to far-red light (RSF1)/bHLH protein 26 (BHLH026) (BHLH26). |
| GenBank: | NM_100115 *Arabidopsis thaliana* long hypocotyls in far red1 (HFR1)/reduced phytochrome signaling (REP1)/basic helix-loop-helix FBI1 protein (FBI1) (At1g02340) mRNA. |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | XT1 Mature XT2 Seedling □T2 Mature □T3 Seedling |

Inductions completed.

| Treatment: | Age: | Gen: | Time points: | Events Screened/Response | Response: |
|---|---|---|---|---|---|
| 1. Far red | 7 d. | T2 | 1 Hr | 3/0 | No |
| Far Red$_{730}$ = 525 μW/cm$^2$ | | | 24 Hr | 3/0 | No |

-continued

| Promoter Expression Report #192.PT0852 | |
|---|---|
| T1 Mature Plant Expression<br>Events Screened: n = 5 | Organs/Tissues screened<br>Events Expressing: n = 3 |
| X Flower | H pedicel □receptacle H nectary H sepal H petal □filament H anther □pollen □carpel □style □papillae □vascular H epidermis □stomata □trichome □silique |
| X Silique | □stigma □style □carpel □septum □placentae □funiculus □transmitting tissue □vascular □epidermis □stomata H abscission zone □ovule |
| X Ovule | Pre-fertilization: □primordia □inner integument □outer integument □embryo sac □funiculus □chalaza □micropyle □gametophyte Post-fertilization: □zygote □suspensor □ embryo sack □funiculus L inner integument □ outer integument □ endothelium L seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □root meristem □shoot meristem |
| X Stem | L epidermis □cortex □interfascicular region □vascular □xylem □phloem □pith □stomata □trichome |
| □ Leaf | □petiole □mesophyll □vascular □epidermis □trichome □primordia □stomata □stipule □margin |
| X Inflorescence meristem | L shoot apical meristem □ flower primordium |
| T2 Seedling Expression<br>Events Screened: n = 3 | Tissues Screened<br>Events Expressing: n = 3 |
| Seedlings expressing/Seedlings screened | |
| Event-01: 3/5<br>Event-02: 2/7<br>Event-03: 4/5 | |
| X Hypocotyl | L epidermis □cortex □ vascular □xylem □phloem □stomata |
| X Cotyledon | □mesophyll □ vascular L epidermis □margin H petiole □ stomata □hydathode |
| X Rosette Leaf | □mesophyll □vascular H epidermis □trichome H petiole □primordia □stomata □stipule □margin □hydathode |
| X Primary Root | H epidermis □trichoblast □atrichoblast □cortex □endodermis □ vascular □xylem □phloem □pericycle □quiescent □columella □ root cap □ root hairs |
| □ Lateral root | □epidermis □trichoblast □atrichoblast □cortex □endodermis □initials □primordia □flanking cells □vascular □lateral root cap |
| □ Shoot apical meristem | □Shoot apical meristem |
| Promoter utility | |
| Trait Area: | Plant Growth and Development |
| Sub-trait Area: | Growth Control, flowering and abscission |
| Utility: | Among other uses this promoter sequence can be used to improve: growth rate, plant size, branching, stature, seedling establishment and growth rate response to shade and low light, flower and fruit lifetime and abscission, water and nutrient uptake and resistance to root nematodes |
| Notes: | 1. FIN219, an auxin-regulated gene, defines a link between phytochrome A and the downstream regulator COP1 in light control of *Arabidopsis* development. Hsieh HL, Okamoto H, Wang M, Ang LH, Matsui M, Goodman H, Deng XW. Genes Dev. 2000 Aug 1; 14(15): 1958-1970. PMCID: 316819<br>2. SPINDLY and GIGANTEA Interact and Act in *Arabidopsis thaliana* Pathways Involved in Light Responses, Flowering, and Rhythms in Cotyledon Movements. Tseng TS, Salome PA, McClung CR, Olszewski NE. Plant Cell. 2004 Jun; 16(6): 1550-1563. PMCID: 490045.<br>3. Interaction of Cryptochrome 1, Phytochrome, and Ion Fluxes in Blue-Light-Induced Shrinking of *Arabidopsis* Hypocotyl Protoplasts. Wang X, Iino M. Plant Physiol. 1998 Aug 1; 117(4): 1265-1279. PMCID: 34890<br>4. shl, a New Set of *Arabidopsis* Mutants with Exaggerated Developmental Responses to Available Red, Far-Red, and Blue Light. Pepper AE, Seong-Kim MS, Hebst SM, Ivey KN, Kwak SJ, Broyles DE. Plant Physiol. 2001 Sep 1; 127(1): 295-304. PMCID: 117985 |
| Construct: | PT0852 |
| Promoter candidate I.D: | 15295946 |
| cDNA I.D: | 23516971 |
| Events expressing: | 02, 03, 05 |

Example 39

| Promoter Expression Report #200.PT0857 | |
|---|---|
| Promoter Tested In: | *Arabidopsis thaliana*, Wassilewskija (WS) ecotype |
| | Spatial expression summary: |
| Mature Root | H mature root |
| Hypocotyl | H epidermis H cortex H vascular |
| Cotyledon | H petiole |
| Primary Root | H vascular L pericycle |
| Lateral Root | H pericycle H initials H flanking cells H vascular |
| | Observed expression pattern: |
| T1 mature: | GFP expressed in roots of mature plants. No expression observed in aerial organs. |
| T2 seedling: | High GFP expression throughout hypocotyl and petioles of cotyledons. In root, GFP is highly expressed throughout vasculature and pericycle cells in regions of lateral root formations. |
| T2 mature: | GFP expressed in roots of mature plants. *Observed in aerial tissues in 1 of 6 events screened |
| Expected expression pattern: | Up in roots only |
| Selection Criteria: | *Arabidopsis thaliana*, Microarray |
| Gene: | Proton-dependent oligopeptide transport (POT) family protein |
| GenBank: | NM_114439 *Arabidopsis thaliana* proton-dependent oligopeptide transport (POT) family protein (At3g45700) mRNA, complete cds gi\|30692627\|ref\|NM_114439.2\|[30692627] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | XT1 Mature XT2 Seedling XT2 Mature □T3 Seedling |
| | T1 Mature Plant Expression Organs/Tissues screened<br>Events Screened: n = 3 Events Expressing: n ≧ 1 |
| □ Flower | □pedicel □receptacle □nectary □sepal □petal □filament □anther □pollen □carpel □style □papillae □vascular □epidermis □stomata □trichome □silique |
| □ Silique | □stigma □style □carpel □septum □placentae □funiculus □transmitting tissue □vascular □epidermis □stomata □ abscission zone □ovule |
| □ Ovule | Pre-fertilization: □primordia □inner integument □outer integument □embryo sac □funiculus □chalaza □micropyle □gametophyte<br>Post-fertilization: □zygote □suspensor □ embryo sack □funiculus □inner integument □ outer integument □ endothelium □ seed coat □primordia □chalaza □micropyle □early endosperm □mature endosperm □embryo |
| □ Embryo | □suspensor □preglobular □globular □heart □torpedo □late mature □provascular □hypophysis □radicle □cotyledons □root meristem □shoot meristem |
| □ Stem | □epidermis □cortex □interfascicular region □vascular □xylem □phloem □pith □stomata □trichome |
| □ Leaf | □petiole □mesophyll □vascular □epidermis □trichome □primordia □stomata □stipule □margin |
| □ Shoot apical meristem | □ Shoot apical meristem □ Flower primordium |
| X Mature Root | H mature root |
| | T2 Seedling Expression Tissues Screened<br>Events Screened: n = 3 Events Expressing: n = 3 |
| | Seedlings expressing/Seedlings screened |
| | Event-01: 3/6<br>Event-02: 4/6<br>Event-03: 4/6 |
| X Hypocotyl | H epidermis H cortex H vascular □xylem □phloem □stomata |
| X Cotyledon | □mesophyll □ vascular □ epidermis □margin H petiole □stomata □hydathode |
| □ Rosette Leaf | □mesophyll □vascular □epidermis □trichome □petiole □primordia □stomata □stipule □margin □hydathode |
| X Primary Root | □ epidermis □trichoblast □atrichoblast □cortex □endodermis H vascular □xylem □phloem L pericycle □quiescent □columella □root cap □root hairs |
| X Lateral root | □epidermis □trichoblast □atrichoblast □cortex □endodermis H pericycle<br>H initials H flanking cells H vascular □lateral root cap |
| □ Shoot apical meristem | □Shoot apical meristem |

-continued

| Promoter Expression Report #200.PT0857 | |
|---|---|
| | T2 Mature Plant Expression Organs/Tissues screened<br>Events Screened: n = 6 Events Expressing: n = 5 |
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐funiculus ☐transmitting tissue ☐vascular ☐epidermis ☐stomata ☐ abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐ embryo sack ☐funiculus ☐inner integument ☐ outer integument ☐ endothelium ☐ seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late mature ☐provascular ☐hypophysis ☐radicle ☐cotyledons ☐root meristem ☐shoot meristem |
| ☐ Stem | ☐epidermis ☐cortex ☐interfascicular region ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| X Aerial organs | H inflorescence meristem ☐ shoot apical meristem ☐ flower primordium H flowers ☐silique ☐ovule ☐embryo L stem ☐ leaf |
| X Mature root | H Mature root |

High GFP expression specific in roots for 5 of 6 events scanned. Event 04: GFP expression in aerial organs in addition to root.

Promoter utility

| | |
|---|---|
| Trait Area: | Nutrients, PG&D |
| Sub-trait Area: | Nutrient uptake, growth rate |
| Utility: | Among other uses this promoter sequence can be used to |
| improve: | Nutrient uptake, seedling establishment |
| Construct: | PT0857 |
| Promoter candidate I.D: | 15371818 |
| cDNA I.D: | 23507609 |
| Events expressing: | PT0857-01, -02, -03, -04, -06 |

Example 40

| Promoter Expression Report #255.PT0757 | |
|---|---|
| Promoter Tested In: | *Arabidopsis thaliana*, Wassilewskija (WS) ecotype |
| | Spatial expression summary: |
| Primary Root | H epidermis H cortex |
| | Observed expression pattern: |
| T1 mature: | No expression observed. |
| T2 seedling: | GFP specific to root epidermis and cortex cells. Highest expression near root transition zone decreasing near root elongation zone. No expression in lateral root. |
| T2 Mature: | No expression observed. |
| Expected expression pattern: | Up in roots only |
| Selection Criteria: | *Arabidopsis thaliana*, Microarray |
| Gene: | 2-oxoglutarate-dependent dioxygenase, putative |
| GenBank: | NM_128637 *Arabidopsis thaliana* 2-oxoglutarate-dependent dioxygenase, putative (At2g30840) mRNA, complete cds gi\|42569490\|ref\|NM_128637.3\|[42569490] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling X T2 Mature ☐T3 Seedling |
| | T1 Mature Plant Expression Organs/Tissues screened<br>Events Screened: n = 3 Events Expressing: n = 0 |
| | No GFP Expression Detected |
| | T2 Seedling Expression Tissues Screened<br>Events Screened: n = 3 Events Expressing: n = 2 |
| | Seedlings expressing/Seedlings screened |

-continued

| Promoter Expression Report #255.PT0757 | |
|---|---|
| | Event-01: 4/6<br>Event-02: 3/6 |
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐petiole ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | H epidermis ☐trichoblast ☐atrichoblast H cortex ☐ endodermis ☐vascular ☐xylem ☐phloem ☐pericycle ☐quiescent ☐columella ☐root cap ☐root hairs |
| ☐ Lateral Root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |
| T2 Mature Plant Expression Events Screened: n = 6 | Organs/Tissues screened Events Expressing: n = 0 |
| No GFP Expression Detected | |
| Promoter utility | |
| Trait Area: | Nutrients |
| Sub-trait Area: | low nitrogen tolerance, |
| Utility: | Among other uses this promoter sequence can be used to improve: low nitrogen tolerance and resistance to root insects and nematodes |
| Construct: | PT0757 |
| Promoter candidate I.D: | 15371857 |
| cDNA I.D: | 23496046 |
| Events expressing: | PT0757-01, -02 |

Example 41

| Promoter Expression Report #256.PT0764 | |
|---|---|
| Promoter Tested In: | *Arabidopsis thaliana*, Wassilewskija (WS) ecotype |
| Spatial expression summary: | |
| Primary Root | H epidermis |
| Observed expression pattern: | |
| T1 mature: | No expression observed. |
| T2 seedling: | High GFP expression specific to root epidermis cells. |
| T2 mature: | Weak GFP expression detected in roots. |
| Expected expression pattern: | Up in roots only |
| Selection Criteria: | *Arabidopsis thaliana*, Microarray |
| Gene: | Short-chain dehydrogenase/reductase (SDR) family protein |
| GenBank: | NM_202867 *Arabidopsis thaliana* short-chain dehydrogenase/reductase (SDR) family protein (At4g23420) mRNA, complete cds gi\|42572998\|ref\|NM_202867.1\|[42572998] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling X T2 Mature ☐T3 Seedling |
| T1 Mature Plant Expression Events Screened: n = 3 | Organs/Tissues screened Events Expressing: n = 0 |
| No GFP Expression Detected | |
| T2 Seedling Expression Events Screened: n = 2 | Tissues Screened Events Expressing: n = 3 |
| Seedlings expressing/Seedlings screened | |
| | Event-01: 3/6<br>Event-02: 5/6 |
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐petiole ☐stomata ☐hydathode |

-continued

| Promoter Expression Report #256.PT0764 | |
|---|---|
| ☐ Rosette Leaf | ☐mesophyll ☐vascular ☐epidermis ☐trichome ☐petiole ☐primordia ☐stomata ☐stipule ☐margin ☐hydathode |
| X Primary Root | H epidermis ☐trichoblast ☐atrichoblast ☐cortex ☐ endodermis ☐vascular ☐xylem ☐phloem ☐pericycle ☐quiescent ☐columella ☐root cap ☐root hairs |
| ☐ Lateral Root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

| T2 Mature Plant Expression Events Screened: n = 6 | Organs/Tissues screened Events Expressing: n = 2 |
|---|---|
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐funiculus ☐transmitting tissue ☐vascular ☐epidermis ☐stomata ☐ abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐ embryo sack ☐funiculus ☐inner integument ☐ outer integument ☐ endothelium ☐ seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late mature ☐provascular ☐hypophysis ☐radicle ☐cotyledons ☐root meristem ☐shoot meristem |
| ☐ Stem | ☐epidermis ☐cortex ☐interfascicular region ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Aerial organs | ☐ inflorescence meristem ☐ shoot apical meristem ☐ flower primordium ☐silique ☐ovule ☐embryo ☐ stem ☐ leaf |
| X Mature Root | L mature root |

Low GFP expression detected in roots of events -02 and -05.

| Promoter utility | |
|---|---|
| Trait Area: | Nutrients, Biotic stress |
| Sub-trait Area: | low nitrogen tolerance, nematode resistance |
| Utility: | Among other uses this promoter sequence can be used to |
| improve: | Tolerance to low nutrients, nematode resistance |
| Construct: | PT0764 |
| Promoter candidate I.D: | 15371890 |
| cDNA I.D: | 1819818 |
| Events expressing: | PT0764-01, -02, -05 |

Example 42

| Promoter Expression Report #257.PT0767 | |
|---|---|
| Promoter Tested In: | *Arabidopsis thaliana*, Wassilewskija (WS) ecotype |
| Spatial expression summary: | |
| Lateral Root | H cortex H initials H flanking cells H lateral root cap |
| Observed expression pattern: | |
| T1 mature: | No expression observed. |
| T2 seedling: | High GFP expression specific to lateral root primordial and cortex cells overlaying lateral root initiation sites. |
| T2 mature: | No expression detected. |
| Expected expression pattern: | Up in roots only |
| Selection Criteria: | *Arabidopsis thaliana*, Microarray |
| Gene: | expressed protein |
| GenBank: | NM_129494 *Arabidopsis thaliana* expressed protein (At2g39370) mRNA, complete cds gi\|18405026\|ref\|NM_129494.1\|[18405026] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling X T2 Mature ☐T3 Seedling |

-continued

| Promoter Expression Report #257.PT0767 | |
|---|---|
| T1 Mature Plant Expression Events Screened: n = 3 | Organs/Tissues screened Events Expressing: n = 0 |
| No GFP Expression Detected | |
| Table 2. T2 Seedling Expression Events Screened: n = 3 | Tissues Screened Events Expressing: n = 2 |
| Seedlings expressing/Seedlings screened | |
| Event-02: 2/6 Event-03: 3/6 | |
| □ Hypocotyl | □epidermis □cortex □vascular □xylem □phloem □stomata |
| □ Cotyledon | □mesophyll □vascular □epidermis □margin □petiole □stomata □hydathode |
| □ Rosette Leaf | □mesophyll □vascular □epidermis □trichome □petiole □primordia □stomata □stipule □margin □hydathode |
| □ Primary Root | □epidermis □trichoblast □atrichoblast □cortex □ endodermis □vascular □xylem □phloem □pericycle □quiescent □columella □root cap □root hairs |
| X Lateral Root | □epidermis □trichoblast □atrichoblast H cortex □endodermis H initials H flanking cells □vascular H lateral root cap |
| □ Shoot apical meristem | □shoot apical meristem |
| T2 Mature Plant Expression Events Screened: n = 6 | Organs/Tissues screened Events Expressing: n = 0 |
| No GFP Expression Detected | |
| Promoter utility | |
| Trait Area: | Nutrients, PG&D |
| Sub-trait Area: | low nitrogen tolerance, seedling establishment |
| Utility: | Among other uses this promoter sequence can be used to |
| improve: | Low nitrogen tolerance, seedling establishment, root worm and nematode resistance |
| Construct: | PT0767 |
| Promoter candidate I.D: | 15371902 |
| cDNA I.D: | 23519162 |
| Events expressing: | PT0767-02, -03 |

Example 43

| Promoter Expression Report #259.PT0776 | |
|---|---|
| Promoter Tested In: | *Arabidopsis thaliana*, Wassilewskija (WS) ecotype |
| Spatial expression summary: | |
| Mature Root | L mature root |
| Primary Root | H pericycle |
| Lateral Root | H initials |
| Observed expression pattern: | |
| T1 mature: | No expression observed. |
| T2 seedling: | High GFP expression specific to pericycle cells and lateral root initials. |
| T2 mature: | Low GFP expression in roots. |
| Expected expression pattern: | Up in roots only |
| Selection Criteria: | *Arabidopsis thaliana*, Microarray |
| Gene: | CLAVATA1 receptor kinase (CLV1) |
| GenBank: | NM_100732 *Arabidopsis thaliana* CLAVATA1 receptor kinase (CLV1) (At1g08590) mRNA, complete cds gi\|30680710\|ref\|NM_100732.2\|[30680710] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling XT2 Mature □T3 Seedling |
| T1 Mature Plant Expression Events Screened: n = 0 | Organs/Tissues screened Events Expressing: n = 3 |

-continued

| Promoter Expression Report #259.PT0776 | |
|---|---|
| No GFP Expression Detected | |
| T2 Seedling Expression Tissues Screened<br>Events Screened: n = 3 Events Expressing: n = 2 | |
| Seedlings expressing/Seedlings screened | |
| Event-02: 1/6<br>Event-03: 2/6 | |
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐petiole ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | ☐epidermis ☐trichoblast ☐atrichoblast ☐cortex ☐ endodermis ☐vascular ☐xylem ☐phloem H pericycle ☐quiescent ☐columella ☐root cap ☐root hairs |
| X Lateral Root | ☐epidermis ☐trichoblast ☐atrichoblast ☐cortex ☐endodermis H initials ☐flanking cells ☐vascular ☐lateral root cap |
| ☐ Shoot apical meristem | ☐shoot apical meristem |
| T2 Mature Plant Expression Organs/Tissues screened<br>Events Screened: n = 5 Events Expressing: n = 4 | |
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐funiculus ☐transmitting tissue ☐vascular ☐epidermis ☐stomata ☐ abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐ embryo sack ☐funiculus ☐inner integument ☐ outer integument ☐ endothelium ☐ seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late mature ☐provascular ☐hypophysis ☐radicle ☐cotyledons ☐root meristem ☐shoot meristem |
| ☐ Stem | ☐epidermis ☐cortex ☐interfascicular region ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Aerial organs | ☐inflorescence meristem ☐ shoot apical meristem ☐ flower primordium ☐silique ☐ovule ☐embryo ☐ stem ☐ leaf |
| X Mature Root | L mature root |
| Promoter utility | |
| Trait Area: | Nutrients, Drought, PG&D |
| Sub-trait Area: | Low nutrient uptake, drought tolerance, seedling establishment |
| Utility: | Among other uses this promoter sequence can be used to |
| improve: | Drought tolerance, low nitrogen tolerance, seedling establishment, root insect and nematode resistance. |
| Construct: | PT0776 |
| Promoter candidate I.D: | 15371953 |
| cDNA I.D: | 23515451 |
| Events expressing: | PT0776-02, -03, -04, -05 |

55

Example 44

| Promoter Expression Report #260.PT0889 | |
|---|---|
| Promoter Tested In: | *Arabidopsis thaliana*, Wassilewskija (WS) ecotype |
| Spatial expression summary: | |
| Lateral Root | H initials H primordia |
| Observed expression pattern: | |

-continued

| Promoter Expression Report #260.PT0889 | |
|---|---|
| T1 mature: | No expression observed. |
| T2 seedling: | GFP expression specific to lateral root initials and primordia. |
| T2 mature: | No expression detected. |
| Expected expression pattern: | Up in roots only |
| Selection Criteria: | *Arabidopsis thaliana*, Microarray |
| Gene: | basic helix-loop-helix (bHLH) family protein |
| GenBank: | NM_179235 *Arabidopsis thaliana* basic helix-loop-helix (bHLH) family protein (At4g36060) mRNA, complete cds gi\|30690567\|ref\|NM_179235.1\|[30690567] |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling X T2 Mature □T3 Seedling |
| T1 Mature Plant Expression<br>Events Screened: n = 3 | Organs/Tissues screened<br>Events Expressing: n = 0 |
| No GFP Expression Detected | |
| T2 Seedling Expression<br>Events Screened: n = 3 | Tissues Screened<br>Events Expressing: n = 2 |
| Seedlings expressing/Seedlings screened | |
| Event-01: 4/6<br>Event-02: 3/6 | |
| □ Hypocotyl | □epidermis □cortex □vascular □xylem □phloem □stomata |
| □ Cotyledon | □mesophyll □vascular □epidermis □margin □petiole □stomata □hydathode |
| □ Rosette Leaf | □mesophyll □vascular □epidermis □trichome □petiole □primordia □stomata □stipule □margin □hydathode |
| □ Primary Root | □epidermis □trichoblast □atrichoblast □cortex □ endodermis □vascular □xylem □phloem □pericycle □quiescent □columella □root cap □root hairs |
| X Lateral Root | □epidermis □trichoblast □atrichoblast □cortex □endodermis H initials H primordia □flanking cells □vascular □lateral root cap |
| □ Shoot apical meristem | □shoot apical meristem |
| T2 Mature Plant Expression<br>Events Screened: n = 5 | Organs/Tissues screened<br>Events Expressing: n = 0 |
| No GFP Expression Detected | |
| Promoter utility | |
| Trait Area: | PG&D |
| Sub-trait Area: | Growth rate, root biomass |
| Utility: improve: | Among other uses this promoter sequence can be used to root biomass, seedling establishment, drought tolerance, tolerance to low nutrients. |
| Construct: | PT0889 |
| Promoter candidate I.D: | 15371968 |
| cDNA I.D: | 23504527 |
| Events expressing: | PT0889-01, -02 |

Example 45

| Promoter Expression Report #267.PT0585 | |
|---|---|
| Promoter Tested In: | *Arabidopsis thaliana*, Wassilewskija (WS) ecotype |
| Spatial expression summary: | |
| Flower | H pedicel H sepal H carpel H epidermis H silique |
| Silique | H style H carpel H septum H epidermis |
| Stem | H epidermis H cortex |
| Leaf | H mesophyll H vascular H epidermis |
| Hypocotyl | L epidermis |
| Cotyledon | H mesophyll H epidermis |
| Observed expression pattern: | |
| T1 Mature expression: | GFP broadly expressed throughout vegetative organs. No expression in stamen, placenta or ovules of flowers. High GFP expression in pedicels and sepals of developing flowers and in siliques of abscised flowers. No expression in silique of early stage and developing |

-continued

| Promoter Expression Report #267.PT0585 | |
|---|---|
| | flower. High GFP expression in epidermis, vascular, and mesophyll cells of leaf. High GFP expression in epidermis and cortex cells of stem. |
| T2 Seedling expression: | High GFP expression in epidermis and mesophyll cells of cotyledons with low expression in hypocotyls. No expression in root. |
| Expected expression pattern: | *Arabidopsis* knockout line gametophytic lethal |
| Selection Criteria: | Mutant lines |
| Gene: | glutamine synthetase, putative |
| GenBank: | NM_122954 glutamine synthetase (GS2) (At5g35630) mRNA, complete cds |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling ☐T2 Mature ☐T3 Seedling |

T1 Mature Plant Expression Events Screened: n = 3 — Organs/Tissues screened Events Expressing: n = 2

GFP expression as shown below

| | |
|---|---|
| X Flower | H pedicel ☐receptacle ☐nectary H sepal ☐petal ☐filament ☐anther ☐pollen H carpel ☐style ☐papillae ☐vascular H epidermis ☐stomata ☐trichome H silique |
| X Silique | ☐stigma H style H carpel H septum ☐placentae ☐funiculus ☐transmitting tissue ☐vascular H epidermis ☐stomata ☐ abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐ embryo sack ☐funiculus ☐inner integument ☐ outer integument ☐ endothelium ☐ seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late mature ☐provascular ☐hypophysis ☐radicle ☐cotyledons ☐root meristem ☐shoot meristem |
| X Stem | H epidermis H cortex ☐interfascicular region ☐vascular ☐xylem ☐phloem ☐pith ☐stomata ☐trichome |
| X Leaf | ☐petiole H mesophyll H vascular H epidermis ☐trichome ☐primordia ☐stomata ☐stipule ☐margin |
| ☐ Shoot apical meristem | ☐ Shoot apical meristem ☐ Flower primordium |

T2 Seedling Expression Events Screened: n = 6 — Tissues Screened Events Expressing: n = 5

Seedlings expressing/Seedlings screened

Event-01: 4/6
Event-02: 5/6

| | |
|---|---|
| X Hypocotyl | L epidermis ☐cortex ☐ vascular ☐xylem ☐phloem ☐stomata |
| X Cotyledon | H mesophyll ☐ vascular H epidermis ☐margin ☐petiole ☐ stomata ☐hydathode |
| ☐ Rosette Leaf | ☐mesophyll ☐ vascular ☐epidermis ☐trichome ☐petiole ☐primordia ☐stomata ☐stipule ☐margin ☐hydathode |
| ☐ Primary Root | ☐ epidermis ☐trichoblast ☐atrichoblast ☐ cortex ☐ endodermis ☐ vascular ☐xylem ☐phloem ☐pericycle ☐quiescent ☐columella ☐ root cap ☐ root hairs |
| ☐ Lateral Root | ☐epidermis ☐trichoblast ☐atrichoblast ☐cortex ☐endodermis ☐initials ☐primordia ☐flanking cells ☐vascular ☐lateral root cap |
| ☐ Shoot apical meristem | ☐Shoot apical meristem |

Scan of seedlings from 6 events of line PT0585. GFP expression was observed in 5 of 6 events (7 days old). Events-01, -02. -04, -05, -06 showed expression, while -03 showed no expression T2 Mature Plant Expression Events Screened: n = 6 — Organs/Tissues screened Events Expressing: n = 6

| | |
|---|---|
| X Aerial organs | H inflorescence meristem ☐ shoot apical meristem ☐ flower primordium H silique ☐ovule ☐embryo H stem H leaf |
| X Mature root | H mature root |

Promoter utility

| | |
|---|---|
| Trait Area: | Plant growth and development |
| Sub-trait Area: | Source Strength |
| Utility: | Among other uses this promoter sequence can be used to |

-continued

| Promoter Expression Report #267.PT0585 | |
|---|---|
| improve: | plant biomass, size, stature, xylem and mechanical properties. Also seed filling, seed size, seed yield, seed composition. Manipulation of dehiscence and seed scatter. |
| Construct: | PT0585 |
| Promoter candidate I.D: | 11768829 |
| cDNA I.D: | 23531789 |
| Events expressing: | PT0585-01, -02, -04, -05, -06 |

Example 46

| Promoter Expression Report #268.PT0565 | |
|---|---|
| Promoter Tested In: | *Arabidopsis thaliana*, Wassilewskija (WS) ecotype |
| | Spatial expression summary: |
| Flower | H pedicel H sepal H petal H anther H carpel H style H epidermis H silique |
| Silique | H carpel H septum H epidermis H ovule |
| Ovule | Post-fertilization: H outer integument H seed coat H embryo |
| Embryo | H torpedo H late H mature H radicle H cotyledons |
| Stem | H epidermis H cortex H vascular H xylem H phloem L pith |
| Shoot apical meristem | L shoot apical meristem |
| Mature Root | H mature root H vascular |
| Hypocotyl | L vascular |
| Cotyledon | H mesophyll H epidermis |
| Rosette Leaf | H mesophyll H epidermis |
| Primary Root | H vascular |
| | Observed expression pattern: |
| T1 Mature expression: | High GFP expression in flowers, root and stem. GFP expressed throughout all organs of the flower with highest expression in developing and mature siliques. High GFP expression in developing seed coats and embryos. GFP is expressed in epidermis, cortex, pith, and vascular bundles of stem. High GFP in vasculature of roots of mature plants. |
| T2 Seedling expression: | High GFP expression in epidermis and mesophyll of expanding cotyledons and rosette leaves. GFP also expressed in vasculature of root. |
| Expected expression pattern: | Dividing cells |
| Selection Criteria: | Public reference |
| Gene: | cyclin, putative |
| GenBank: | NM_103537 *Arabidopsis thaliana* cyclin, putative (At1g44110) mRNA, complete cds |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling □ T2 Mature □T3 Seedling |

| | T1 Mature Plant Expression Organs/Tissues screened<br>Events Screened: n = 3 Events Expressing: n = 2 |
|---|---|
| X Flower | H pedicel □receptacle □nectary H sepal H petal □filament H anther □pollen H carpel H style □papillae □vascular H epidermis □stomata □trichome H silique |
| X Silique | □stigma □style H carpel H septum □placentae □funiculus □transmitting tissue □vascular H epidermis □stomata □ abscission zone H ovule |
| X Ovule | Pre-fertilization: □primordia □inner integument □outer integument □embryo sac □funiculus □chalaza □micropyle □gametophyte Post-fertilization: □zygote □suspensor □ embryo sack □funiculus □inner integument H outer integument □ endothelium H seed coat □primordia □chalaza □micropyle □early endosperm □mature endosperm H embryo |
| X Embryo | □suspensor □preglobular □globular □heart H torpedo H late H mature □provascular □hypophysis H radicle H cotyledons □root meristem □shoot meristem |
| X Stem | H epidermis H cortex □interfascicular region H vascular H xylem H phloem L pith □stomata □trichome |
| □ Leaf | □petiole □mesophyll □vascular □epidermis □trichome □primordia □stomata □stipule □margin |
| X Shoot apical meristem | L shoot apical meristem □ Flower primordium |
| X Mature Root | H mature root H vascular |

-continued

| Promoter Expression Report #268.PT0565 | |
|---|---|
| T2 Seedling Expression<br>Events Screened: n = 6 | Tissues Screened<br>Events Expressing: n = 4 |
| Seedlings expressing/Seedlings screened | |
| Event-01: 3/6<br>Event-02: 5/6<br>Event-05: 4/6<br>Event-06: 4/6 | |
| X Hypocotyl | ☐epidermis ☐cortex L vascular ☐xylem ☐phloem ☐stomata |
| X Cotyledon | H mesophyll ☐ vascular H epidermis ☐margin ☐petiole ☐ stomata<br>☐hydathode |
| X Rosette Leaf | H mesophyll ☐ vascular H epidermis ☐trichome ☐petiole<br>☐primordia ☐stomata ☐stipule ☐margin ☐hydathode |
| X Primary Root | ☐ epidermis ☐trichoblast ☐atrichoblast ☐ cortex ☐ endodermis<br>H vascular ☐xylem ☐phloem ☐pericycle ☐quiescent<br>☐columella ☐ root cap ☐ root hairs |
| ☐ Lateral root | ☐epidermis ☐trichoblast ☐atrichoblast ☐cortex ☐endodermis<br>☐initials ☐primordia ☐flanking cells ☐vascular ☐lateral root cap |
| ☐ Shoot apical meristem | ☐Shoot apical meristem |
| Scan of seedlings from six Events of line PT0565. GFP expression (+) observed in 4 of 6 events. Events-01, -02, -05, -06 showed expression, while events -03, and -04 did not show expression. | |
| Promoter utility | |
| Trait Area: | Plant growth and development |
| Sub-trait Area: | Size and source capacity |
| Utility:<br>improve: | Among other uses this promoter sequence can be used to plant size and architecture, growth rate, seedling establishment, responses to shade and low light, responses to drought and cold, source capacity and sucrose loading, seed filling, seed size and plant yield. |
| Notes: | Similar to mitotic cyclin a2-type [*Glycine max*] GI: 857397, cyclin A-like protein [*Nicotiana tabacum*] GI: 1064927; contains Pfam profiles PF00134: Cyclin, N-terminal domain, PF02984: Cyclin, C-terminal domain product cyclin, putative protein__id NP__175077.1<br>CLUSTAL MUSCLE (3.52) multiple sequence alignment<br>>*Lycopersicon esculentum* var. *cerasiforme* mRNA for protein kinase WEE1 (wee1 gene)<br>>*Arabidopsis thaliana* cyclin, putative (At1g44110) mRNA, complete cds<br>Coding sequence alignment: Percentage of identity: 59.9%<br>Protein sequence alignment: Percentage of identity: 17.0%<br>Gonzalez N, Hernould M, Delmas F, Gevaudant F, Duffe P, Causse M. Mouras A, Chevalier C. Molecular characterization of a WEE1 gene homologue in tomato (*Lycopersicon esculentum* Mill.). Plant Mol Biol. 2004 Dec; 56(6): 849-61. Epub 2005 Apr 7. PMID: 15821985 [PubMed - in process]<br>Early fruit development in tomato (*Lycopersicon esculentum* Mill.) proceeds in two distinct phases of growth that comprise cell division and cell expansion, respectively. In pericarp and the jelly like locular tissue of tomato fruit, the transition between cell division to cell expansion is characterized by the arrest of mitotic activity, numerous rounds of nuclear DNA endoreduplication and the inhibition of Cyclin-Dependent Kinase A (CDKA) activity. To investigate whether the WEE1 kinase may play a role during the endoreduplication process, we isolated and characterized the tomato homologue for WEE1. The LeWEE1 gene consisted of 10 exons with a predicted 510 amino acid-long protein. The accumulation of the corresponding transcripts was associated with mitotically active organs: developing fruits, seeds and roots. Interestingly, LeWEE1 was expressed in the jelly like locular tissue concomitant with endoreduplication during fruit development. Using tobacco BY-2 synchronized cells, we showed that the WEE1 gene expression is cell-cycle regulated with a maximum transcript accumulation at S phase. Our data indicate the putative dual contribution of LeWEE1 in the classical cell cycle and the endocycle. |
| Construct: | PT0565 |
| Promoter candidate I.D: | 11768774 |
| cDNA I.D: | 23521098 |
| Events expressing: | PT0565 -01, -02, -05, -06 |

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

What is claimed is:

1. An isolated nucleic acid molecule that modulates transcription consisting of SEQ ID NO:37 or a functional fragment thereof having promoter activity.

2. The isolated nucleic acid molecule of claim 1, wherein said nucleic acid molecule modulates transcription during the developmental times, or in response to a stimuli, or in a cell, tissue, or organ as set forth for SEQ ID NO:37 in corresponding Example 37 in the section “Spatial expression summary”.

3. A vector construct comprising:

a) a first nucleic acid molecule that modulates transcription, consisting of SEQ ID NO:37 or a functional fragment thereof having promoter activity; and b) a second nucleic acid having to be transcribed, wherein said first and second nucleic acid molecules are heterologous to each other and are operably linked together.

4. A host cell comprising the isolated nucleic acid molecule according to claim 1, wherein said nucleic acid molecule is flanked by exogenous sequence.

5. A host cell comprising the vector construct of claim 3.

6. A method of modulating transcription by combining, in an environment suitable for transcription:

a) a first nucleic acid molecule that modulates transcription consisting of SEQ ID NO:37 or a functional fragment thereof having promoter activity; and b) a second molecule to be transcribed;

wherein the first and second nucleic acid molecules are heterologous to each other and operably linked together.

7. The method according to claim 6, wherein said first nucleic acid molecule is transformed into a plant cell and said plant cell is regenerated into a plant.

8. The method according to claim 6, wherein said first nucleic acid molecule modulates transcription during the developmental times, or in response to a stimuli, or in a cell tissue, or organ as set forth for SEQ ID NO:37 in the corresponding Example 37 in the section entitled "Spatial expression summary".

9. A plant comprising the vector construct according to claim 3.

10. A method of introducing an isolated nucleic acid molecule into a host cell comprising:

(a) providing the isolated nucleic acid molecule according to claim 1; and (b) contacting said isolated nucleic acid molecule with said host cell under conditions that permit transformation of said isolated nucleic acid molecule into said host cell.

11. A plant, plant cell, plant material or plant seed which comprises the nucleic acid molecule according to claim 1 which is exogenous or heterologous to said plant or plant cell.

12. A plant, plant cell, plant material or plant seed which comprises the vector construct according to claim 3.

13. A plant that has been regenerated from the plant cell or plant seed according to claim 11 or 12.

14. A plant, plant cell, plant material or seed of a plant which comprises the nucleic acid molecule according to claim 1, wherein said plant has an improved property or characteristic as compared to an untransformed control plant cultivated under the same conditions.

* * * * *